(12) United States Patent
Vos et al.

(10) Patent No.: US 7,790,719 B2
(45) Date of Patent: *Sep. 7, 2010

(54) MODULATORS OF MELANOCORTIN RECEPTOR

(75) Inventors: Tricia J. Vos, Medford, MA (US); Michael Patane, Andover, MA (US); Michael E. Solomon, Concord, MA (US); Christopher Blackburn, Natick, MA (US); Mihaela D. Danca, Belmont, MA (US)

(73) Assignee: Ore Pharmaceuticals, Inc., Cambridge, MA (US)

( * ) Notice: Subject to any disclaimer, the term of this patent is extended or adjusted under 35 U.S.C. 154(b) by 287 days.

This patent is subject to a terminal disclaimer.

(21) Appl. No.: 11/878,708

(22) Filed: Jul. 26, 2007

(65) Prior Publication Data

US 2007/0293498 A1    Dec. 20, 2007

Related U.S. Application Data

(63) Continuation of application No. 10/727,997, filed on Dec. 4, 2003, now Pat. No. 7,365,070.

(60) Provisional application No. 60/430,789, filed on Dec. 4, 2002.

(51) Int. Cl.
A61K 31/505      (2006.01)
A61K 31/535      (2006.01)
A61K 31/517      (2006.01)
A61K 31/445      (2006.01)
C07D 239/02      (2006.01)
C07D 233/88      (2006.01)
C07D 413/14      (2006.01)
C07D 239/70      (2006.01)

(52) U.S. Cl. .................... 514/235.8; 544/332; 544/122; 544/253; 548/332.5; 546/210; 514/275; 514/258.1; 514/326; 514/398

(58) Field of Classification Search ................. 544/332, 544/253, 122; 514/275, 326, 235.8; 548/332.5
See application file for complete search history.

(56) References Cited

U.S. PATENT DOCUMENTS 4,973,731 A * 11/1990 Rustad .................... 558/389
5,693,672 A   12/1997 Weichert et al.
6,600,072 B2  7/2003  Brendel et al. ............... 564/165
6,699,873 B1  3/2004  Maguire et al.
2002/0137939 A1  9/2002  Renhowe et al.

FOREIGN PATENT DOCUMENTS

EP          0 676 395 A       10/1995

(Continued)

OTHER PUBLICATIONS

P. Vigne et al.; "Structure-Activity Relationships of Amiloride and Certain of Its Analogues in Relation to the Blockade of the Na+/H+ Exchange System", pp. 131-136, 25(1), Sep. 20, 1983.

(Continued)

*Primary Examiner*—Rebecca L Anderson
(74) *Attorney, Agent, or Firm*—Harness, Dickey & Pierce, P.L.C.; J. Timothy Keane; Kisuk Lee

(57) ABSTRACT

This invention provides compounds and methods for treating melanocortin receptor associated disorders, such as weight loss disorders including cachexia resulting from cancer and other chronic illnesses. The compounds are represented by formula I:

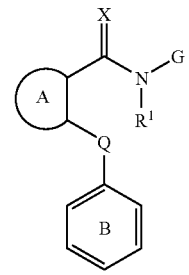

I wherein X is oxygen or sulfur; G is G1 or G2:

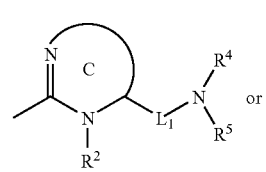

G1

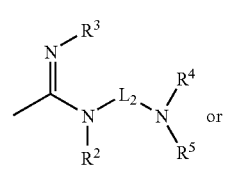

G2

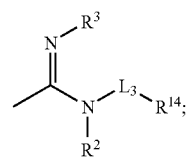

G3

$L_1$, $L_2$, $L_3$ and Q are linker groups, and Rings A, B and C, and $R^1$-$R^{14}$ are described in the specification. The compounds are antagonists of melanocortin receptors.

18 Claims, No Drawings

FOREIGN PATENT DOCUMENTS

| | | |
|---|---|---|
| EP | 0 810 205 A | 12/1997 |
| EP | 1 219 609 A | 7/2002 |
| WO | WO 9426709 | 11/1994 |
| WO | WO 98/39300 | 9/1998 |
| WO | WO 9933460 | 7/1999 |
| WO | WO 9943663 | 9/1999 |
| WO | WO 00/27819 | 5/2000 |
| WO | WO 0110842 | 2/2001 |
| WO | WO 01/64639 A | 9/2001 |
| WO | WO 02062766 | 8/2002 |

OTHER PUBLICATIONS

Ried et al, "Synthesis of New Potentially Analgesic and Antibiotic Pyridazino '4, 3-e! Oxazinones and Pyrimido '4, 5-c! Pyridazinones" Archiv Der Pharmazie (Weinheim, Germany), 321(9), 527-32, 1988.

International Search Report of PCT/US03/38369 (Sep. 13, 2004).

Vigne et al., "Structure-Activity Relationships of Amiloride and Certain of Its Analogs in Relation to the Blockade of the Sodium/Hydrogen Ion Exchange System", *Molecular Pharmacology*, 1984, 25(1), 131-136.

\* cited by examiner

MODULATORS OF MELANOCORTIN RECEPTOR

CROSS-REFERENCE TO RELATED APPLICATIONS

This application is a continuation of U.S. application Ser. No. 10/727,997, filed Dec. 4, 2003, now U.S. Pat. No. 7,365,070, which claims priority benefit of U.S. Provisional Application No. 60/430,789, filed Dec. 4, 2002, each of which is incorporated herein by reference in its entirety.

TECHNICAL FIELD

This invention relates to compounds that are modulators of melanocortin receptors, especially melanocortin-4-receptor, MC4-R. The invention also provides pharmaceutical compositions comprising the compounds and methods of utilizing those compositions in the treatment and prevention of various MC4-R associated disorders, such as involuntary weight loss.

BACKGROUND OF THE INVENTION

Melanocortins, peptide products resulting from post-translational processing of pro-opiomelanocortin (POMC), are known to have a broad array of physiological activities, including affects on behavior, learning, memory, control of the cardiovascular system, analgesia, thermoregulation, and the release of other neurohumoral agents including prolactin, luetinizing hormone, and biogenic amines (De Weid et al. *Methods Achiev. Exp. Pathol.* (1991) 15:167-199; De Weid et al. *Physiol. Rev.* (1982) 62:977-1059; Gruber, K. A. et al. *Am. J. Physiol.* (1989) 257:R681-R694; Murphy et al. *Science* (1980) 210:1247-1249; Murphy et al. *Science* (1983) 221: 192-193; Ellerkmann, E. et al. *Endocrinol.* (1992) 130:133-138; Versteeg, D. H. G. et al. *Life Sci.* (1986) 835-840). Natural melanocortins include the different types of melanocyte stimulating hormone (a-MSH, P-MSH, y-MSH) and ACTH. Of these, a-MSH and ACTH are considered to be the main endogenous melanocortins. Physiological effects of melanocortins are mediated through the melanocortin receptors (MC-Rs), a subfamily of seven-transmembrane G-protein coupled receptors. Five different receptor subtypes (MC1-R to MC5-R) have been identified to date. While other receptor family members are expressed in various peripheral tissues, MC3-R and MC4-R are localized predominantly in the CNS and brain.

The melanocortin-4 receptor (MC4-R) was identified as a melanocortin receptor subtype which may participate in various physiological functions, including modulating the flow of visual and sensory information, coordinating aspects of somatomotor control, and/or participating in the modulation of autonomic outflow to the heart. K. G. Mountloy et al, *Science,* 257.1248-125 (1992). Significantly, inactivation of this receptor by gene targeting has resulted in mice that develop a maturity onset obesity syndrome associated with hyperphagia, hyperinsulinemia, and hyperglycernia. D. Huszar et al., *Cell,* 88: 131-41 (1997). Additional studies have further supported a role for MC4-R in metabolic regulation: MC4-R is located throughout the brain, primarily in the satiety control regions of the hypothalamus; satiety and energy homeostasis have been shown to be regulated by MC4-R; and agonism of MC4-R leads to decreased food intake and lower body weight. Pritchard, L E et al *Endocrin* 172: 411-412 (2002); Cummings, D E and Schwartz, M W *Nature Genetics* 26:8-9 (2000); and Harrold, J A et al *Diabetes* 48: 267-271 (1999). Still further support of a role in weight regulation is provided in recent studies demonstrating that antagonism of MC4-R leads to increased feeding and weight gain, and MC4-R knockout mice resist cachexia induced by tumor growth Wisse, B E et al *Endocrinology* 142: 3292-3301 (2001); and Marks, D L et al *Cancer research* 61: 1432-1438 (2001).

MC4-R has also been implicated in processes involved in additional disease states, including cardiovascular disorders, neuronal injuries or disorders, inflammation, fever, erectile disorders, and sexual behavior disorders. M. E. Hadley and C. Haskell-Luevano, *Ann. N.Y. Acad. Sci.,* 885:1 (1999); Vrinten D H, et al. *J Neurosci,* 20:8131-7 (2000); Dunbar J C, and Lu H, *Peptides,* 21:211-7 (2000); Huang Q H, et al. *Am J Physiol* 276:R864-71 (1999); and Van der Ploeg L H, et al. *Proc Natl Acad Sci USA* 99:11381-6 (2002).

DESCRIPTION OF THE INVENTION

This invention provides compounds and methods for modulation of melanocortin receptors and melanocortin receptor associated disorders. One embodiment of the invention includes compounds and methods useful for modulation of the MC4-R receptor, including treatment of MC4-R associated disorders (e.g., cachexia and other weight loss disorders, such as those resulting from cancer, HIV, old age and anorexia nervosa).

The compounds, which are modulators of melanocortin receptors, including the MC4-R receptor, are represented by formula I:

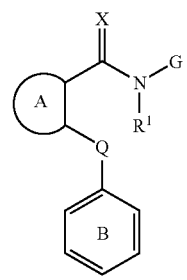

I or a pharmaceutically acceptable salt thereof, wherein:
X is oxygen or sulfur;
G is G1, G2 or G3:

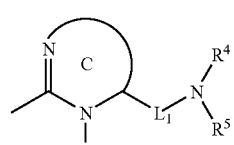

G1

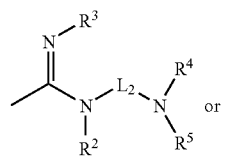

G2

-continued

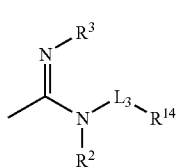
G3

Ring C of G1 is an optionally substituted 5-6 membered aromatic or non-aromatic ring having two or three ring nitrogens;

$L_1$ is a $C_{1-6}$ alkylidene chain optionally substituted by 1-3 $R^6$, wherein the alkylidene chain is optionally interrupted by —C($R^{11}$)$_2$—, —C($R^{11}$)$_2$C($R^{11}$)$_2$—, —C($R^{11}$)=C($R^{11}$)—, —C≡C—, —O—, —S—, —N($R^{11}$), —N($R^{10}$)CO—, —N($R^{11}$)CO$_2$—, —CON($R^{10}$)—, —C($R^{11}$)(OR$^1$)—, —CO—, —CO$_2$—, —OC(=O), —OC(=O)N($R^{10}$)—, —SO—, —SO$_2$—, —N($R^{10}$)SO$_2$—, or —SO$_2$N($R^{10}$)—, and wherein $L_1$ or a portion thereof optionally forms part of a 3-7 membered ring;

$L_2$ is a $C_{2-6}$ alkylidene chain optionally substituted by 1-3 $R^6$, wherein the alkylidene chain is optionally interrupted by —C($R^{11}$)$_2$—, —C($R^{11}$)$_2$C($R^{11}$)$_2$—, —C($R^{11}$)=C($R^{11}$)—, —C≡C—, —O—, —S—, —N($R^1$)$_2$—, —N($R^{10}$)CO—, —N($R^{10}$)CO$_2$—, —CON($R^{10}$)—, —C($R^{11}$)(OR$^1$)—, —CO—, —CO$_2$—, —OC(=O), —OC(=O)N($R^{10}$)—, —SO—, —SO$_2$—, —N($R^{10}$)SO$_2$—, or —SO$_2$N($R^{10}$)—, and wherein $L_2$ or a portion thereof optionally forms part of a 3-7 membered ring;

$L_3$ is a direct link, a $C_{1-6}$ alkylidene chain optionally substituted by 1-3 $R^6$, wherein the alkylidene chain is optionally interrupted by —C($R^{11}$)$_2$—, —C($R^{11}$)$_2$C($R^{11}$)$_2$—, —C($R^{11}$)=C($R^{11}$)—, —C≡C—, —O—, —S—, —N($R^{11}$), —N($R^{10}$)CO—, —N($R^{10}$)CO$_2$—, —CON($R^{10}$)—, —C($R^{11}$)(OR$^1$)—, —CO—, —CO$_2$—, —OC(=O)—, —OC(=O)N($R^{10}$)—, —SO—, —SO$_2$—, —N($R^{10}$)SO$_2$—, or —SO$_2$N($R^{10}$)—, and wherein $L_3$ or a portion thereof optionally forms part of a 3-7 membered ring;

$R^1$ is hydrogen or $C_{1-6}$ aliphatic;

each $R^2$ is independently selected from hydrogen, $C_{1-8}$ aliphatic, $C_{6-10}$ aryl, $C_{7-10}$ aralkyl, or, when Ring C is a 6-membered aromatic ring $R^2$ is a lone electron pair;

$R^3$ is hydrogen, $C_{1-8}$ aliphatic, $C_{6-10}$ aryl, or $C_{7-10}$ aralkyl;

$R^4$ is hydrogen, $C_{1-8}$ aliphatic, C(=O)($C_{1-8}$ aliphatic), CO$_2$($C_{1-8}$ aliphatic), C(=O)N($R^{10}$)($C_{1-7}$ aliphatic), $C_{6-10}$ aryl, heteroaryl, $C_{7-12}$ aralkyl, or heteroaralkyl;

$R^5$ is hydrogen or $C_{1-8}$ aliphatic, or $R^4$ and $R^5$ taken together with their intervening nitrogen form a substituted or unsubstituted, aromatic or non-aromatic, 4-14 membered monocyclic, bicyclic or tricyclic ring system having, in addition to said intervening nitrogen, 0-4 ring heteroatoms selected from nitrogen, sulfur or oxygen;

Ring A is a 5-membered heteroaryl ring or a 6-membered aromatic ring having 0-2 ring nitrogen atoms, wherein Q and C(=X)N(R$^1$)-G are attached at ortho positions on Ring A and wherein Ring A is optionally substituted by one to three $R^7$;

Ring B is a 6-membered aromatic ring having 0-2 ring nitrogen atoms, wherein Ring B is optionally substituted by one or more $R^8$;

Q is a $C_2$-$C_4$ alkylidene chain optionally substituted by one to three $R^9$, wherein a methylene unit of the alkylidene chain is optionally replaced by —S—, —S(O)—, —SO$_2$—, —N(R$^1$)—, —O—, —C(O)—, or —C(S)—;

each $R^6$ is independently selected from halo, —OR$^1$, —CN, —$C_{1-6}$ aliphatic, —N($R^{10}$)$_2$, —C=O($C_{1-5}$ aliphatic), —CO$_2$R$^1$, —CH$_2$CO$_2$R$^1$, or —C(=O)N($R^{10}$)($C_{1-5}$ aliphatic);

each $R^7$ is independently selected from -halo, —NO$_2$, —CN, or a substituted or unsubstituted group selected from —R$^{12}$, —OR$^1$, —SR$^{12}$, —$C_{6-10}$ aryl, -heterocyclyl, -heteroaryl, —($C_{6-10}$ aryl)alkyl, -(heterocyclyl)alkyl, -(heteroaryl)alkyl, —N($R^{10}$)$_2$, —NR$^{10}$C(O)R$^1$, —NR$^{10}$C(O)N($R^{10}$)$_2$, —NR$^{10}$CO$_2$R$^{12}$, —CO$_2$R$^1$, —C(O)R$^1$, —C(O)N($R^{10}$)$_2$, —OC(O)N($R^{10}$)$_2$, —S(O)$_2$R$^{12}$, —SO$_2$N($R^{10}$)$_2$, —S(O)R$^{12}$, —NR$^{10}$SO$_2$N($R^{10}$)$_2$, —NR$^{10}$SO$_2$R$^{12}$, or —C(=NH)—N($R^{10}$)$_2$, or two adjacent $R^7$ taken together with their intervening atoms form a 5-6 membered unsaturated or partially unsaturated ring having 0-2 ring heteroatoms selected from nitrogen, oxygen or sulfur;

each $R^8$ is independently selected from -halo, —NO$_2$, —CN, or a substituted or unsubstituted group selected from —R$^{12}$, —OR$^1$, —SR$^{12}$, —$C_{6-10}$ aryl, -heterocyclyl, -heteroaryl, —($C_{6-10}$ aryl)alkyl, -(heterocyclyl)alkyl, -(heteroaryl)alkyl, —N($R^{10}$)$_2$, —NR$^{10}$C(O)R$^1$, —NR$^{10}$C(O)N($R^{10}$)$_2$, —NR$^{10}$CO$_2$R$^{12}$, —CO$_2$R$^1$, —C(O)R$^1$, —C(O)N($R^{10}$)$_2$, —OC(O)N($R^{10}$)$_2$, —S(O)$_2$R$^{12}$, —SO$_2$N($R^{10}$,)$_2$, —S(O)R$^{12}$, —NR$^{10}$SO$_2$N($R^{10}$)$_2$, —NR$^{10}$SO$_2$R$^{12}$, or —C(=NH)—N($R^{10}$)$_2$, or two adjacent $R^8$ taken together with their intervening atoms form a 5-6 membered unsaturated or partially unsaturated ring having 0-2 ring heteroatoms selected from nitrogen, oxygen or sulfur;

each $R^9$ is independently selected from halo, OR$^1$, CN, $C_{1-6}$ aliphatic, N($R^{10}$)$_2$, C=O($C_{1-5}$ aliphatic), CO$_2$($C_{1-5}$ aliphatic), or C(=O)N($R^{10}$)($C_{1-5}$ aliphatic), or $R^9$ and an $R^7$, at a position ortho to Q, are taken together with their intervening atoms form a 5-7 membered unsaturated or partially unsaturated ring having 0-2 ring heteroatoms selected from N, O or S;

each $R^{10}$ is independently selected from hydrogen, a substituted or unsubstituted $C_{1-8}$ aliphatic group, C(=O)R$^1$, CO$_2$R$^1$, SO$_2$R$^1$, or two $R^{10}$ on the same nitrogen taken together with the nitrogen form a 5-8 membered aromatic or non-aromatic ring having, in addition to the nitrogen, 0-2 ring heteroatoms selected from N, O, or S;

each $R^{11}$ is independently selected from hydrogen, CO$_2$R$^{12}$, CON($R^{12}$)$_2$, OR$^{12}$, or a substituted or unsubstituted $C_{1-8}$ aliphatic group;

each $R^{12}$ is independently selected from a substituted or unsubstituted $C_{1-8}$ aliphatic group; and $R^{14}$ is hydrogen, $C_{1-8}$ aliphatic, $C_{6-10}$ aryl, heteroaryl, $C_{7-12}$ aralkyl, heteroaralkyl, heterocyclyl, or $R^3$ and $R^{14}$ taken together with their intervening nitrogens form a substituted or unsubstituted, aromatic or non-aromatic, 4-14 membered monocyclic, bicyclic or tricyclic ring system having, in addition to said intervening nitrogen, 0-4 ring heteroatoms selected from nitrogen, sulfur or oxygen. Preferably $R^{14}$ is a 5-6 membered heterocyclic ring having a ring nitrogen and 0-1 additional ring heteroatoms selected from N, O or S. In another embodiment, $R^3$ and $R^{14}$ of G3. optionally form a ring.

The term "aliphatic" as used herein means straight-chain, branched or cyclic C1-C12 hydrocarbons which are completely saturated or which contain one or more units of unsaturation but which are not aromatic. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl. The terms "alkyl", "alkoxy", "hydroxyalkyl", "alkoxyalkyl", and "alkoxycarbonyl", used alone or as part of a larger moiety include both straight and branched chains containing one to twelve carbon atoms. The terms "alkenyl." and "alkynyl" used alone or as part of a larger moiety include both straight and branched chains containing two to twelve carbon atoms. The term "cycloalkyl" used alone or as part of a larger moiety include cyclic $C_3$-$C_{12}$ hydrocarbons which are completely saturated or which contain one or more units of unsaturation, but which are not aromatic. The term "alkoxy" refers to an —O-alkyl radical.

The terms "haloalkyl", "haloalkenyl" and "haloalkoxy" mean alkyl, alkenyl or alkoxy, as the case may be, substituted with one or more halogen atoms. The term "halogen" or "halo" means F, Cl, Br, or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR+ (as in N-substituted pyrrolidinyl).

The term "carbocycle", "carbocyclyl", "carbocyclo", or "carbocyclic" as used herein means an aliphatic ring system having three to fourteen members. The term "carbocycle", "carbocyclyl", "carbocyclo", or "carbocyclic" whether saturated or partially saturated, also refers to rings that are optionally substituted. The term "carbocycle", "carbocyclyl", "carbocyclo", or "carbocyclic" also includes aliphatic rings that are fused to one or more aromatic or nonaromatic rings, such as in a decahydronaphthyl or tetrahydronaphthyl, where the radical or point of attachment is on the aliphatic ring.

The term "aryl" used alone or as part of a larger moiety as in "aralkyl", "aralkoxy", or "aryloxyalkyl", refers to mono-, bi-, or tricyclic aromatic hydrocarbon ring systems having five to fourteen members, such as phenyl, benzyl, phenethyl, 1-naphthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenanthridinyl; or tetrahydronaphthyl, where the radical or point of attachment is on the aromatic ring. The term "aralkyl" refers to an alkyl group substituted by an aryl. Examples of aralkyl groups include, but are not limited to, benzyl and phenethyl.

The term "heterocycle", "heterocyclyl", or "heterocyclic" unless otherwise indicated includes non-aromatic ring systems having five to fourteen members, preferably five to ten, in which one or more ring carbons, preferably one to four, are each replaced by a heteroatom such as N, O, or S. Examples of heterocyclic rings include 3-1H-benzimidazol-2-one, (1-substituted)-2-oxo-benzimidazol-3-yl, 2-tetrahydrofuranyl, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted. The term "heterocyclylalkyl" refers to an alkyl group substituted by a heterocyclyl.

The term "heteroaryl", used alone or as part of a larger moiety as in "heteroaralkyl" or "heteroarylalkoxy", refers to heteroaromatic ring groups having five to fourteen members, preferably five to ten, in which one or more ring carbons, preferably one to four, are each replaced by a heteroatom such as N, O, or S. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroaromatic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic". The term "heteroaralkyl" refers to an alkyl group substituted by a heteroaryl.

The term "linker group" or "linker" means an organic moiety that connects two parts of a compound. Linkers are typically comprised of an atom such as oxygen or sulfur, a unit such as —NH—, —CH$_2$—, —C(O)—, —C(O)NH—, or a chain of atoms, such as an alkylidene chain. The molecular mass of a linker is typically in the range of about 14 to 200, preferably in the range of 14 to 96 with a length of up to about six atoms. Examples of linkers include a saturated or unsaturated $C_{1-6}$ alkylidene chain which is optionally substituted, and wherein one or two saturated carbons of the chain are optionally replaced by —C(O)—, —C(O)C(O)—, —CONH—, —CONHNH—, —CO$_2$—, —OC(O)—, —NHCO$_2$—, —O—, —NHCONH—, —OC(O)NH—, —NHNH—, —NHCO—, —S—, —SO—, —SO$_2$—, —NH—, —SO$_2$NH—, or —NHSO$_2$—.

The term "alkylidene chain" refers to an optionally substituted, straight or branched carbon chain that may be fully saturated or have one or more units of unsaturation. The optional substituents are as described above for an aliphatic group. Alkylidene chain used herein include alkylidene chains containing 0-4 fluorine substituents.

An aryl (including the aryl moiety in aralkyl, aralkoxy, aryloxyalkyl and the like) or heteroaryl (including the heteroaryl moiety in heteroaralkyl and heteroarylalkoxy and the like) group may contain one or more substituents. Examples of suitable substituents on the unsaturated carbon atom of an aryl or heteroaryl group include a halogen, —R*, —OR*, —SR*, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), —NO2, —CN, —N(R*)$_2$, —NR*C(O)R*, —NR*C(O)N(R*)$_2$, —NR*CO$_2$R*, —NR*NR*C(O)R*, —NR*NR*C(O)N(R*)$_2$, —NR*NR*CO$_2$R*, —C(O)C(O)R*, —C(O)CH$_2$C(O)R*, —CO$_2$R*, —C(O)R*, —C(O)N(R*)$_2$, —OC(O)N(R*)$_2$, —S(O)$_2$R*, —SO$_2$N(R*)$_2$, —S(O)R*, —NR*SO$_2$N(R*)$_2$, —NR*SO$_2$R*, —C(=S)N(R*)$_2$, —C(=NH)—N(R*)$_2$, —(CH$_2$)$_y$NHC(O)R*, —(CH$_2$)$_y$NHC(O)CH(Y—R*)(R*); wherein each R* is independently selected from hydrogen, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph); y is 0-6; and Y is a linker group. Examples of substituents on the aliphatic group or the phenyl ring of R* include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

An aliphatic group or a non-aromatic heterocyclic ring may contain one or more substituents. Unless otherwise indicated, the term "aliphatic" means substituted or unsubstituted aliphatic groups. Examples of suitable substituents on the saturated carbon of an aliphatic group or of a non-aromatic heterocyclic ring include those listed above for the unsaturated carbon of an aryl or heteroaryl group and the following: =O, =S, =NNHR*, =NN(R*)$_2$, =N—, =NNHC(O)R*, =NNHCO$_2$(alkyl), =NNHSO$_2$(alkyl), or =NR*, where each R* is independently selected from hydrogen, an unsubstituted aliphatic group or a substituted aliphatic group. Examples of substituents on the aliphatic group include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl. Preferred halogen substitutions on an aliphatic group are fluorine. Aliphatic groups used herein can include aliphatic groups containing 0-4 fluorine substituents.

Suitable substituents on the nitrogen of a non-aromatic heterocyclic ring include —R$^+$, —N(R$^+$)$_2$, —C(O)R$^+$, —CO$_2$R$^+$, —C(O)C(O)R$^+$, —C(O)CH$_2$C(O)R$^+$, —SO$_2$R$^+$, —SO$_2$N(R$^+$)$_2$, —C(=S)N(R$^+$)$_2$, —C(=NH)—N(R$^+$)$_2$, and —NR+SO$_2$R$^+$; wherein each R$^+$ is independently selected from hydrogen, an unsubstituted aliphatic group, a substituted aliphatic group, phenyl (Ph), substituted Ph, —O(Ph), substituted —O(Ph), CH$_2$(Ph), substituted CH$_2$(Ph), or an unsubstituted heteroaryl or heterocyclic ring. Examples of substituents on the aliphatic group or the phenyl ring include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

A combination of substituents or variables is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week or, a compound which maintains its integrity long enough to be useful for therapeutic or prophylactic administration to a patient.

It will be apparent to one skilled in the art that certain compounds of this invention may exist in tautomeric forms, all such tautomeric forms of the compounds being within the scope of the invention. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention. Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of this invention.

The present compounds contain an acylguanidine moiety or an acylguanidine-like moiety that may be constrained in a ring system or may be an open chain as shown below in formulae I-A, I-B, and I-C.

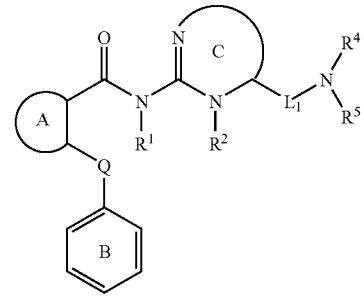

I-A

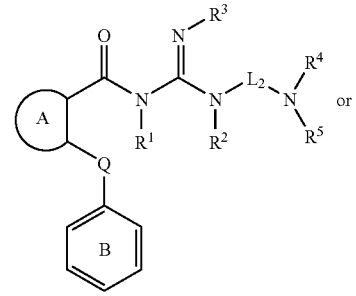

I-B

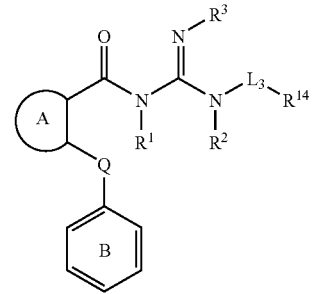

I-C

The Ring C moiety in I-A is an optionally substituted 5-6 membered aromatic or non-aromatic ring. Examples of Ring C include those shown in Table 1 below.

TABLE 1

Examples of Ring C

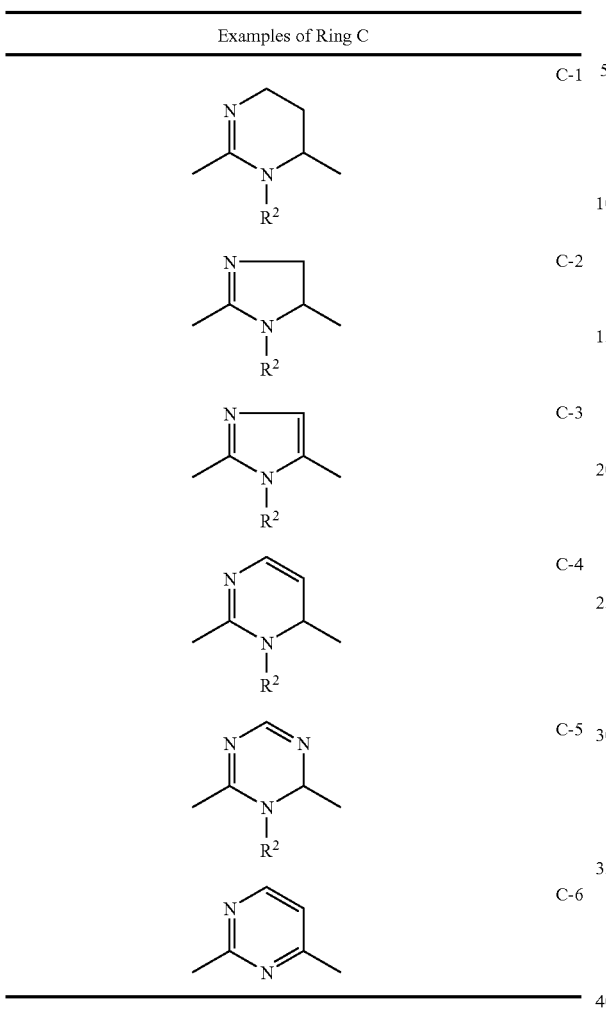

Preferred Ring C moieties are rings C-1 and C-2 shown in Table 1. Ring C may be substituted or unsubstituted. Suitable Ring C substituents, designated as $R^{13}$, include hydrogen, $C_{1-6}$ aliphatic, or a substituent selected from the group consisting of $COR^1$, $CO_2R^1$, CN, —$N(R_{10})_2$, $CON(R^{10})_2$, —$OR^1$, $C_{6-10}$ aryl, $C_{7-12}$ aralkyl, $C_{5-10}$ heteroaryl, $C_{5-10}$ heterocyclyl, $C_{6-12}$ heterocyclylalkyl, and $C_{6-12}$ heteroaralkyl. Alternatively, two $R^{13}$ on the same carbon taken together form =O, or two $R^{13}$ taken together with their intervening atoms form a 3-7 membered ring having 0-2 ring heteroatoms. Preferably, Ring C is unsubstituted or substituted with $C_{1-4}$ alkyl.

When $R^1$ and/or $R^2$ are hydrogen, the present compounds may exist in various tautomeric forms as shown in Eq. 1 below. The depiction or description (including in the claims) of any particular tautomer is understood to include all tautomeric forms of the structure.

One embodiment of this invention relates to compounds of formula I-A wherein $R^1$ and $R^2$ are each hydrogen, as shown by formula I-A-a.

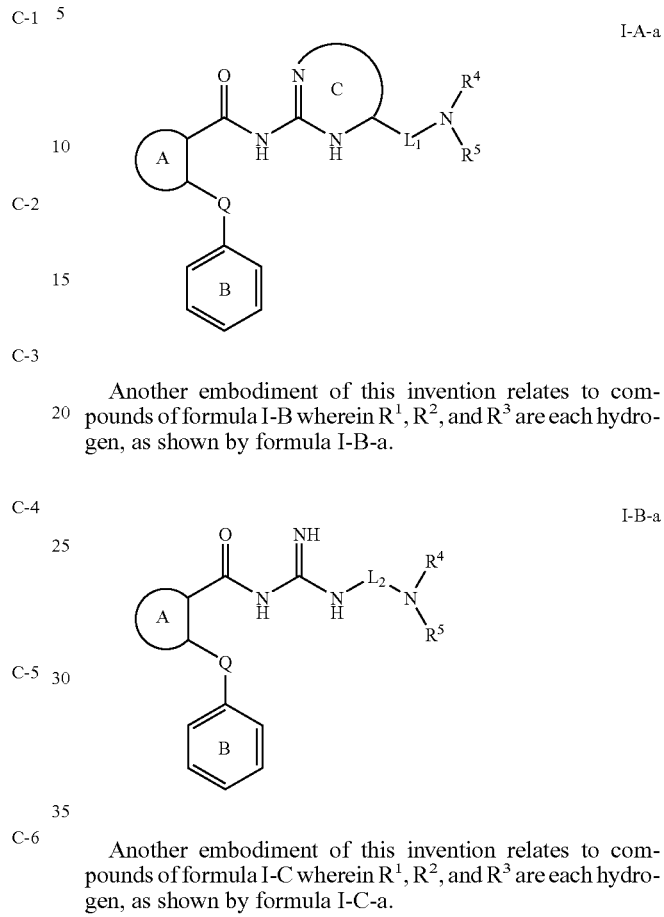

Another embodiment of this invention relates to compounds of formula I-B wherein $R^1$, $R^2$, and $R^3$ are each hydrogen, as shown by formula I-B-a.

Another embodiment of this invention relates to compounds of formula I-C wherein $R^1$, $R^2$, and $R^3$ are each hydrogen, as shown by formula I-C-a.

In one aspect, $R^4$ and $R^5$ groups are $C_{1-8}$ aliphatic groups that are independently selected. More preferred $R^4$ and $R^5$ groups are $C_{1-4}$ aliphatic groups that are independently selected. $R^4$ and $R^5$ may also be taken together with their

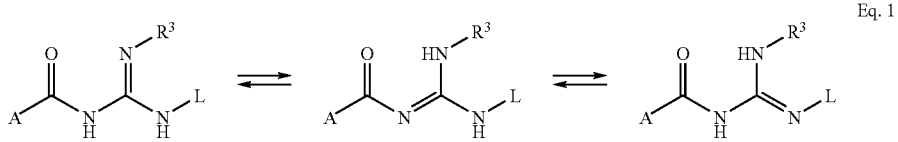

Eq. 1 intervening nitrogen to form a substituted or unsubstituted, aromatic or non-aromatic, 4-14 membered monocyclic, bicyclic or tricyclic ring system having, in addition to said intervening nitrogen, 0-4 ring heteroatoms selected from nitrogen, sulfur or oxygen. Examples of such $R^4/R^5$ rings include piperidinyl, piperazinyl, morpholinyl, pyrrolidinyl, imidazolyl, pyrrolyl, indolyl, purinyl, indazolyl, carbazolyl, and benzimidazolyl. When taken together, $R^4$ and $R^5$ preferably form a 5-6 membered ring, having in addition to said intervening nitrogen, 0-1 ring heteroatoms selected from nitrogen, sulfur or oxygen. Examples of such preferred $R^4/R^5$ rings include piperidinyl, piperazinyl, morpholinyl, pyrrolidinyl, imidazolyl, and pyrrolyl. In another aspect, $R^4$ is a $C_{1-4}$ aliphatic group and $R^5$ is aryl, aralkyl, heteroaryl, or heteroaralkyl.

$L_1$ and $L_2$ are linker groups that separate the acylguanidine moiety from the basic nitrogen bearing the $R^4$ and $R^5$ groups. The distance between the guanidinyl nitrogen bearing $R^2$ and the basic —$N(R^4)(R^5)$ may be approximately the length of a 2-6 linear carbon chain or between about 300 to 900 picometers (pm). Preferably the distance is that of a 2-4 carbon chain, more preferably a 3-4 carbon chain and most preferably a 3 carbon chain. The optimal distance between —$N(R^2)$— and —$N(R^4)(R^5)$— may also be obtained by replacing one or more methylene units of an alkylidene linker with other groups such as —O—, —S—, —$N(R^{10})CO$—, —$N(R^{10})CO_2$—, —$CON(R^{10})$—, —CO—, —$CO_2$—, —OC(=O), —$OC(=O)N(R^{10})$—, —$SO_2$—, —$N(R^{10})SO_2$—, or —$SO_2N(R^{11})$— where $R^{10}$ is as described above. Alternatively, the alkylidene chain may constrained as part of a 3-7 membered ring. One skilled in the art will be able to select a suitable $L_1$ or $L_2$ linker by reference to the known bond distances of various atom pairs and/or ring systems in light of the examples presented below. The $L_3$ linker group in compounds of formula I-C is similarly selected.

A preferred $L_1$ is a $C_{2-3}$ alkylidene chain such as —$CH_2CH_2$— or —$CH_2CH_2CH_2$—. A preferred $L_2$ is a $C_{3-4}$ alkylidene chain such as —$CH_2CH_2CH_2$—, —$CH_2CH_2CH_2CH_2$—, —$CH(CH_3)CH_2CH_2$—, or —$CH(CH_3)CH_2CH_2$—.

Ring A is preferably a phenyl ring or a 5-membered heteroaryl ring. A preferred heteroaryl ring is thienyl.

$R^7$, when present, is preferably selected from -halo, —CN, —$R^{12}$, —$OR^1$, or —$C(O)R^1$, wherein $R^1$ and $R^{12}$ are preferably $C_{1-4}$ alkyl. A preferred $R^7$ halo group is fluoro.

Q is a linker group that separates Ring A and Ring B. A suitable Q linker provides a distance between the rings of about 280 to 600 pm. A preferred Q is a $C_2$ alkylidene chain such as —$CH_2CH_2$—. Alternatively, Q may form part of a ring fused to Ring A as shown below.

Ring B is preferably a phenyl or naphthyl ring. Ring B may have 0-4 $R^8$ groups. When Ring B is a phenyl ring, it is preferably substituted by $R^8$ at the 2-position and/or 5-position of Ring B relative to the ring carbon bearing Q. Most preferably, Ring B is substituted at the 2- and 5-positions. Examples of preferred $R^8$ groups include halo, $C_{1-4}$ alkyl, $C_{1-3}$ alkoxy, $CO(C_{1-3}$ alkyl), $CONH(C_{1-3}$ alkyl), $SO_2(C_{1-3}$ alkyl), or $SO_2NH(C_{1-3}$ alkyl). When Ring B is a naphthyl ring, it is preferably attached to Q at the α-position of the naphthyl ring. Adjacent $R^8$ on Ring B may be taken together to form a fused ring system. In one aspect, the fused Ring B system is a benzofuranyl ring. The fused ring B system may be substituted by $R^8$ on either of the two fused rings.

Unless otherwise specified, when an $R^4$, $R^7$, $R^8$ or $R^{14}$ substituent has a heterocyclyl moiety, the ring size may be from 3 to 10 ring atoms, preferably from 3 to 6 and most preferably from 5 to 6. When the substituent has a heteroaryl moiety, a preferred ring size is five or six. When the substituent is heterocylylalkyl or heteroalkyl, the alkyl moiety is preferably from one to three carbons.

When G of formula I is G1, a preferred embodiment of this invention relates to a compound having one or more of the following features.
(a) X is oxygen.
(b) $L_1$ is a $C_{2-3}$ alkylidene chain.
(c) Q is —$CH_2CH_2$—.
(d) G1 is G1-a or G1-b:

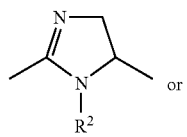

G1-a

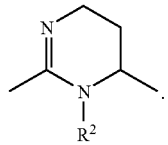

G1-b (e) $R^4$ and $R^5$ are each independently selected from a $C_{1-4}$ aliphatic group or $R^4$ and $R^5$ taken together with their intervening nitrogen form a 5-6 membered ring.
(f) Ring A is an optionally substituted phenyl or thienyl.
(g) Ring B is a substituted phenyl or naphthyl. In a more preferred aspect of this embodiment the compound has all of the above features (a)-(g).

When G of formula I is G1, a more preferred embodiment of this invention relates to a compound having one or more of the following features.
(a) X is oxygen.
(b) $L_1$ is —$CH_2CH_2$— or —$CH_2CH_2CH_2$—.
(c) Q is —$CH_2CH_2$—.
(d) G1 is G1-a or G1-b:

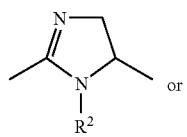

G1-a

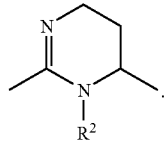

G1-b (e) $R^4$ and $R^5$ are each independently selected from a $C_{1-3}$ aliphatic group or $R^4$ and $R^5$ taken together with their intervening nitrogen form a piperidinyl, pyrrolidinyl, piperazinyl or morpholinyl ring.
(f) Ring A is an optionally substituted phenyl or thienyl.
(g) Ring B is a substituted phenyl or naphthyl. In a preferred aspect of this embodiment the compound has all of the above features (a)-(g).

When G of formula I is G2, a preferred embodiment of this invention relates to a compound having one or more of the following features.
(a) X is oxygen.
(b) $L_2$ is a $C_{3-4}$ alkylidene chain.
(c) Q is —$CH_2CH_2$—.
(d) (i) $R^4$ and $R^5$ are each independently selected from a $C_{1-4}$ aliphatic group, or (ii) $R^4$ and $R^5$ taken together with their intervening nitrogen form a 5-6 membered ring, or (iii) $R^4$ is a $C_{1-4}$ aliphatic group and $R^5$ is aryl, aralkyl, heteroaryl, or heteroaralkyl.

(e) Ring A is an optionally substituted phenyl or thienyl.

(f) Ring B is a substituted phenyl or naphthyl. In a preferred aspect of this embodiment the compound has all of the above features (a)-(f).

When G of formula I is G2, a more preferred embodiment of this invention relates to a compound having the following features.

(a) X is oxygen.

(b) $L_2$ is —$CH_2CH_2CH_2$— or —$CH(CH_3)CH_2CH_2$—.

(c) Q is —$CH_2CH_2$—.

(d) (i) $R^4$ and $R^5$ are each independently selected from a $C_{1-4}$ aliphatic group, or (ii) $R^4$ and $R^5$ taken together with their intervening nitrogen form a 5-6 membered ring, or (iii) $R^4$ is a $C_{1-4}$ aliphatic group and $R^5$ is aryl, aralkyl, heteroaryl, or heteroaralkyl. In one aspect, $R^4$ and $R^5$ are taken together with their intervening nitrogen form a piperidinyl, pyrrolidinyl, piperazinyl or morpholinyl ring.

(e) Ring A is an optionally substituted phenyl or thienyl.

(f) Ring B is a substituted phenyl or naphthyl. In a preferred aspect of this embodiment the compound has all of the above features (a)-(f).

When G of formula I is G3, a preferred embodiment of this invention relates to a compound having one or more of the following features.

(a) X is oxygen.

(b) $L_3$ is a direct link, —$CH_2$—, —$CH(R^6)$—, —$CH_2CH_2$—, —$CH_2CH_2CH_2$—, or —$CH_2CH_2CH_2CH_2$—. In one aspect, $L_3$ is a direct link, —$CH_2$—, —$CH(R^6)$—, or —$CH_2CH_2$—. In another aspect, $L_3$ is —$CH_2$— or —$CH(R^6)$—.

(c) Q is —$CH_2CH_2$—.

(d) $R^6$ is $C_{1-3}$ alkyl, $CO_2H$, $CO_2(C_{1-6}$ alkyl$)$, $CH_2CO_2H$, or $CH_2CO_2(C_{1-6}$ alkyl$)$. In one aspect, $R^6$ is $CO_2H$ or $CH_2CO_2H$.

(e) $R^{14}$ is a $C_{1-6}$ aliphatic group or a 5-6 membered heterocyclic ring. In one aspect, $R^{14}$ is a 5-6 membered heterocyclic ring.

(f) —Ring A is an optionally substituted phenyl or thienyl.

(g) Ring B is a substituted phenyl or naphthyl. In a preferred aspect of this embodiment the compound has all of the above features (a)-(g).

When G of formula I is G3, a more preferred embodiment of this invention relates to a compound having one or more of the following features.

(a) X is oxygen.

(b) $L_3$ is —$CH_2$—, —$CH(R^6)$—, —$CH_2CH_2CH_2$—, or —$CH_2CH_2CH_2CH_2$—.

(c) $R^6$ is $CO_2H$ or $CH_2CO_2H$.

(d) $R^{14}$ is a 5-6 membered heterocyclic ring having a ring nitrogen and 0-1 additional ring heteroatoms selected from N, O or S.

(e) Q is —$CH_2CH_2$—.

(f) Ring A is an optionally substituted phenyl or thienyl.

(g) Ring B is a substituted phenyl or naphthyl.

In a preferred aspect of this embodiment the compound has all of the above features (a)-(g). In another aspect, $L_3$ is a direct bond to $R^{14}$ or a $C_{1-2}$ alkylidene and $R^{14}$ is a 7-9 membered bicyclo ring system such as an aza-bicyclo[3.2.1]octyl or an aza-bicyclo[3.2.2]nonyl ring system.

The $R^{14}$ group of the G3 moiety may be substituted or unsubstituted. When $R^{14}$ is a 5-6 membered heterocyclic ring, particular examples include piperidinyl, pyrrolidinyl, and piperazinyl. The point of attachment of $R^{14}$ to $L_3$ may be at a ring carbon or nitrogen of $R^{14}$. Suitable substituents on the $R^{14}$ ring include groups represented by T-$R^{15}$ where T is a bond or a $C_{1-4}$ alkylidene chain and $R^{15}$ is —$C_{1-6}$ aliphatic, —$CO_2R^1$, —$OR^1$, -halo, —$N(R^{10})_2$, —$C(O)N(R^{10})_2$, —$N(R^{10})CO_2R^1$, —$N(R^{10})COR^1$, —$COR^1$, 5-6 membered heteroaryl, 5-6 membered heterocyclyl, -phenyl, or —CN.

One embodiment of this invention relates to compounds represented by formulae II-A, II-B, II-C or II-D:

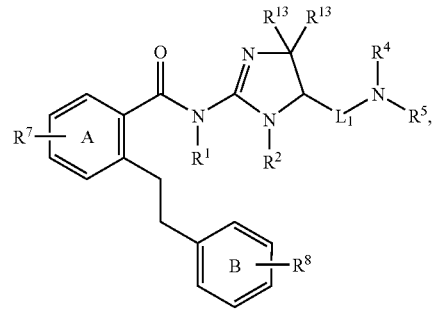

II-A

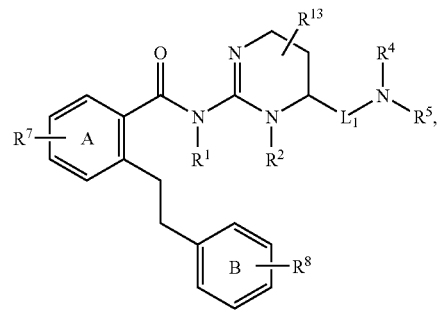

II-B

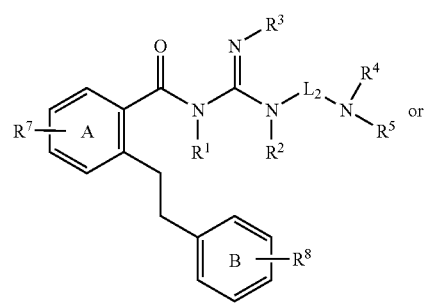

II-C

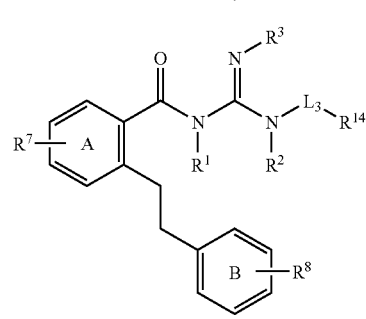

II-D wherein:

$R^1$ and $R^2$ are each hydrogen;

$R^3$ is hydrogen or $R^3$ and $R^{14}$ taken together with their intervening nitrogens form a 4-6 membered ring;

$L_1$ is —$CH_2CH_2$— or —$CH_2CH_2CH_2$—;

$L_2$ is —$CH_2CH_2CH_2$—, —$CH_2CH_2CH_2CH_2$—, —$CH(CH_3)CH_2CH_2$—, or —$CH(CH_3)CH_2CH_2CH_2$—;

$L_3$ is a direct link, —$CH_2$—, or —$CH_2CH_2$—;

$R^7$ is absent or is -halo, —$NO_2$, —CN, —$R^{12}$, —$OR^1$, —$SR^{12}$, —$C_{6-10}$ aryl, -heterocyclyl, -heteroaryl, —($C_{6-10}$ aryl)alkyl, -(heterocyclyl)alkyl, -(heteroaryl)alkyl, —$N(R^{10})_2$, —$NR^{10}C(O)R^1$, —$NR^{10}C(O)N(R^{10})_2$, —$NR^{10}CO_2R^{12}$, —$CO_2R^1$, —$C(O)R^1$, —$C(O)N(R^{10})$, —$OC(O)N(R^{10})_2$, —$S(O)_2R^{12}$, —SO$_2$N(R$^{10}$)$_2$—S(O)R$^{12}$, —NR$^{10}$SO$_2$N(R$^{10}$)$_2$, —NR$^{10}$SO$_2$R$^{12}$, or —C(=NH)—N(R$^{10}$)$_2$, or two adjacent R$^7$ taken together with their intervening atoms form a 5-6 membered unsaturated or partially unsaturated ring having 0-2 heteroatoms selected from nitrogen, oxygen or sulfur;

R$^8$ is -halo, —NO$_2$, —CN, or a substituted or unsubstituted group selected from —R$^{12}$, —OR$^1$, —SR$^{12}$, —C$_{6-10}$ aryl, -heterocyclyl, -heteroaryl, —(C$_{6-10}$ aryl)alkyl, -(heterocyclyl)alkyl, -(heteroaryl)alkyl, —N(R$^{10}$)$_2$, —NR$^{10}$C(O)R$^1$, —NR$^{10}$C(O)N(R$^{10}$)$_2$, —NR$^{10}$CO$_2$R$^{12}$, —C(O)R$^1$—C(O)N(R$^{10}$)$_2$, —OC(O)N(R$^{10}$)$_2$, —S(O)$_2$R$^{12}$, —SO$_2$N(R$^{10}$)$_2$, —S(O)R$^{12}$, —NR$^{10}$SO$_2$N(R$^{10}$)$_2$, —NR$^{10}$SO$_2$R$^{12}$, or —C(=NH)—N(R$^{10}$)$_2$, or two adjacent R$^8$ taken together with their intervening atoms form a 5-6 membered unsaturated or partially unsaturated ring having 0-2 heteroatoms selected from nitrogen, oxygen or sulfur;

R$^4$ and R$^5$ are each independently selected from C$_{1-3}$ alkyl or R$^4$ and R$^5$ taken together with their intervening nitrogen form a 5-6 membered ring;

R$^{14}$ is a C$_{1-6}$ aliphatic; or a 5-6 membered heterocyclic ring having a ring nitrogen and 0-1 additional ring heteroatoms selected from N, O or S; or R$^3$ and R$^{14}$ taken together with their intervening nitrogens form a 4-6 membered ring;

each R$^{13}$ is independently selected from hydrogen, C$_{1-6}$ aliphatic, or a substituent selected from the group consisting of COR$^1$, CO$_2$R$^1$, CN, —N(R$_{10}$)$_2$, CON(R$^{10}$)$_2$, —OR$^1$, or two R$^{13}$ on the same carbon taken together form =O, or two R$^{13}$ taken together with their intervening atoms form a 3-7 membered ring having 0-2 ring heteroatoms;

each R$^{10}$ is independently selected from hydrogen, a substituted or unsubstituted C$_{1-8}$ aliphatic group, C(=O)R$^1$, CO$_2$R$^1$, SO$_2$R$^1$, or two R$^{10}$ on the same nitrogen taken together with the nitrogen form a 5-8 membered aromatic or non-aromatic ring having, in addition to the nitrogen, 0-2 ring heteroatoms selected from N, O, or S;

each R$^{11}$ is independently selected from hydrogen or an optionally substituted C$_{1-8}$ aliphatic group; and each R$^{12}$ is independently selected from a substituted or unsubstituted C$_{1-8}$ aliphatic group.

For compounds of formula II the following are preferred:
R$^1$ and R$^2$ are each hydrogen;
R$^3$ is hydrogen;
L$_1$ is —CH$_2$CH$_2$— or —CH$_2$CH$_2$CH$_2$—;
L$_2$ is —CH$_2$CH$_2$CH$_2$—, —CH$_2$CH$_2$CH$_2$CH$_2$—, —CH(CH$_3$)CH$_2$CH$_2$—, or —CH(CH$_3$)CH$_2$CH$_2$CH$_2$—;
L$_3$ is a direct link, —CH$_2$—, or —CH$_2$CH$_2$—;
R$^7$ is absent or is -halo, —CN, —R$^{12}$—OR$^1$, —SR$^{12}$, —N(R$^{11}$)$_2$, —NR$^{10}$C(O)R$^1$, —NR$^{10}$C(O)N(R$^{10}$)$_2$, —NR$^{10}$CO$_2$R$^{12}$, —CO$_2$R$^1$—C(O)R$^1$—C(O)N(R$^{10}$)$_2$, —OC(O)N(R$^{10}$)$_2$, —S(O)$_2$R$^{12}$, —SO$_2$N(R$^{10}$)$_2$, —S(O)R$^{12}$, —NR$^{10}$SO$_2$N(R$^{10}$)$_2$, or —NR$^{10}$SO$_2$R$^{12}$;
R$^8$ is -halo, —CN, or a substituted or unsubstituted group selected from —R$^{12}$, —OR$^1$, —SR$^{12}$, —N(R$^{10}$)$_2$, —NR$^{10}$C(O)R$^1$, —NR$^{10}$CO$_2$R$^{12}$, —CO$_2$R$^1$, —C(O)R$^1$, —C(O)N(R$^{10}$)$_2$, —OC(O)N(R$^{10}$)$_2$, —S(O)$_2$R$^{12}$, —SO$_2$N(R$^{10}$)$_2$, —S(O)R$^{12}$, —NR$^{10}$SO$_2$N(R$^{10}$)$_2$, or —NR$^1$SO$_2$R$^{12}$, or two adjacent R$^8$ taken together with their intervening atoms form a 5-6 membered unsaturated or partially unsaturated ring having 0-2 heteroatoms selected from nitrogen, oxygen or sulfur;
R$^4$ and R$^5$ are each independently selected from C$_{1-3}$ alkyl or R$^4$ and R$^5$ taken together with their intervening nitrogen form a 5-6 membered ring;
R$^{14}$ is a C$_{1-6}$ aliphatic or a 5-6 membered heterocyclic ring having a ring nitrogen and 0-1 additional ring heteroatoms selected from N, O or S;

each R$^{13}$ is hydrogen;
each R$^{10}$ is hydrogen;
each R$^{11}$ is independently selected from hydrogen or an optionally substituted C$_{1-5}$ aliphatic group; and
each R$^{12}$ is independently selected from a substituted or unsubstituted C$_{1-5}$ aliphatic group.

For compounds of formula II, more preferred are the following:
R$^7$ is absent or is halo;
Ring B is a phenyl ring having two R$^8$ substituents that are para to one another or Ring B is an α-naphthyl ring; and
each R$^8$ is independently selected from halo, C$_{1-4}$ alkyl, C$_{1-3}$ alkoxy, CO(C$_{1-3}$ alkyl), CONH(C$_{1-3}$ alkyl), SO$_2$(C$_{1-3}$ alkyl), or SO$_2$NH(C$_{1-3}$ alkyl).

Another embodiment of this invention relates to compounds represented by formulae III-A, III-B, III-C or III-D:

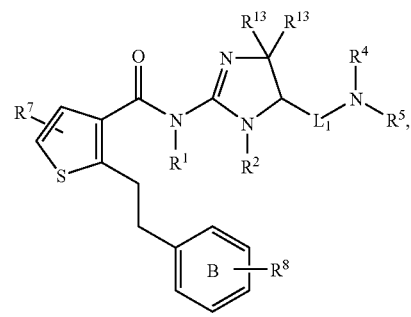

III-A

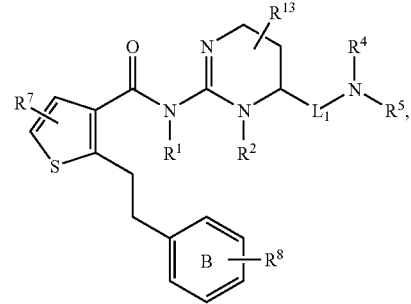

III-B

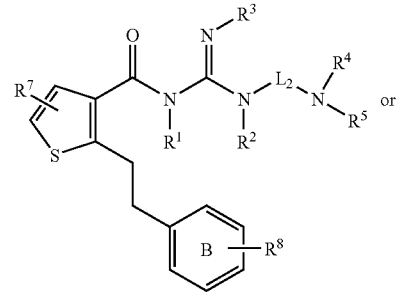

III-C

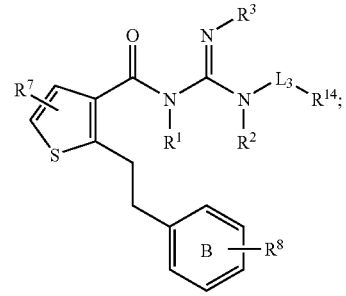

III-D wherein:

$R^1$, and $R^2$ are each hydrogen;

$R^3$ is hydrogen;

$L_1$ is —$CH_2CH_2$— or —$CH_2CH_2CH_2$—;

$L_2$ is —$CH_2CH_2CH_2$—, —$CH_2CH_2CH_2CH_2$—, —$CH(CH_3)CH_2CH_2$—, or —$CH(CH_3)CH_2CH_2CH_2$—;

$L_3$ is a direct link, —$CH_2$—, or —$CH_2CH_2$—;

$R^7$ is absent or is -halo, —$CO_2R^1$, —$C(O)R^1$, —$C(O)N(R^{10})_2$, or two adjacent $R^7$ taken together with their intervening atoms form a 5-6 membered unsaturated or partially unsaturated ring having 0-2 heteroatoms selected from nitrogen, oxygen or sulfur;

$R^8$ is -halo, —$NO_2$, —CN, or a substituted or unsubstituted group selected from —$R^{12}$, —$OR^1$, —$SR^{12}$, —$C_{6-10}$ aryl, -heterocyclyl, -heteroaryl, —($C_{5-10}$ aryl)alkyl, -(heterocyclyl)alkyl, -(heteroaryl)alkyl, —$N(R^{10})_2$, —$NR^{10}C(O)R^1$, —$NR^{10}C(O)N(R^{10})_2$, —$NR^{10}CO_2R^{12}$, —$CO_2R^1$, —$C(O)R^1$, —$C(O)N(R^{10})_2$, —$OC(O)N(R^{10})_2$, —$S(O)_2R^{12}$, —$SO_2N(R^{10})_2$, —$S(O)R^{12}$, —$NR^{10}SO_2N(R^{10})_2$, —$NR^{10}SO_2R^{12}$, or —$C(=NH)$—$N(R^{11})_2$, or two adjacent $R^8$ taken together with their intervening atoms form a 5-6 membered unsaturated or partially unsaturated ring having 0-2 heteroatoms selected from nitrogen, oxygen or sulfur;

$R^4$ and $R^5$ are each independently selected from $C_{1-3}$ alkyl or $R^4$ and $R^5$ taken together with their intervening nitrogen form a 5-6 membered ring;

$R^{14}$ is selected from a $C_{1-6}$ aliphatic or $R^3$ and $R^{14}$ taken together with their intervening nitrogens form a 4-6 membered ring;

each $R^{13}$ is independently selected from hydrogen, $C_{1-6}$ aliphatic, or a substituent selected from the group consisting of $COR^1$, $CO_2R^1$, CN, —$N(R_{10})_2$, $CON(R^{10})_2$, —$OR^1$, or two $R^{13}$ on the same carbon taken together form =O, or two $R^{13}$ taken together with their intervening atoms form a 3-7 membered ring having 0-2 ring heteroatoms;

each $R^{10}$ is independently selected from hydrogen, a substituted or unsubstituted $C_{1-8}$ aliphatic group, C(=O)$R^1$, $CO_2R^1$, $SO_2R^1$, or two $R^{10}$ on the same nitrogen taken together with the nitrogen form a 5-8 membered aromatic or non-aromatic ring having, in addition to the nitrogen, 0-2 ring heteroatoms selected from N, O, or S;

each $R^{11}$ is independently selected from hydrogen or an optionally substituted $C_{1-8}$ aliphatic group;

each $R^{12}$ is independently selected from a substituted or unsubstituted $C_{1-8}$ aliphatic group; and $R^{14}$ is a $C_{1-6}$ aliphatic or 5-6 membered heterocyclic ring having a ring nitrogen and 0-1 additional ring heteroatoms selected from N, O or S.

For compounds of formula III the following are preferred:

$R^1$, $R^2$, and $R^3$ are each hydrogen;

$L_1$ is —$CH_2CH_2$— or —$CH_2CH_2CH_2$—;

$L_2$ is —$CH_2CH_2CH_2$—, —$CH_2CH_2CH_2CH_2$—, —$CH(CH_3)CH_2CH_2$—, or —$CH(CH_3)CH_2CH_2CH_2$—;

$L_3$ is a direct link, —$CH_2$—, or —$CH_2CH_2$—;

$R^7$ is absent;

$R^8$ is -halo, —CN, or a substituted or unsubstituted group selected from —$R^{12}$, —$OR^1$, —$SR^{12}$, —$N(R^{10})_2$, —$NR^{10}C(O)R^1$, —$NR^{10}CO_2R^{12}$, —$CO_2R^1$, —$C(O)R^1$, —$C(O)N(R^{10})_2$, —$OC(O)N(R^{10})_2$, —$S(O)_2R^{12}$, —$SO_2N(R^{10})_2$, —$S(O)R^{12}$, —$NR^{10}SO_2N(R^{10})_2$, or —$NR^{10}SO_2R^{12}$, or two adjacent $R^8$ taken together with their intervening atoms form a 5-6 membered unsaturated or partially unsaturated ring having 0-2 heteroatoms selected from nitrogen, oxygen or sulfur;

$R^4$ and $R^5$ are each independently selected from $C_{1-3}$ alkyl or $R^4$ and $R^5$ taken together with their intervening nitrogen form a 5-6 membered ring;

$R^{14}$ is a 5-6 membered heterocyclic ring having a ring nitrogen and 0-1 additional ring heteroatoms selected from N, O or S;

each $R^{13}$ is hydrogen;

each $R^{10}$ is hydrogen;

each $R^{11}$ is independently selected from hydrogen or an optionally substituted $C_{1-5}$ aliphatic group; and each $R^{12}$ is independently selected from a substituted or unsubstituted $C_{1-5}$ aliphatic group.

For compounds of formula III, more preferred are compounds wherein Ring B is a phenyl ring having two $R^8$ substituents that are para to one another or Ring B is an α-naphthyl ring; and each $R^8$ is independently selected from halo, $C_{1-4}$ alkyl, $C_{1-3}$ alkoxy, CO($C_{1-3}$ alkyl), CONH($C_{1-3}$ alkyl), $SO_2(C_{1-3}$ alkyl), or $SO_2NH(C_{1-3}$ alkyl).

Another embodiment of this invention relates to a compound wherein $R^7$ at a position ortho to Q and $R^9$ are taken together with their intervening atoms to form a 5-7 membered unsaturated or partially unsaturated ring having 0-2 ring heteroatoms selected from N, O, or S. Such compounds are represented by formula IV:

IV

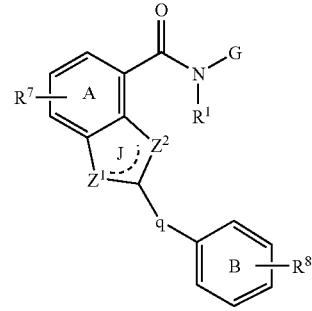

wherein q is a direct link, —$C(R^{11})_2$—, —$N(R^{10})$—, —N—, —O—, —$C(=O)$—, or —S—; $Z^1$ and $Z^2$ are each independently selected from —$[C(R^{11})_2]$—$_p$, —$C(R^{11})=C(R^{11})$—, —$N(R^{10})$—, —N—, —O—, —$C(=O)$—, and —S—, and $R^1$, G, $R^7$, $R^1$, $R^{10}$ and $R^{11}$ are as described above. The ring bearing $Z^1$ and $Z^2$ is designated Ring J. The selection of $Z^1$ and $Z^2$ will depend on the size of Ring J and whether Ring J is unsaturated or partially unsaturated. By reference to the specification, such selection will be within the knowledge of one skilled in the art. Representative examples of Ring J are shown in Table 2.

TABLE 2

Examples of Ring J Fused to Ring A

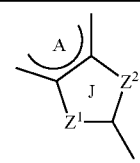

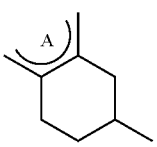

J-1

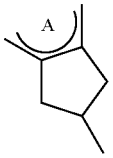

J-2

TABLE 2-continued

Examples of Ring J Fused to Ring A

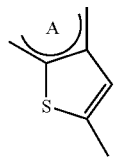
J-3

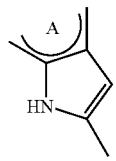
J-4

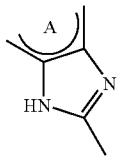
J-5

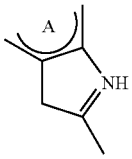
J-6

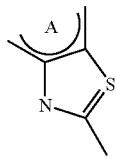
J-7

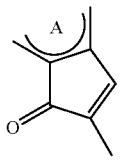
J-8

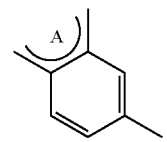
J-9

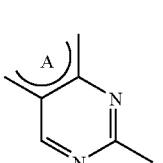
J-10

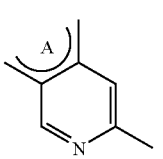
J-11

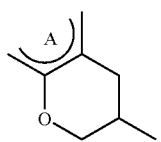
J-12

One embodiment of this invention relates to compounds wherein $R^1$ and $R^2$ are taken together with their intervening atoms to form a 5-7 membered ring (Ring D). Another embodiment of this invention relates to compounds wherein $R^2$ and $R^3$ are taken together with their intervening atoms to form a 5-7 membered ring (Ring E). These embodiments are represented below by formulae V and VI wherein $R^1$-$R^5$, $L_2$, X, Q, and Rings A and B are as described above.

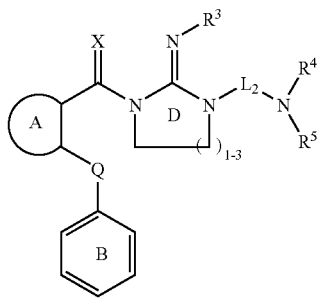

V

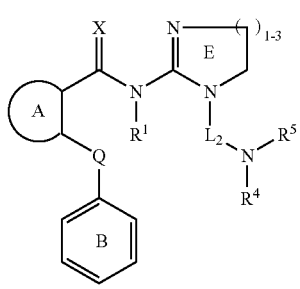

VI

Examples of specific compounds of this invention are shown in Table 3 below.

TABLE 3

Examples of Specific Compounds

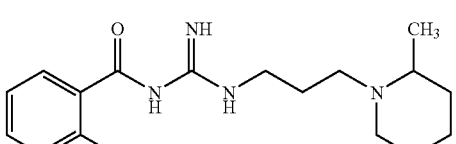
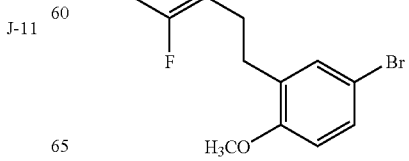

1

TABLE 3-continued

Examples of Specific Compounds

TABLE 3-continued
Examples of Specific Compounds
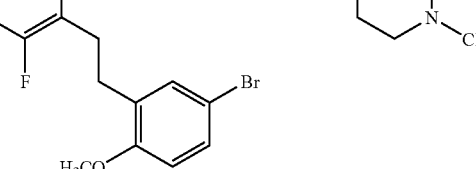 11
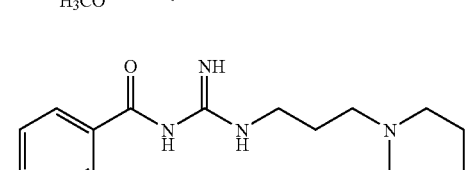 12
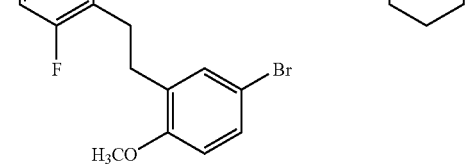 13
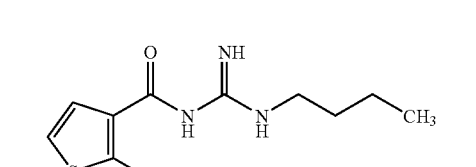 14
TABLE 3-continued
Examples of Specific Compounds
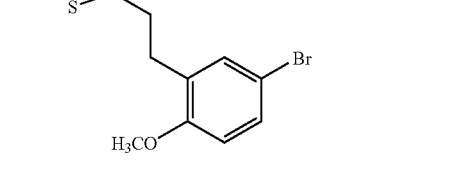 15
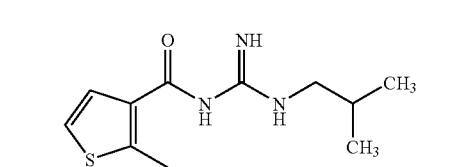 16
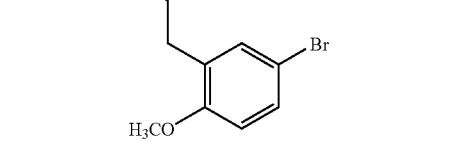 17
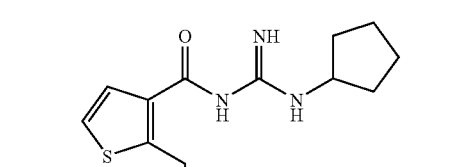 18
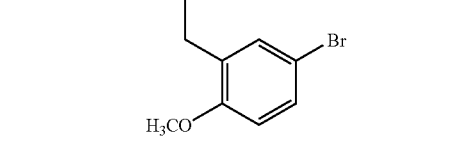 19

TABLE 3-continued
Examples of Specific Compounds
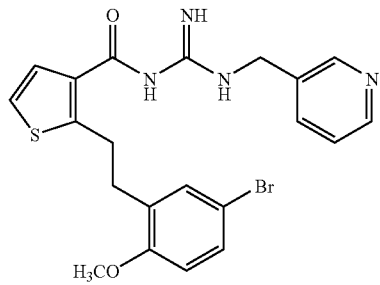
20
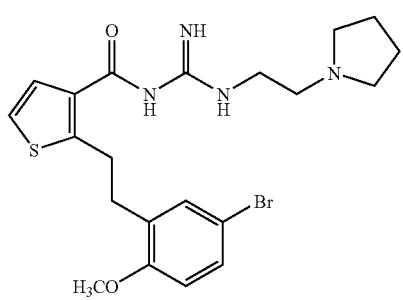
21
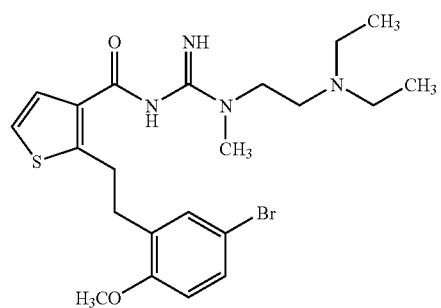
22
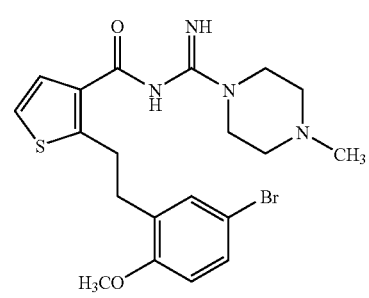
23
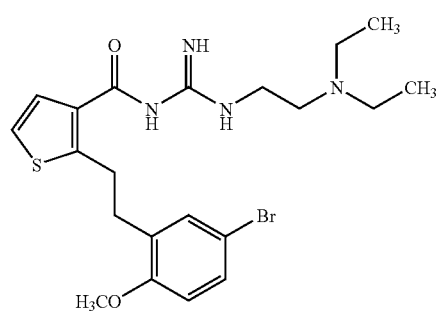
24
TABLE 3-continued
Examples of Specific Compounds
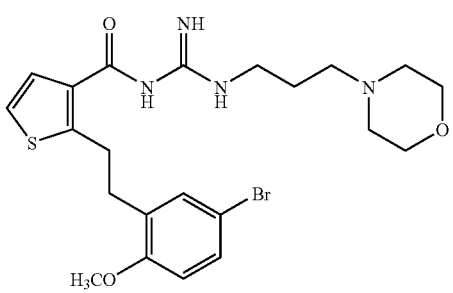
25
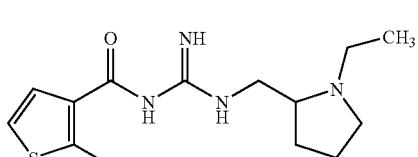
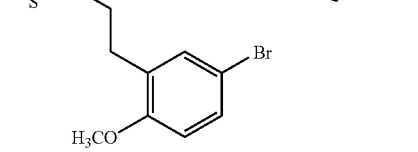
26
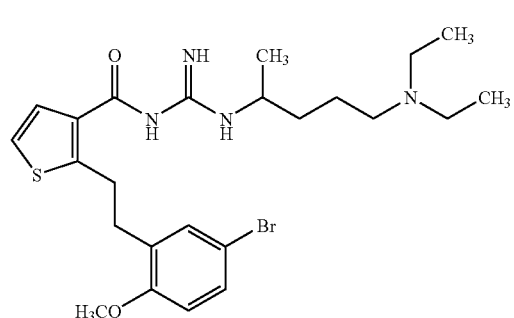
27
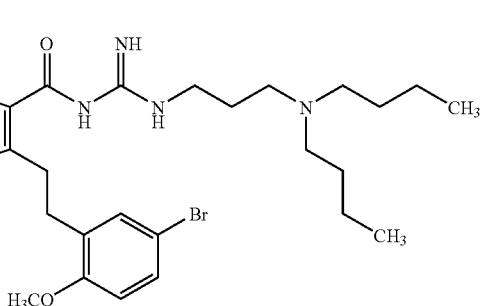
28
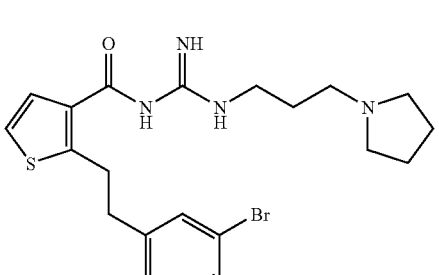
29

TABLE 3-continued
Examples of Specific Compounds
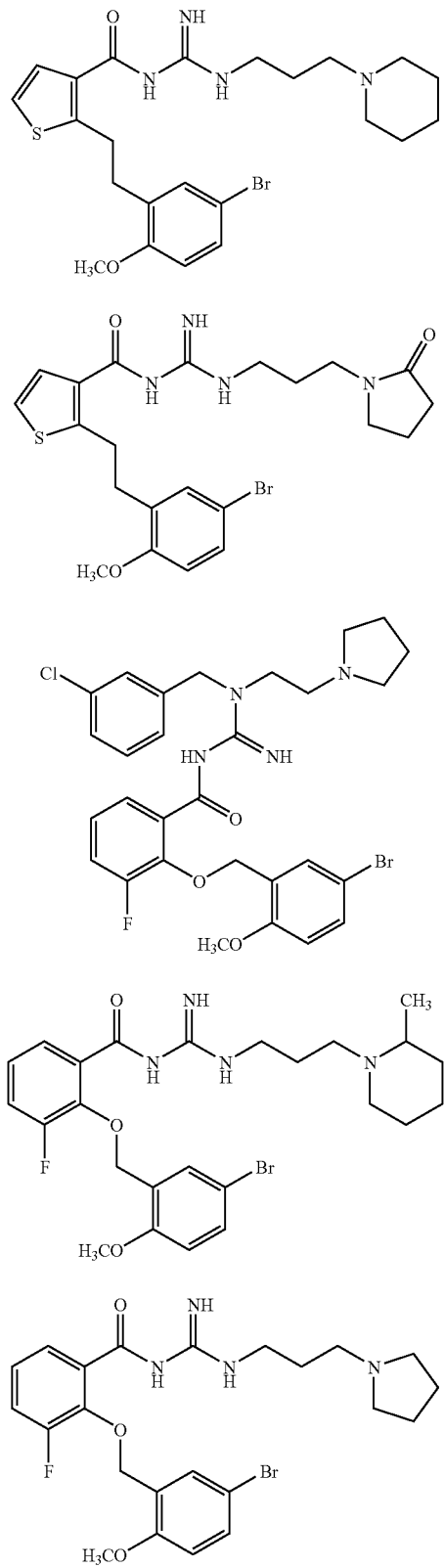
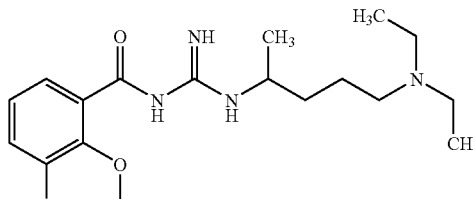

TABLE 3-continued
Examples of Specific Compounds
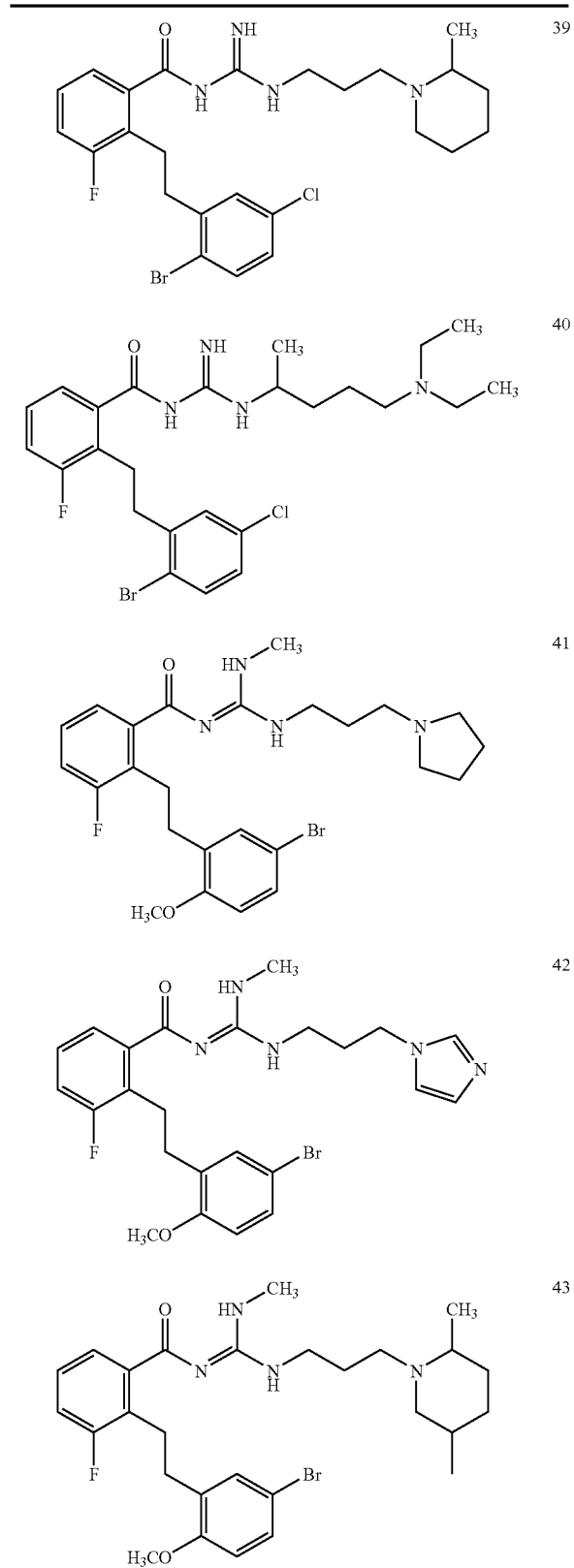
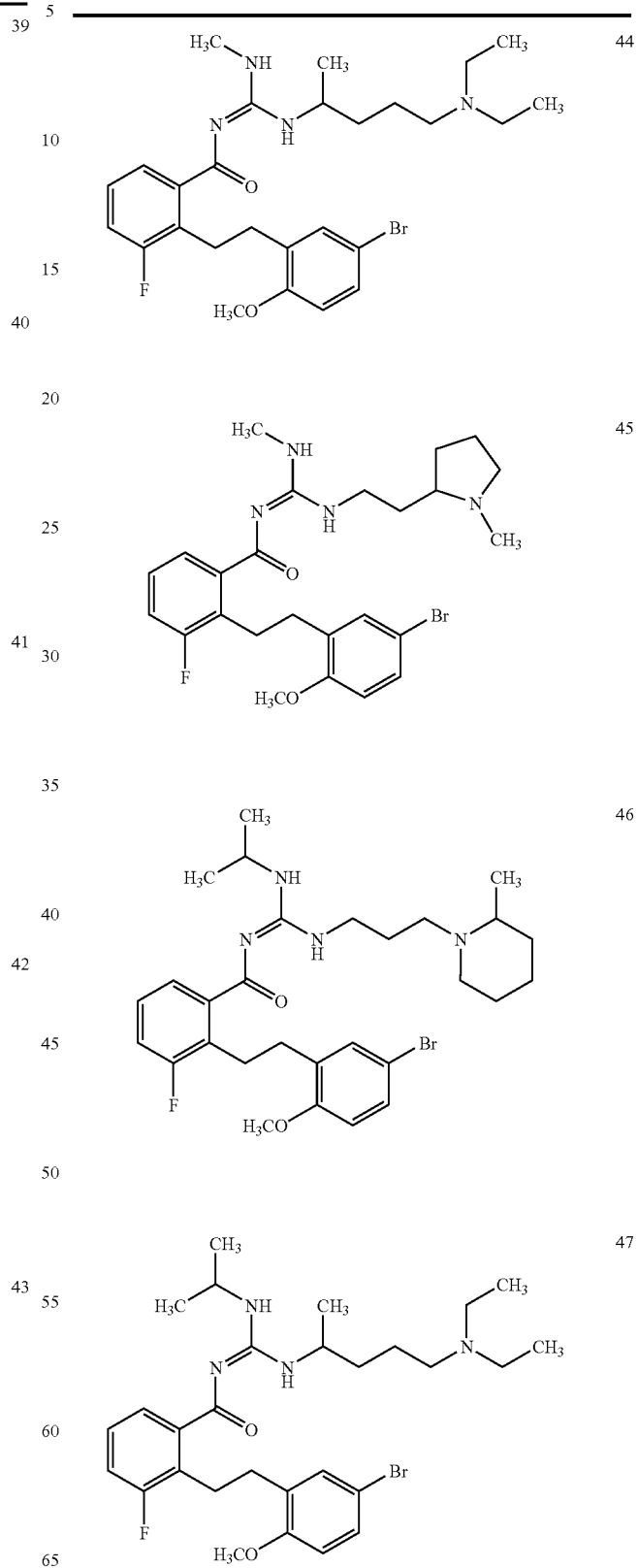

TABLE 3-continued
Examples of Specific Compounds
48
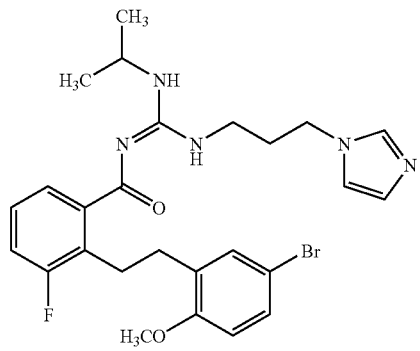
49
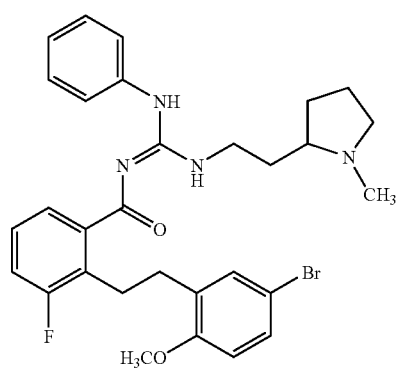
50
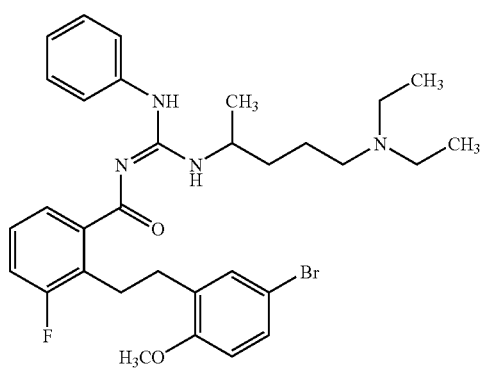
51
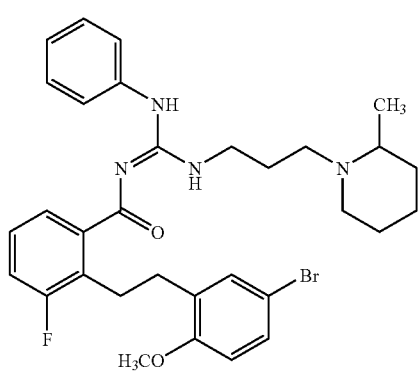
TABLE 3-continued
Examples of Specific Compounds
52
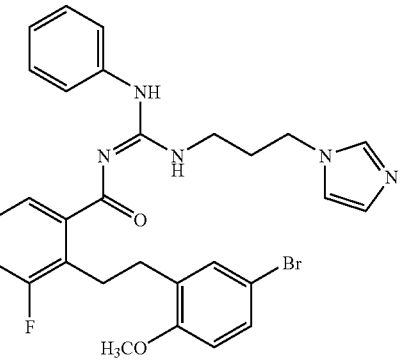
53
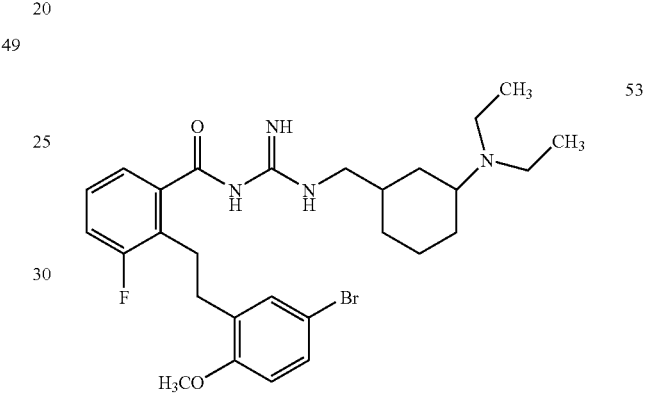
54
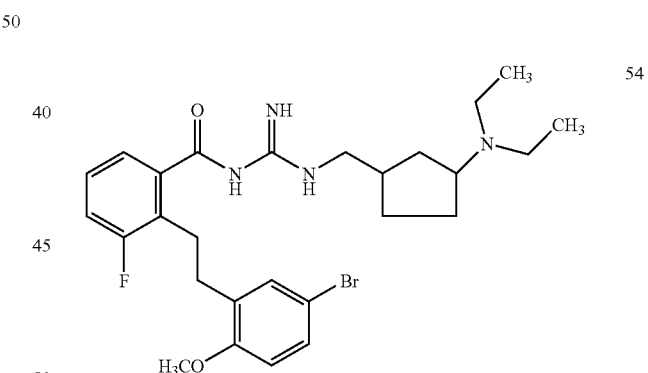
55
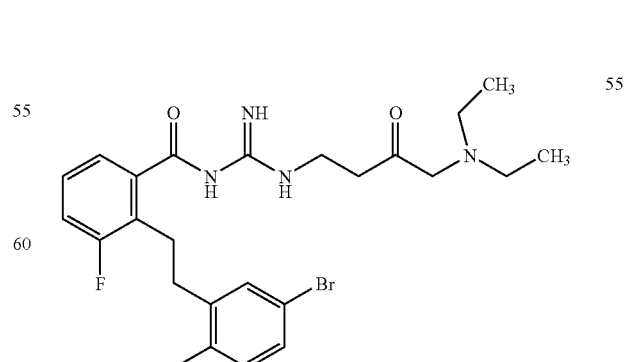

TABLE 3-continued
Examples of Specific Compounds
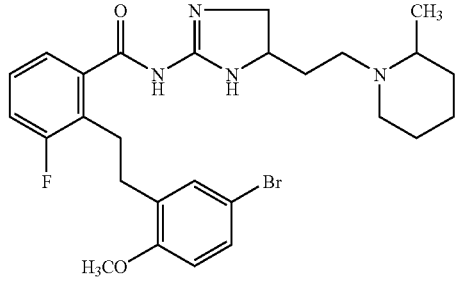

TABLE 3-continued
Examples of Specific Compounds
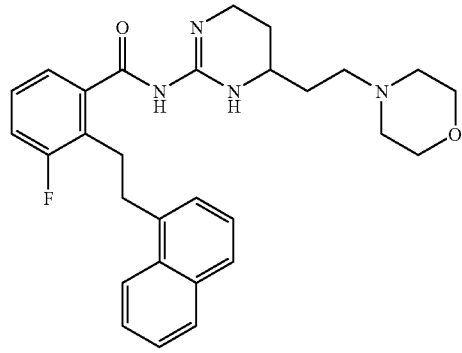
66
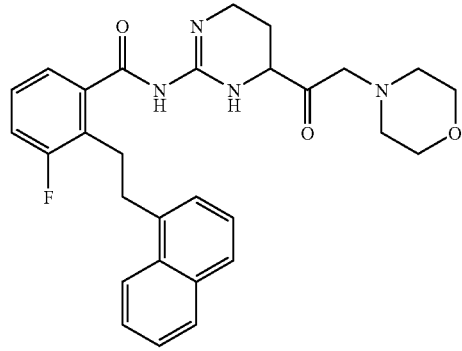
67
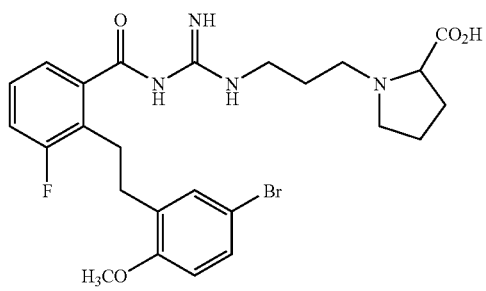
68
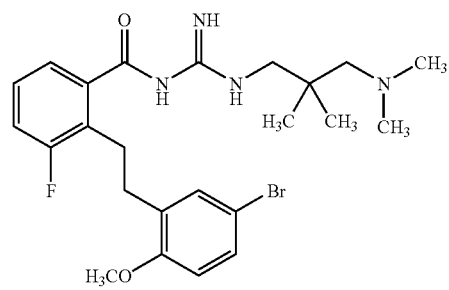
69
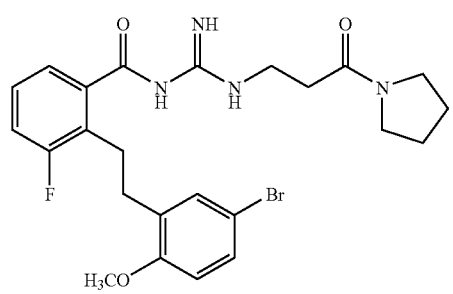
70
TABLE 3-continued
Examples of Specific Compounds
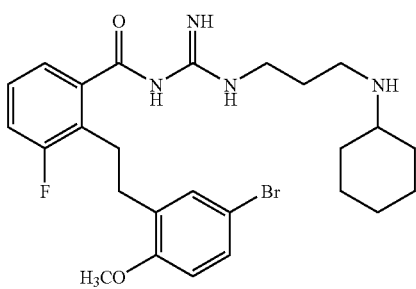
71
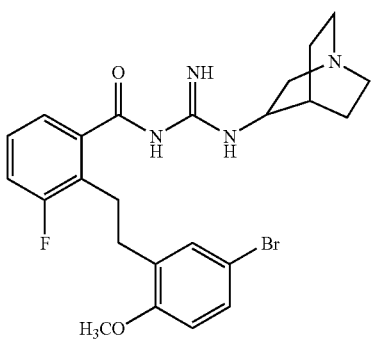
72
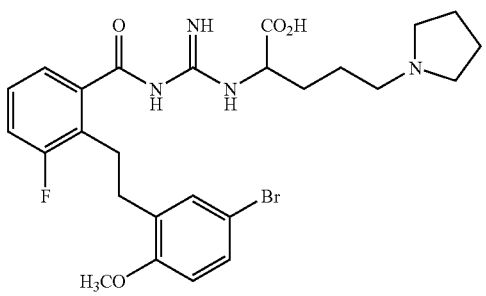
73
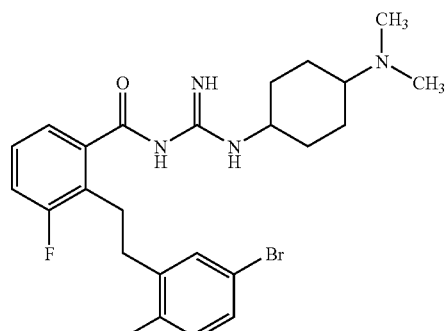
74

TABLE 3-continued

Examples of Specific Compounds

| 75 | 79 |
| 76 | 80 |
| 77 | 81 |
| 78 | 82 |
|    | 83 |

TABLE 3-continued
Examples of Specific Compounds
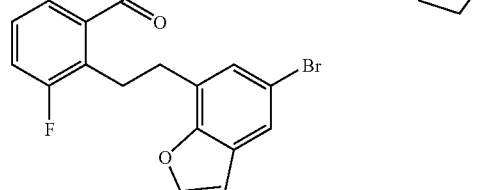
84
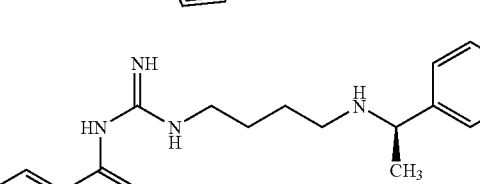
85
86
87
88
TABLE 3-continued
Examples of Specific Compounds
89
90
91
92
93

TABLE 3-continued
Examples of Specific Compounds
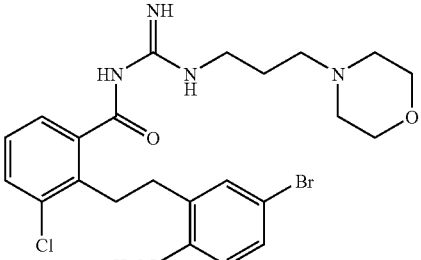 94
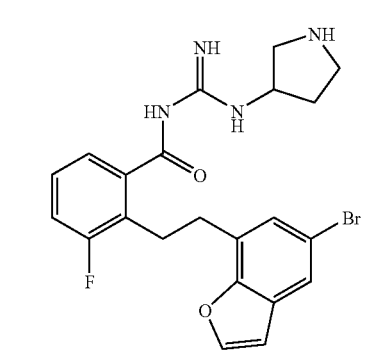 95
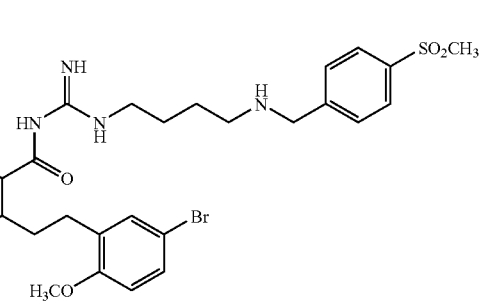 96
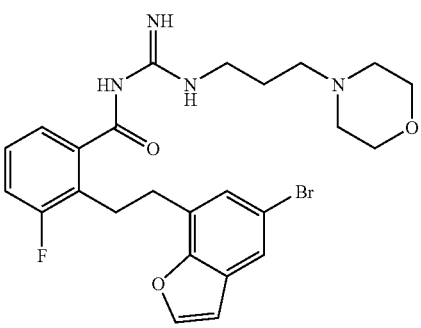 97
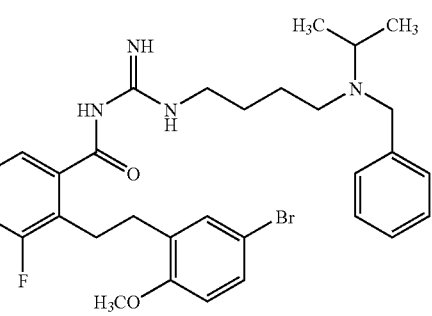 98
TABLE 3-continued
Examples of Specific Compounds
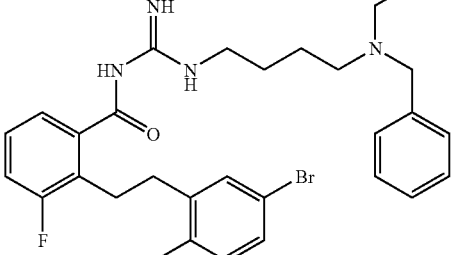 99
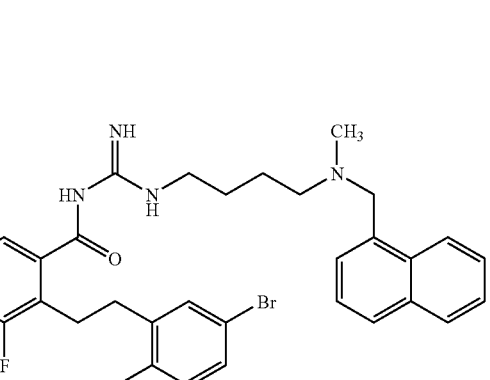 100
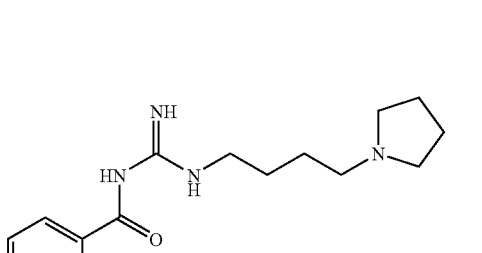 101
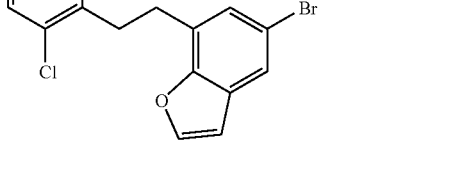 102

TABLE 3-continued
Examples of Specific Compounds
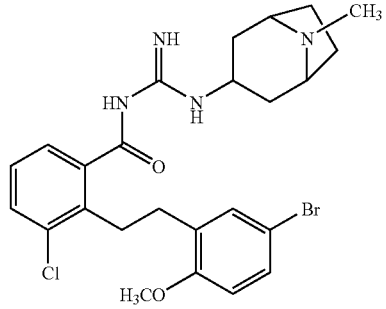
103
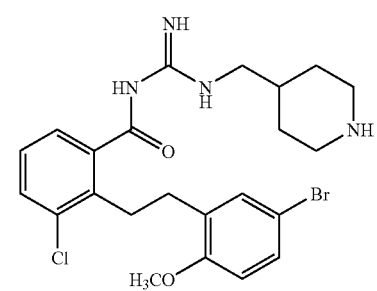
104
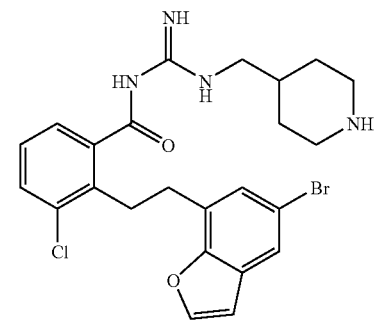
105
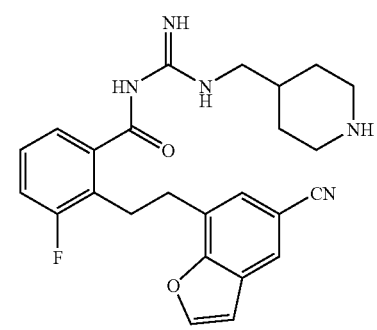
106
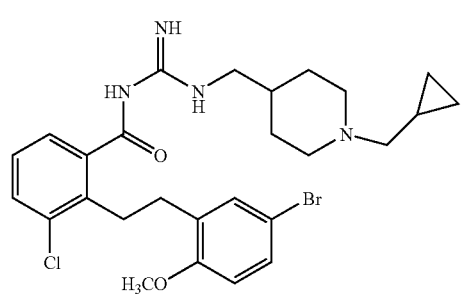
107
TABLE 3-continued
Examples of Specific Compounds
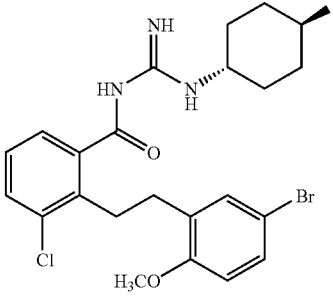
108
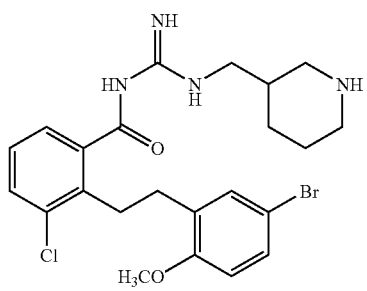
109
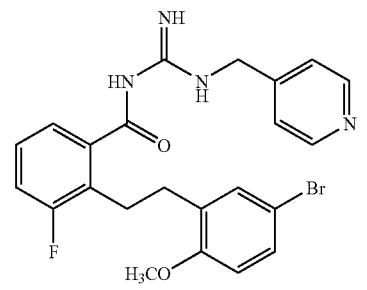
110
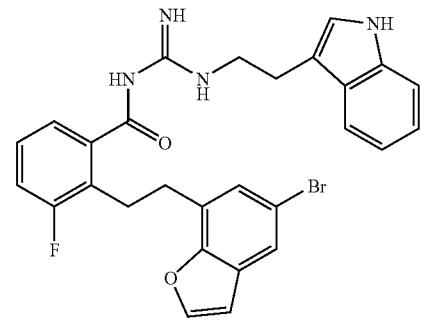
111
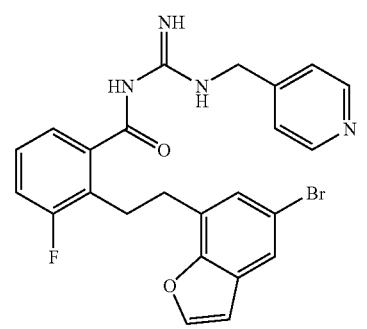
112

TABLE 3-continued
Examples of Specific Compounds
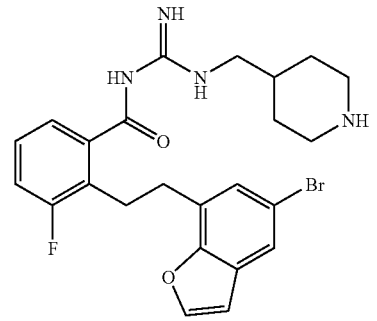
113
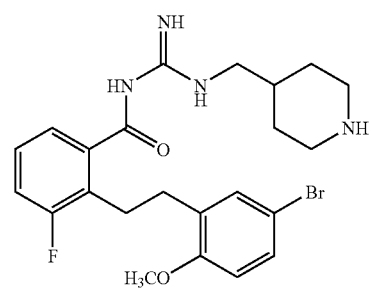
114
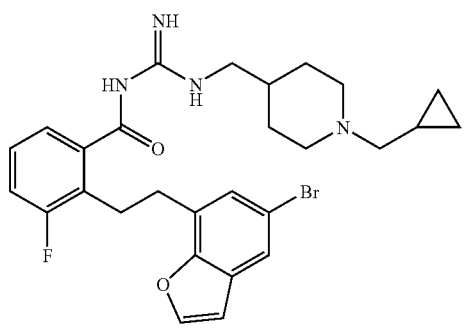
115
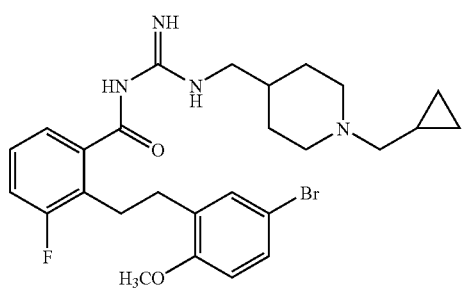
116
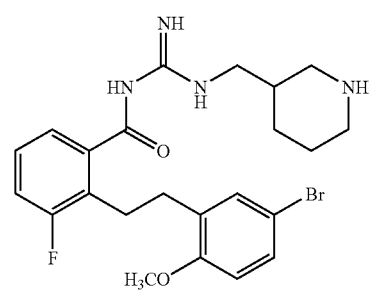
117
TABLE 3-continued
Examples of Specific Compounds
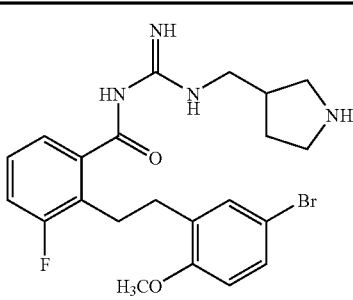
118
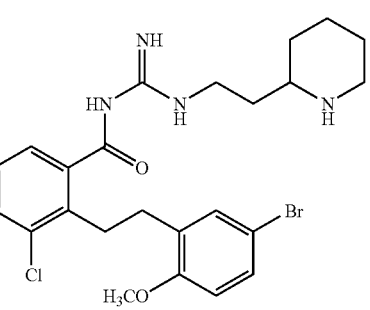
119
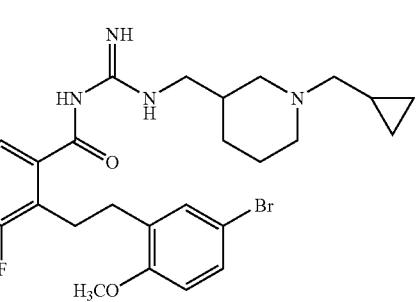
120
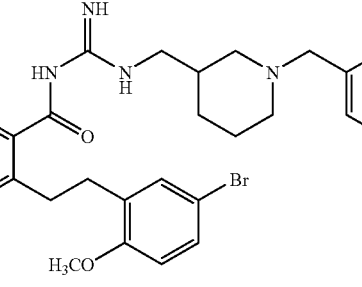
121
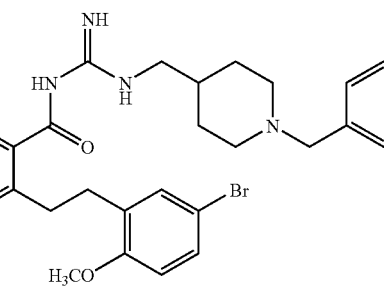
122

TABLE 3-continued
Examples of Specific Compounds
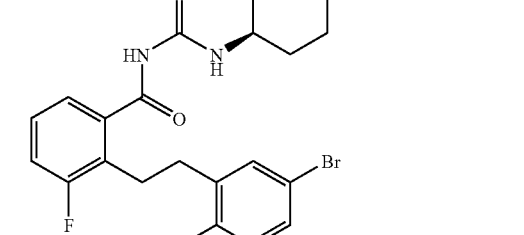 123
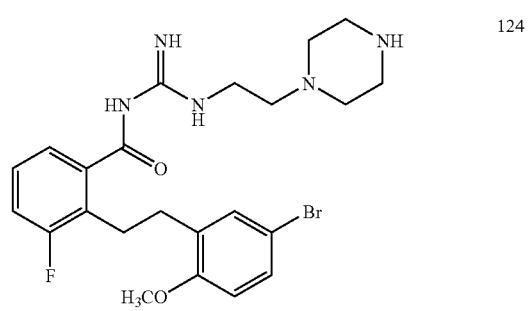 124
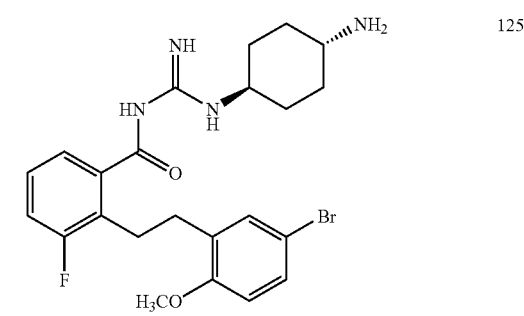 125
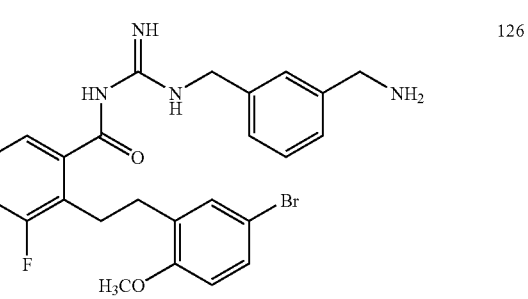 126
TABLE 3-continued
Examples of Specific Compounds
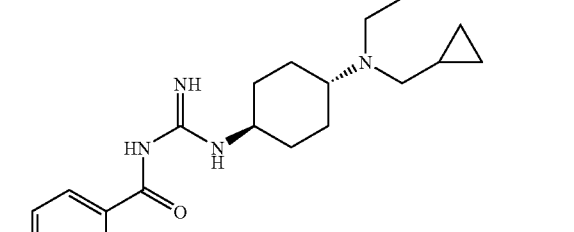 127
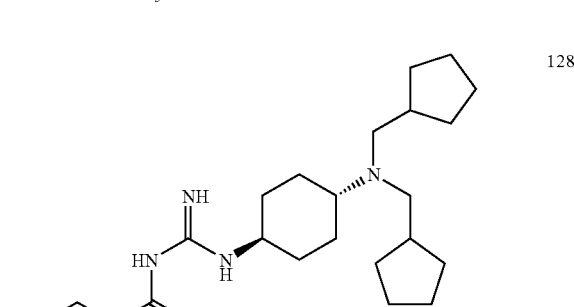 128
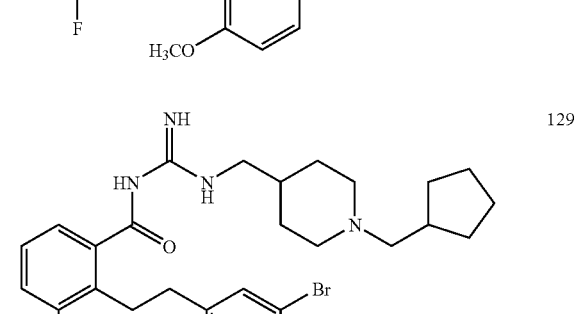 129
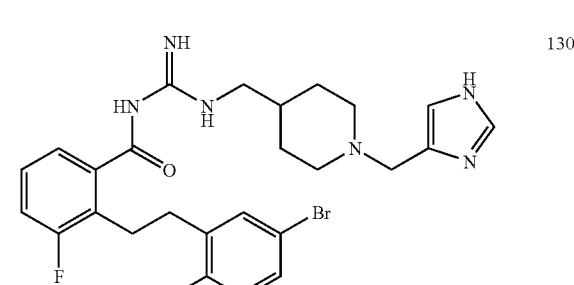 130

TABLE 3-continued

Examples of Specific Compounds

TABLE 3-continued
Examples of Specific Compounds
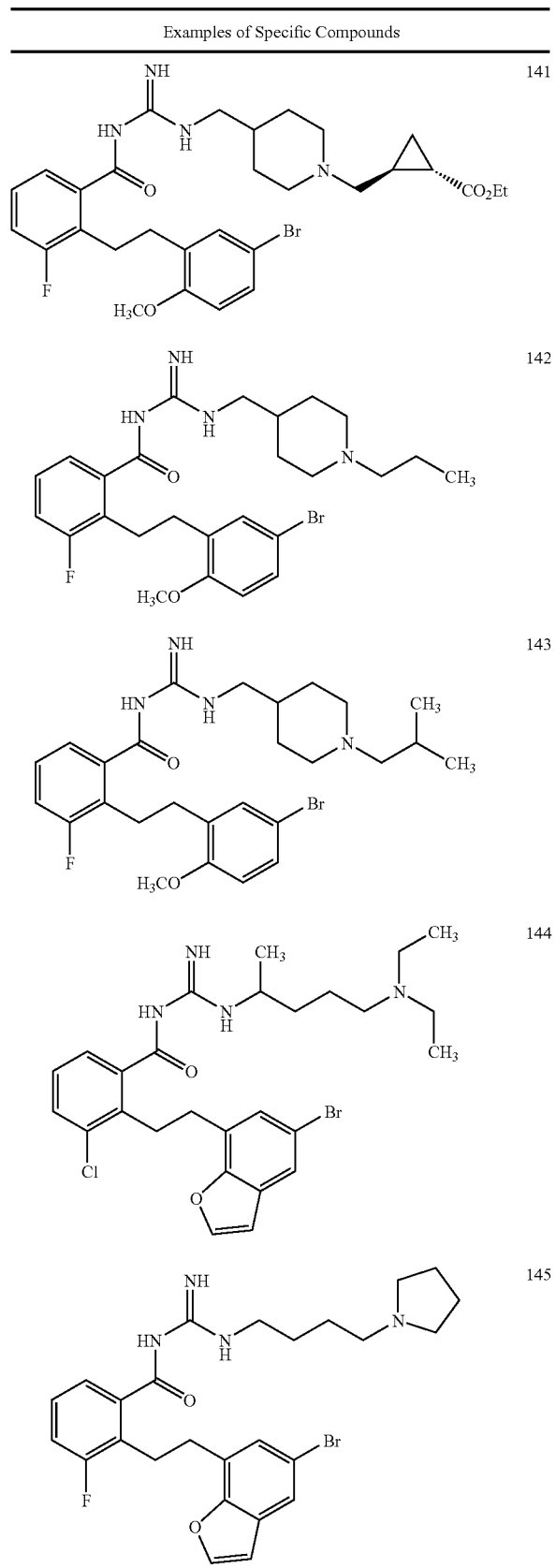
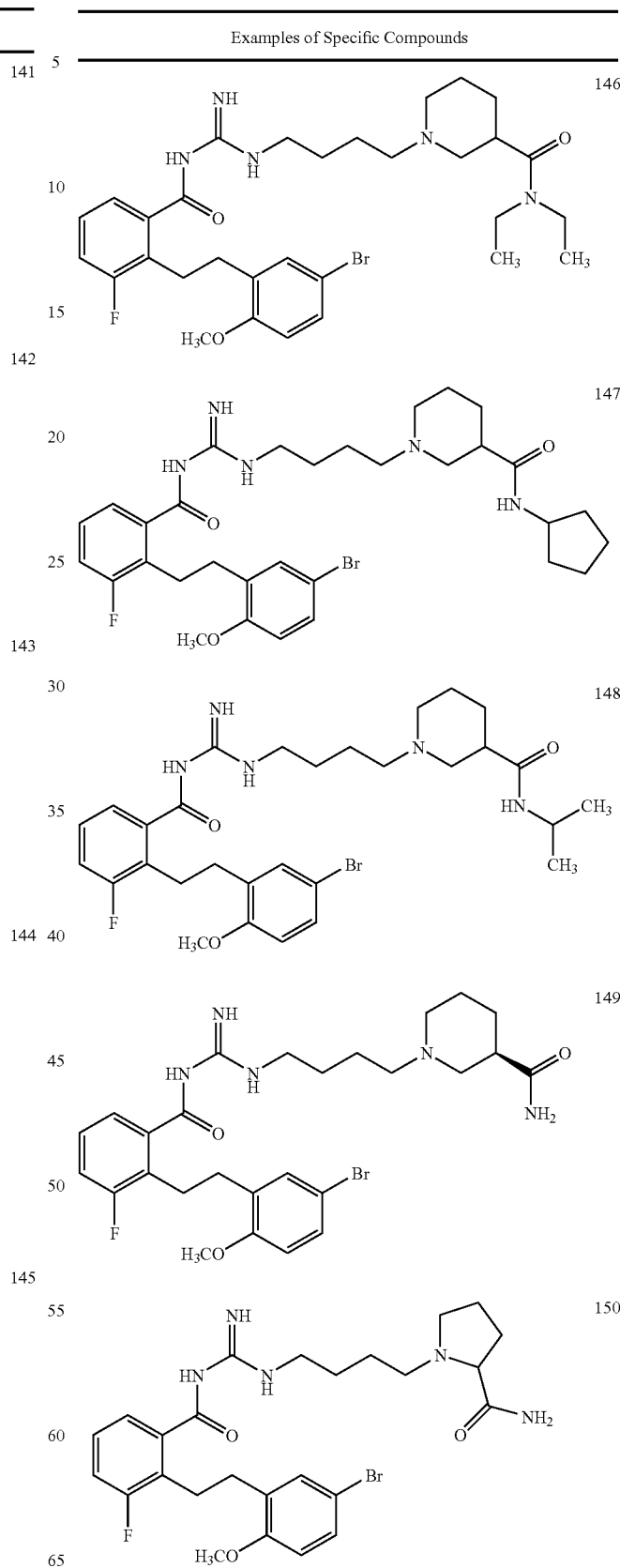

TABLE 3-continued
Examples of Specific Compounds
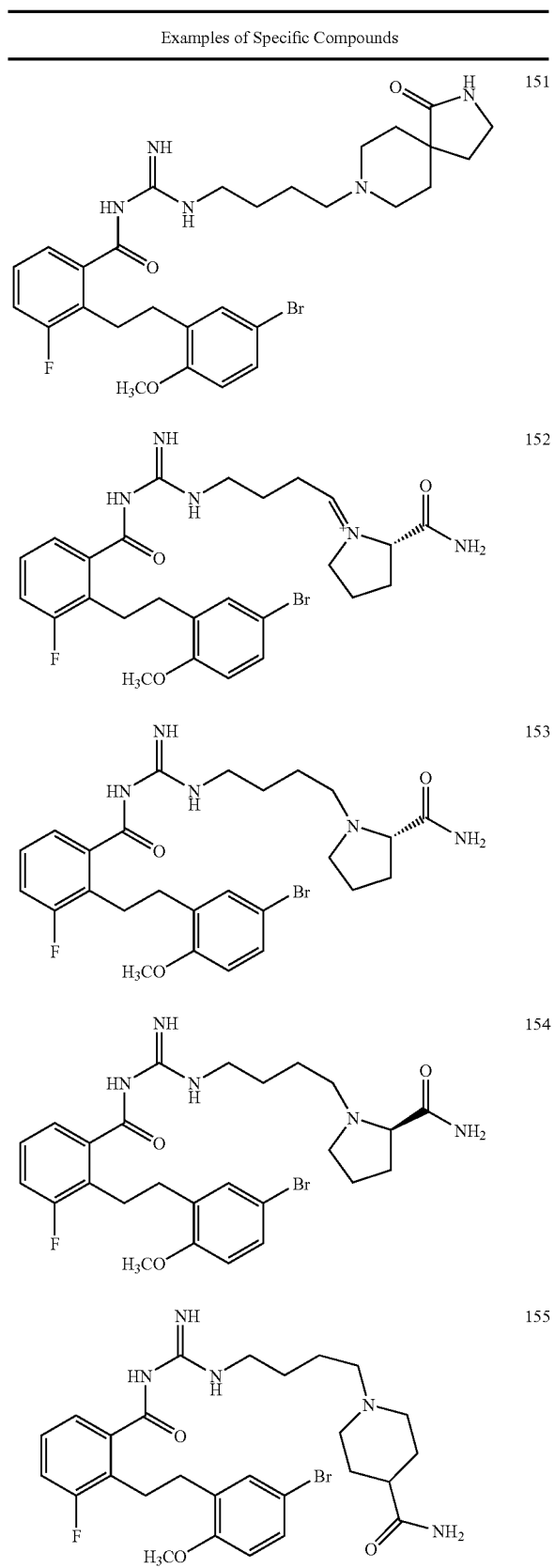
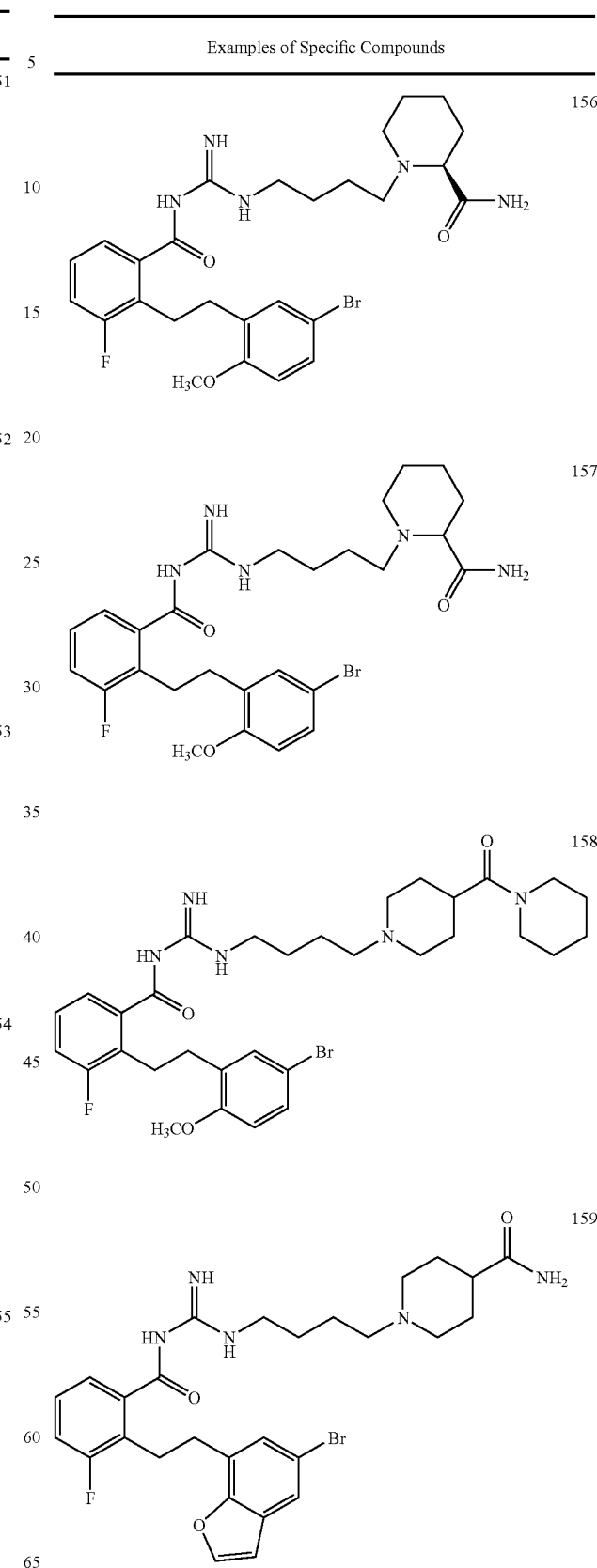

TABLE 3-continued
Examples of Specific Compounds
 160
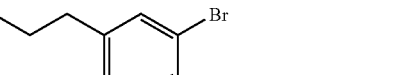 161
 162
 163
 164
TABLE 3-continued
Examples of Specific Compounds
 165
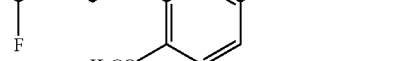 166
 167
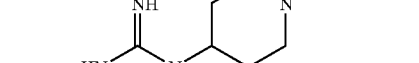 168
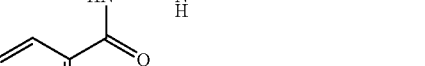 169

TABLE 3-continued
Examples of Specific Compounds
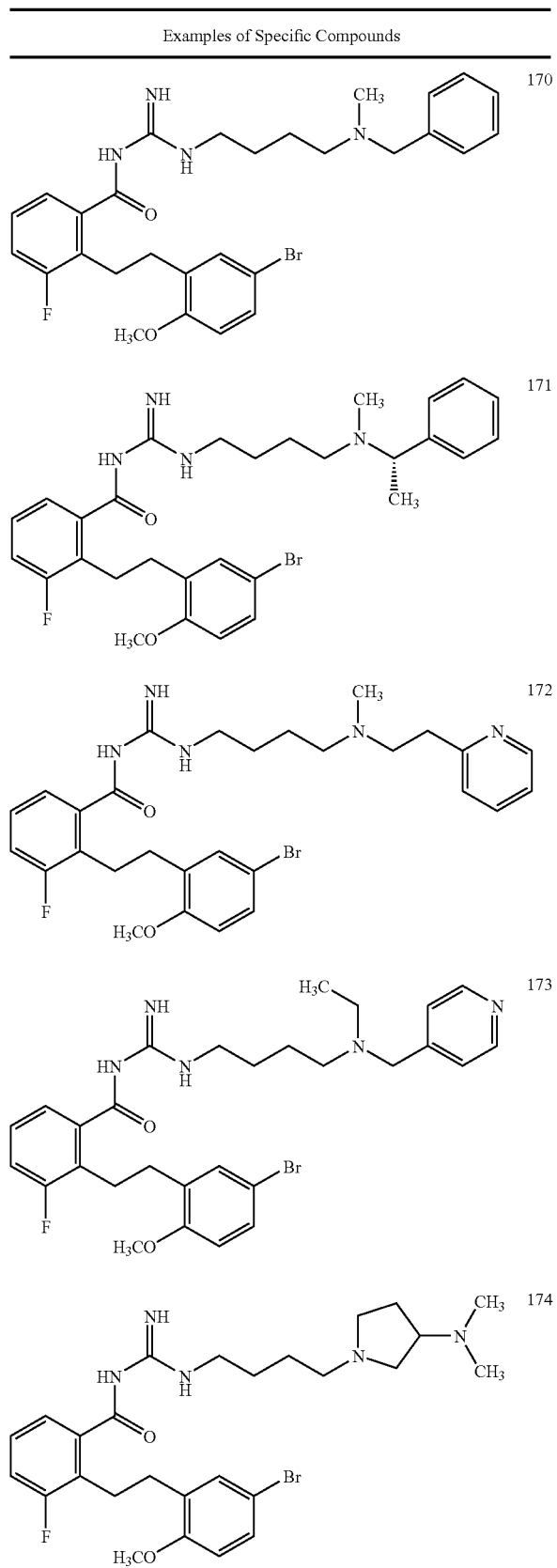
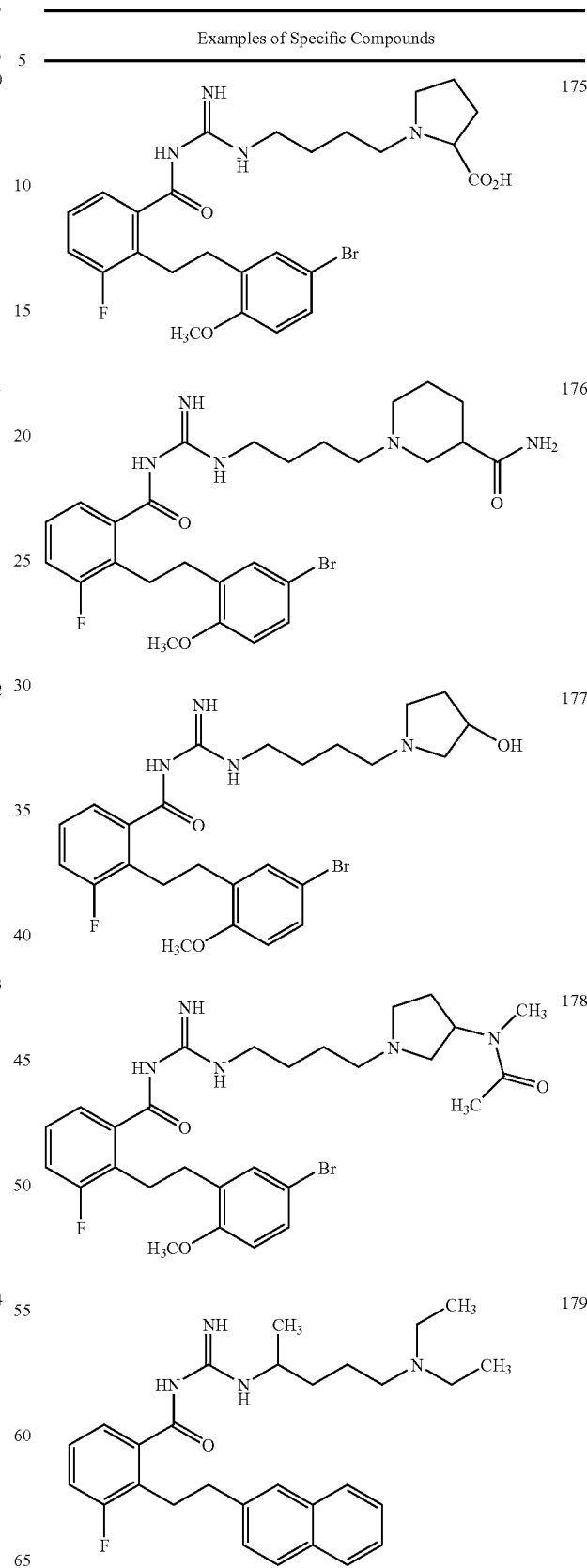

TABLE 3-continued
Examples of Specific Compounds
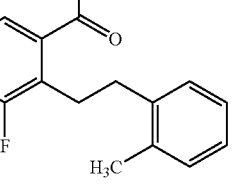 180
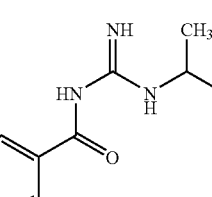 181
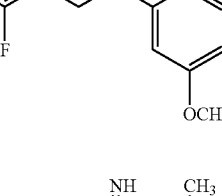 182
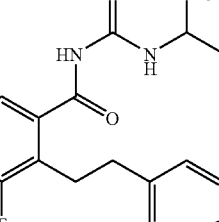 183
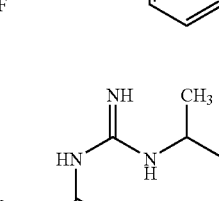 184
TABLE 3-continued
Examples of Specific Compounds
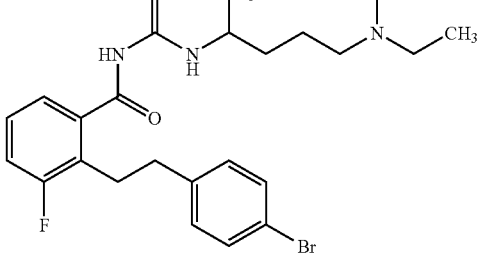 185
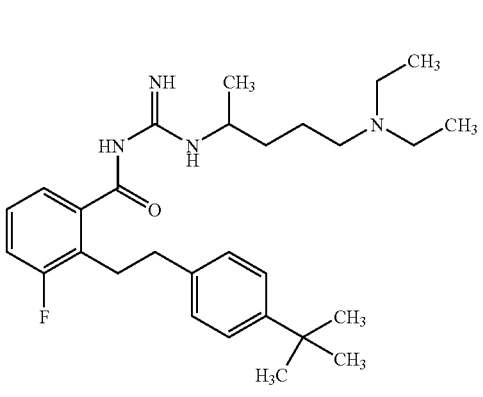 186
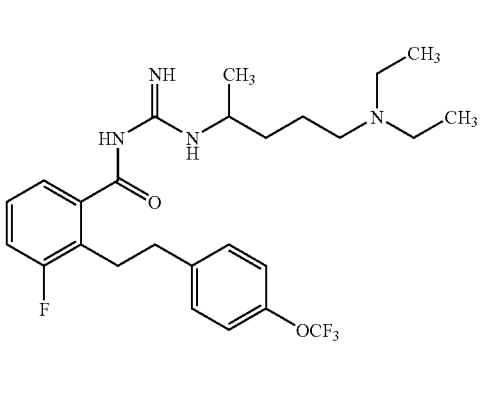 187
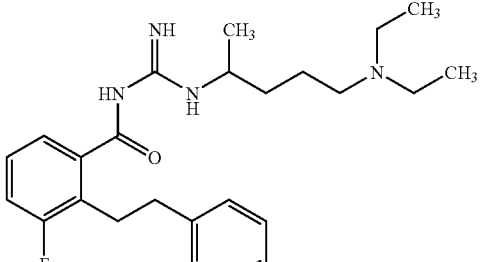 188
The compounds of this invention may be prepared by methods known to those skilled in the art for analogous compounds, as illustrated by the general schemes below, and by reference to the preparative examples shown below.

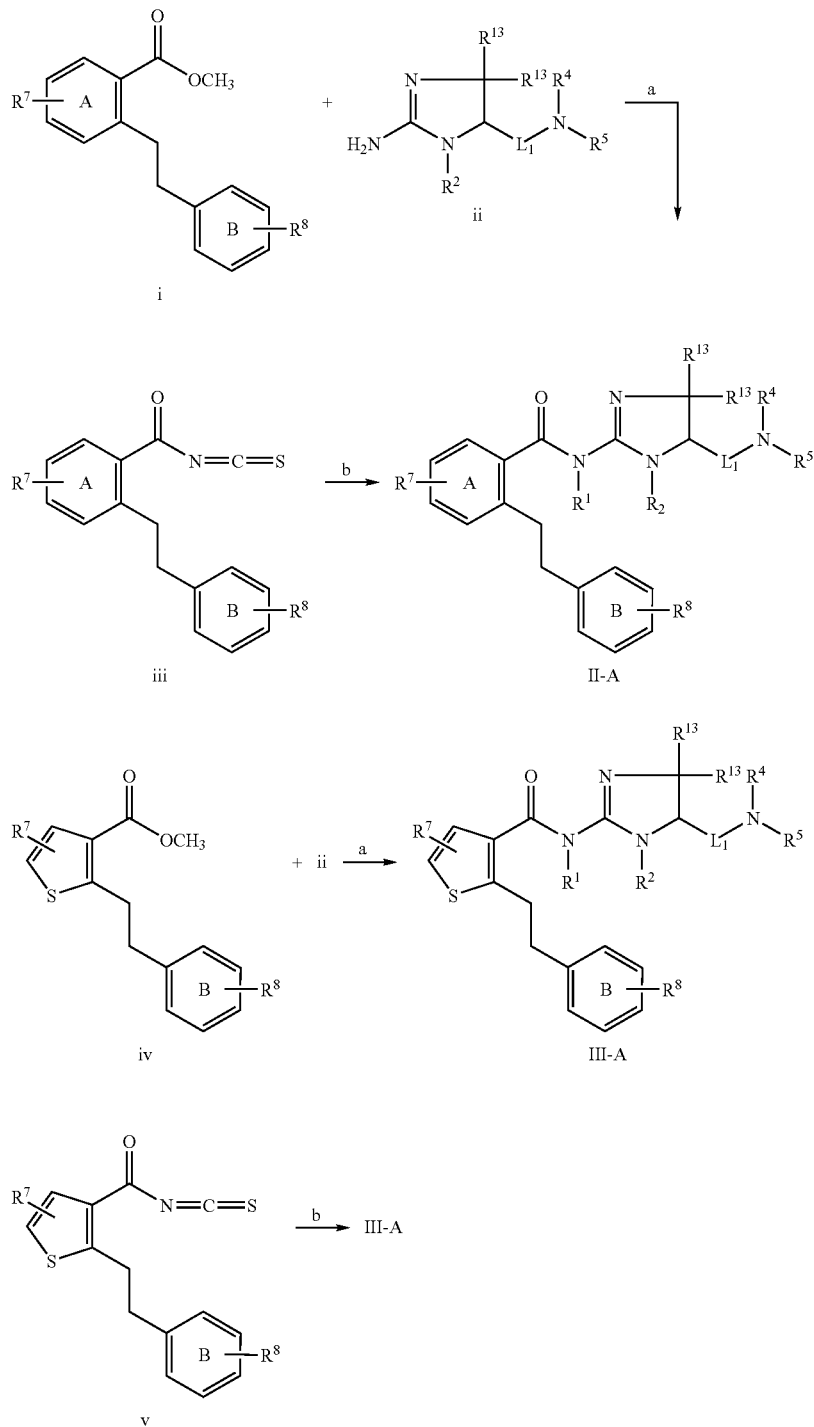
Scheme I above shows general routes for preparing compounds of formulae II-A and III-A. One may start with either an ester such as i or iv or an isothiocyanate such as iii or v. These routes are particularly useful when $R^1$ is hydrogen.

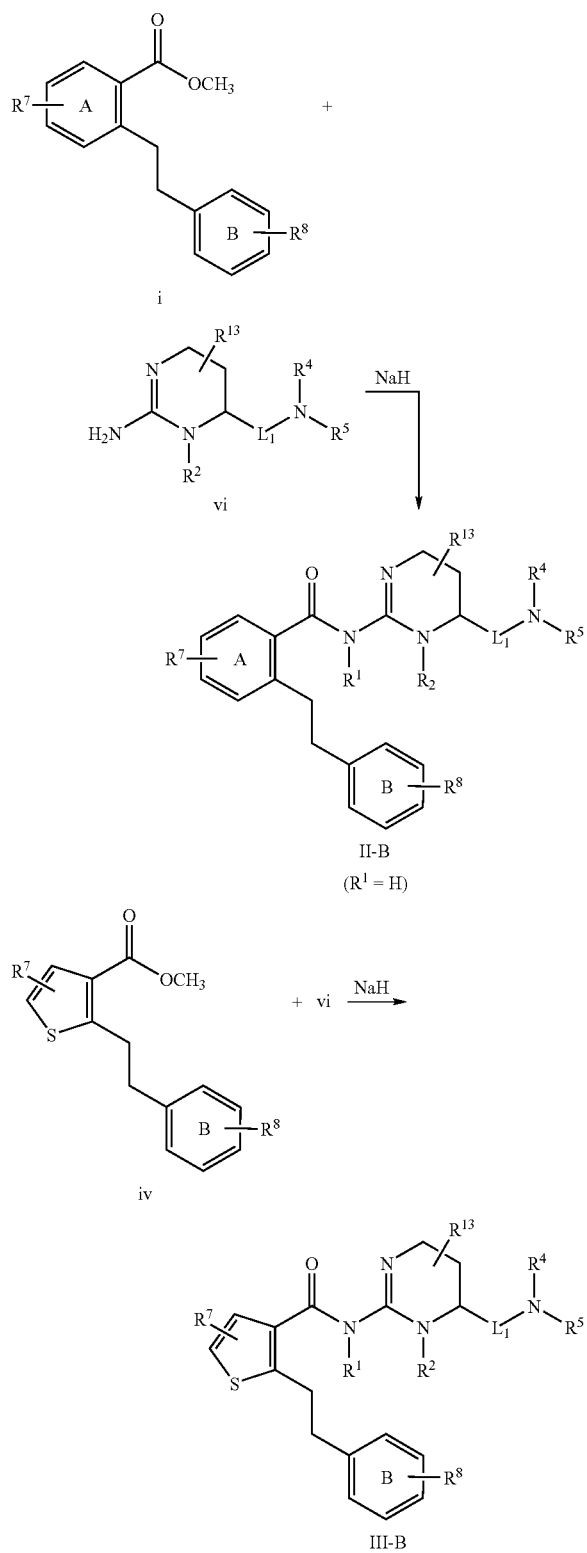
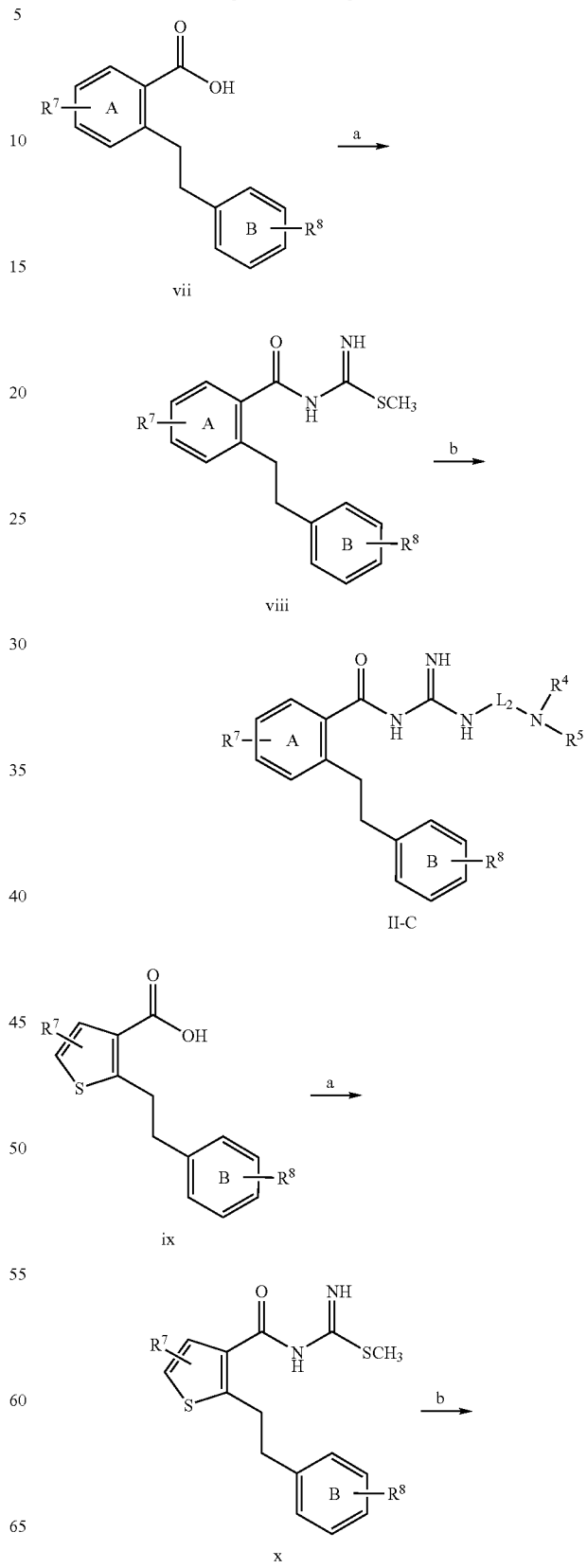
Scheme II above shows general routes for preparing compounds of formulae II-B and III-B. These routes are particularly useful when $R^1$ and $R^2$ are each hydrogen.

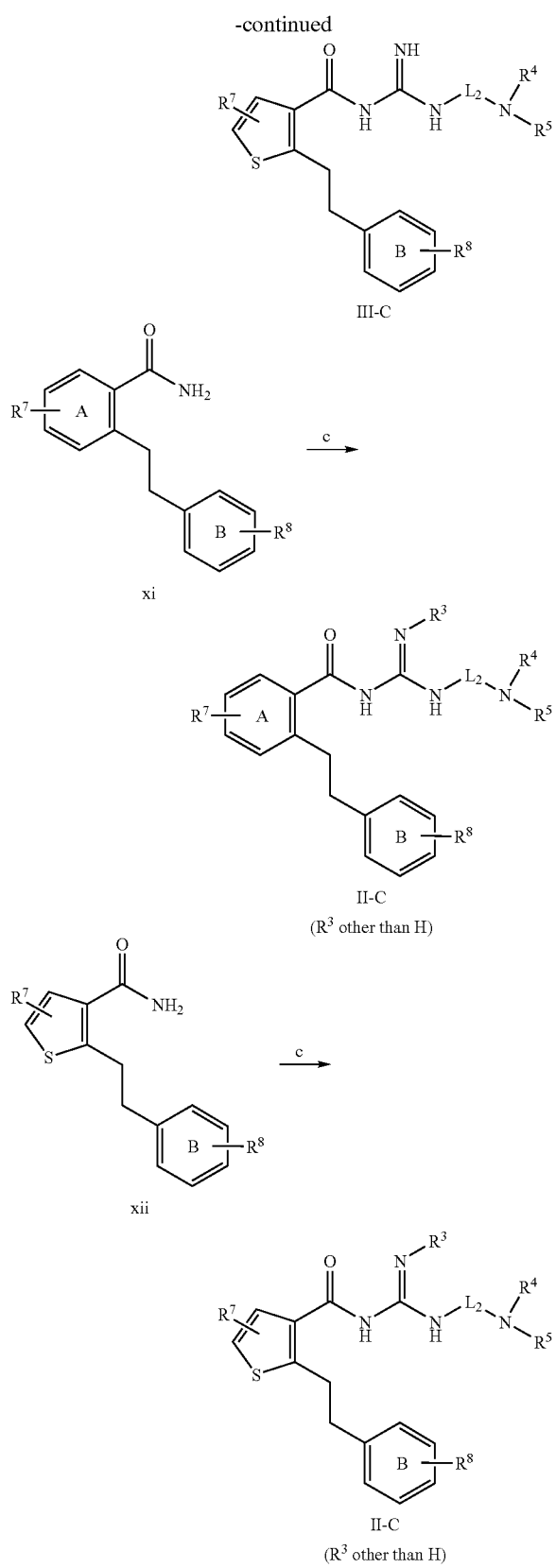

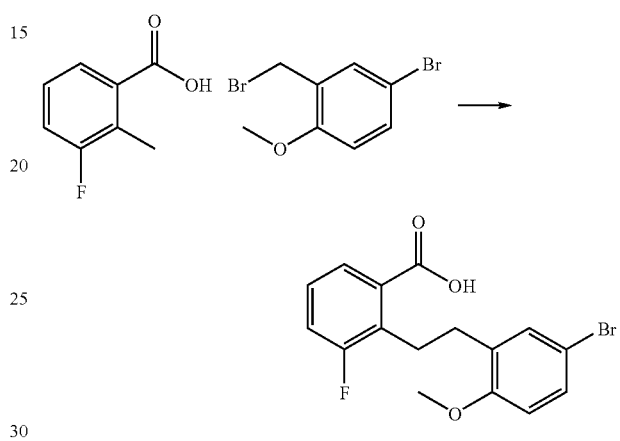

Scheme III above shows general routes for preparing compounds of formulae II-C and III-C. Starting with a carboxylic acid such as vii or ix, steps (a) and (b) may be used to prepare compounds where $R^3$ is hydrogen. Alternatively, an amide such as xi or xii may be treated as in step (c) to obtain compounds where $R^3$ is other than hydrogen.

SYNTHETIC EXAMPLES

Method of Toluic Acid Alkylation (General Method A)

A solution of 3-fluoro-2-methylbenzoic acid (5.00 g, 32 mmol, 1 equiv) and N,N,N',N'-tetramethylethylenediamine (TMEDA) (9.7 mL, 64 mmol, 2 equiv) in THF (100 mL) was cooled to −78° C. under an atmosphere of argon. s-BuLi (1.3 M in hexanes, 52 mL, 26 mmol, 2.1 equiv) was added dropwise and the solution was allowed to stir for 1 hr. A solution of 2-bromo-5-methoxybenzylbromide (22 g, 80 mmol, 2.5 equiv) in THF (10 mL) was added dropwise. The solution was allowed stir for 1 hr at −78° C. hr and then quenched by the addition of $H_2O$ and 1N HCl. The mixture was extracted with ethyl acetate. The combined organic phases were washed with brine, dried over $MgSO_4$, filtered, and concentrated. After column chromatography ($SiO_2$) followed by trituration from MeOH/DCM, 2-[2-(2-bromo-5-methoxy-phenyl)-ethyl]-3-fluoro-benzoic acid (3.3 g, 9.4 mmol, 80%) was obtained as a white powder. $^1$H NMR (300 MHz, $CDCl_3$) δ 7.66 (d, J=7.8 Hz, 1H), 7.12-7.33 (m, 4H), 6.78 (d, J=9.0 Hz, 1H), 3.76 (s, 3H), 3.24 (t, J=7.5 Hz, 2H), 2.83 (t, J=7.5 Hz, 2H). LCMS: ES⁻ 351 (M−1), 353 (M+1), 355 (M+3).

The following acids were also prepared by General Method A:

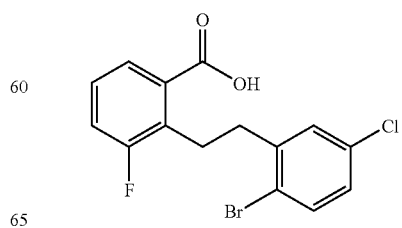

Reagents and conditions: (a) 1. $SOCl_2$, 2. 1N NaOH, $H_2NC(\!=\!\!=\!\!NH)SCH_3$; (b) $H_2N$-$L_2$-$N(R^4)(R^5)$, $Et_3N$, xylenes, heat; (c) 1. NaH, $R_3NCS$, 2. $H_2N$-$L_2$-$N(R^4)(R^5)$, $HgCl_2$ 2-[2-(5-Bromo-2-methoxy-phenyl)-ethyl]-3-fluoro-benzoic acid: LCMS ES⁻ 355 (M−1), 357 (M+1), 359 (M+3).

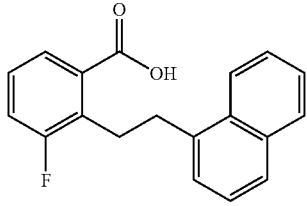

3-Fluoro-2-(2-naphthalen-1-yl-ethyl)-benzoic acid: LCMS ES⁻ 293 (M−1).

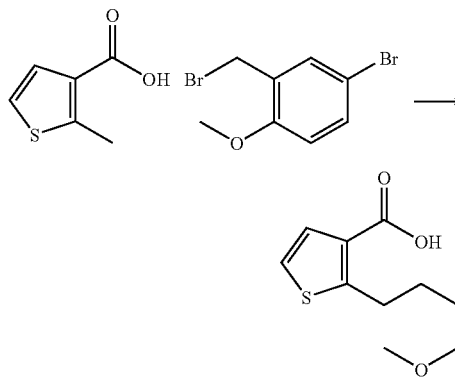

To a solution of 2-methyl-thiophene-3-carboxylic acid (8.01 g, 56.0 mmol, 1.0 equiv) in THF (56 mL) at −78° C. was added a solution of lithium diisopropylamide (LDA; 2M, 56 mL, 112.0 mmol, 2 equiv). The orange solution was allowed to stir for 1 hr and then a solution of 4-bromo-2-bromomethyl-1-methoxybenzene (17 g, 73 mmol, 1.3 equiv) in THF (50 mL) was added dropwise via cannula. The solution was allowed to stir at −78° C. for one hour and then warmed to room temperature. The reaction was quenched by the addition of water and ethyl acetate. The phases were separated and the organic phase was washed with brine, dried over Na₂SO₄, filtered, and concentrated to give a yellow oil. Addition of methanol caused precipitation of a white solid, which was filtered and dried to give 2-[2-(5-bromo-2-methoxy-phenyl)-ethyl]-thiophene-3-carboxylic acid (5.3 g, 15.5 mmol, 27%). ¹H NMR (300 MHz, d₆-DMSO) δ 12.59 (s, 1H), 7.31 (dd, J=8.7, 5.7 Hz, 1H), 7.26 (dd, J=6.6, 5.4 Hz, 2H), 7.21 (d, J=2.4 Hz, 1H), 6.88 (d, J=9.0 Hz, 1H), 3.71 (s, 3H), 3.27-3.35 (m, 2H), and 2.79-2.88 (m, 2H). LCMS ES⁻ 339 (M−1), 341 (M+1).

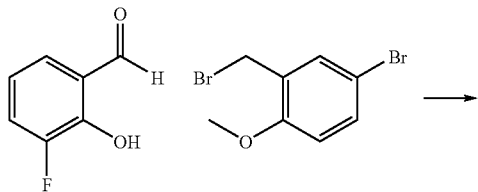

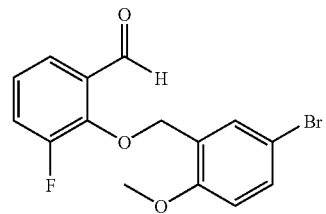

To a solution of 3-fluorosalicylaldehyde (2.0 g, 14.3 mmol, 1 equiv) in acetone (40 mL) were added potassium carbonate (6.0 g, 43.3 mmol, 3 equiv), and 2-bromo-5-methoxybenzyl-bromide (5.3 g, 19.0 mmol, 1.3 equiv). The solution was heated to 65° C. for 6 hours and then allowed to cool to room temperature and stir over night. The reaction was quenched by the addition of H₂O and 1N NaOH and extracted with CH₂Cl₂. The combined organic phases were washed with brine, dried over MgSO₄, filtered and concentrated. The crude product was purified by column chromatography (SiO₂, 4:1 hexanes:ethyl acetate) to give 2-(5-bromo-2-methoxybenzyloxy-3-fluorobenzaldehyde (0.47 g, 10%) as a white solid. ¹H NMR (300 MHz, CDCl₃) δ 10.28 (s, 1H), 7.60 (d, J=7.6 Hz, 1H), 7.52 (d, J=2.5 Hz, 1H), 7.31-7.49 (m, 2H), 7.06-7.19 (m, 1H), 6.78 (d, J=8.7 Hz, 1H), 5.25 (s, 2H), and 3.77 (s, 3H).

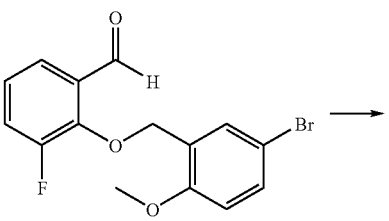

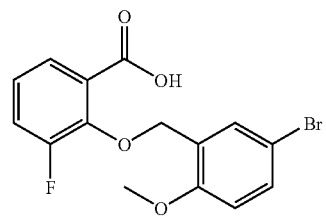

A solution of 2-(5-bromo-2-methoxybenzyloxy-3-fluorobenzaldehyde (0.86 g, 2.5 mmol, 1 equiv) in 1:2H₂O:dioxane (75 mL) was stirred at room temperature. To this solution was added concentrated sulfuric acid (1.29 g, 13.2 mmol, 5 equiv), and then a solution of sodium chlorite (0.28 g, 3.1 mmol, 1.3 equiv) in H₂O (25 mL). The solution was allowed to stir at room temperature for one hour and then quenched by pouring into H₂O. The mixture was extracted with ethyl acetate and the combined organic phases were washed with brine, dried over MgSO₄, and concentrated to give 2-(5-bromo-2-methoxy-benzyloxy)-3-fluoro-benzoic acid as a white solid in quantitative yield. ¹H NMR (300 MHz, CDCl₃) δ 7.92 (dt, J=7.9, 1.8 Hz, 1H), 7.49 (d, J=2.6 Hz, 1H), 7.42-7.47 (m, 1H), 7.30-7.40 (m, 1H), 7.11-7.20 (m, 1H), 6.80 (d, J=8.7 Hz, 1H), 5.35 (s, 2H), and 3.84 (s, 3H). LCMS: ES⁻ 353 (M−1), 355 (M+1).

Method for Isothiourea Formation (General Method B)

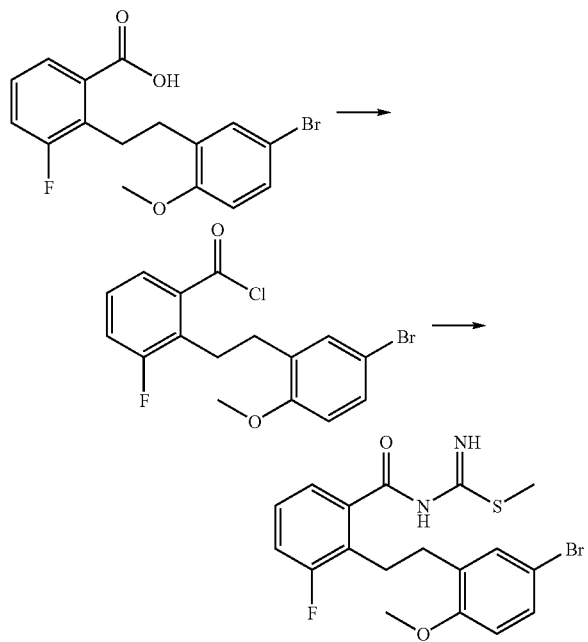

To a solution of 2-[2-(5-bromo-2-methoxyphenyl)-ethyl]-3-fluorobenzoic acid (0.81 g, 2.3 mol, 1 equiv) in THF (13 mL) was added thionyl chloride (0.84 mL, 11.5 mmol, 5 equiv). The solution was heated to reflux. After one hour, the solution was cooled to room temperature and concentrated to give 2-[2-(5-bromo-2-methoxy-phenyl)-ethyl]-3-fluorobenzoyl chloride as an oil, which was used without further purification.

A solution of 2-methyl-2-thiopseudourea sulfate (1.6 g, 5.75 mmol, 2.5 equiv) in 1N NaOH (10 mL) was cooled to 0° C. To this solution was added dropwise a solution of 2-[2-(5-bromo-2-methoxyphenyl)-ethyl]-3-fluoro-benzoyl chloride (2.3 mmol, 1 equiv) in diethyl ether (4 mL). The solution-was allowed to stir for 3.5 hr and then diluted with $H_2O$. The aqueous solution was extracted with dichloromethane and the combined organic phases were dried over $Na_2SO_4$, filtered, and concentrated to give 1-{2-[2-(5-bromo-2-methoxyphenyl)-ethyl]-3-fluorobenzoyl}-2-methylisothiourea in quantitative yield. The crude product was used without further purification. $^1$H NMR (300 MHz, CDCl$_3$) δ 7.72 (d, J=7.2 Hz, 1H), 7.07-7.30 (m, 4H), 6.68 (d, J=8.1 Hz, 1H), 3.73 (s, 3H), 3.27-3.33 (m, 2H), 2.84-2.90 (m, 2H), and 2.52 (s, 3H).

The following isothioureas were also prepared by General Method B:

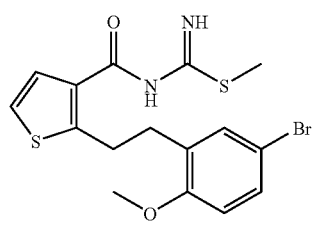

1-{2-[2-(5-Bromo-2-methoxy-phenyl)-ethyl]-thiophene-3-carbonyl}-2-methyl-isothiourea: $^1$H NMR (300 MHz, CDCl$_3$) δ 7.61 (d, J=5.1 Hz, 1H), 7.23-7.32 (m, 2H), 6.96 (d, J=5.4 Hz, 1H), 6.69 (d, J=9.0 Hz, 1H), 3.783 (s, 3H), 3.50-3.57 (m, 2H), 2.92-3.00 (m, 2H), and 2.51 (s, 3H). LCMS ES$^+$ 413 (M+1), 415 (M+3).

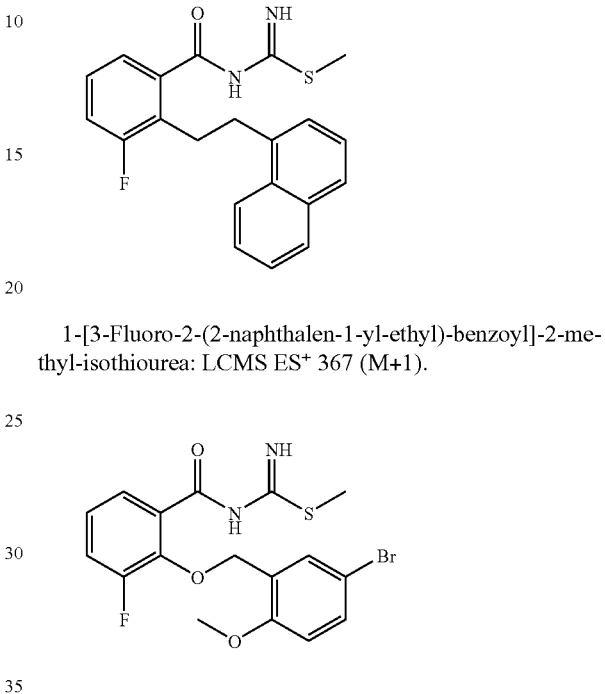

1-[3-Fluoro-2-(2-naphthalen-1-yl-ethyl)-benzoyl]-2-methyl-isothiourea: LCMS ES$^+$ 367 (M+1).

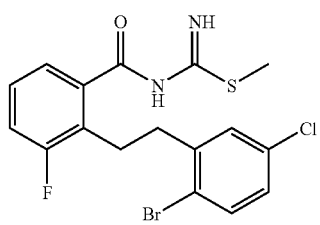

1-[2-(5-Bromo-2-methoxy-benzyloxy)-3-fluoro-benzoyl]-2-methyl-isothiourea: LCMS ES$^+$ 427 (M+1), 429 (M+3).

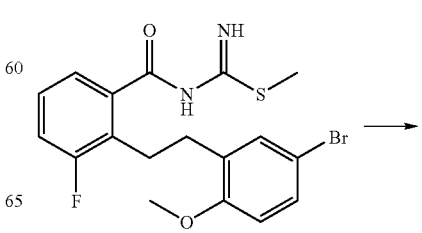

1-{2-[2-(2-bromo-5-chloro-phenyl)-ethyl]-3-fluorobenzoyl}-2-methyl-isothiourea: LCMS ES$^+$ 429 (M+1), 431 (M+3), 433 (M+5).

Method for Monosubstituted Acylguanidine Formation (General Method C)

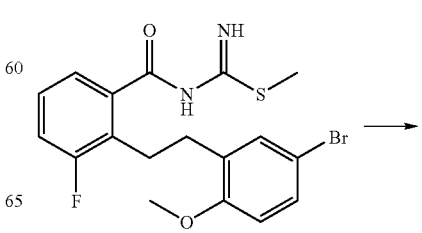

-continued

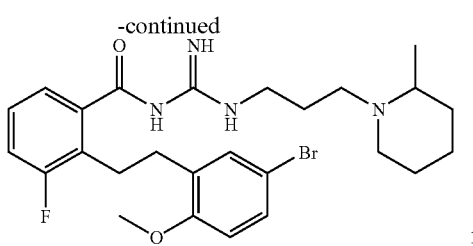

To a solution of 1-{2-[2-(5-bromo-2-methoxyphenyl)-ethyl]-3-fluorobenzoyl}-2-methylisothiourea (0.16 g, 0.38 mmol, 1 equiv) in o-xylene (1.7 mL) were added triethylamine (0.052 mL, 0.38 mmol, 1 equiv) and 1-(3-aminopropyl)-2-pipecoline (0.067 mL, 0.38 mmol, 1 equiv). The solution was allowed to stir at 145° C. for 4 hours and then cooled to room temperature. Hexanes (2 mL) and dichloromethane (2 mL) were added and the solution concentrated to a volume of about 0.5 mL. The residue was purified by column chromatography (SiO$_2$) to give the desired acylguanidine, which was characterized as its bisformate salt (0.089 g, 0.053 mmol, 37%).

Compound 1: N-{2-[2-(5-Bromo-2-methoxy-phenyl)-ethyl]-3-fluoro-benzoyl}-N'-[3-(2-methyl-piperidin-1-yl)-propyl]-guanidine, bisformate salt: $^1$H NMR (300 MHz, CDCl$_3$) δ 8.42 (s, 2H), 7.14-7.31 (m, 5H), 6.59-6.62 (m, 1H), 3.59 (s, 3H), 3.44-3.55 (m, 4H), 3.18-3.36 (m, 2H), 3.07-3.12 (m, 2H), 2.98-2.93 (m, 3H), 2.07-2.25 (m, 2H), 1.68-1.96 (m, 5H), 1.46-1.63 (m, 1H), and 1.37 (d, J=6.0 Hz, 3H). LCMS: ES$^+$ 533 (M+1), 535 (M+3); ES$^-$ 531 (M-1), 533 (M+1).

The following compounds were also prepared by General Method C:

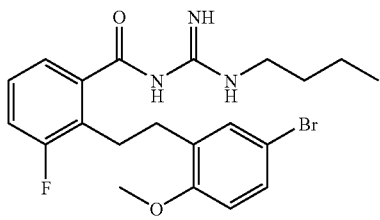

Compound 2: N-{2'-[2-(5-Bromo-2-methoxy-phenyl)-ethyl]-3-fluoro-benzoyl}-N'-butyl-guanidine, monoformate salt: $^1$H NMR (300 MHz, CDCl$_3$) δ 8.41 (s, 1H), 7.10-7.35 (m, 5H), 6.64 (d, J=8.4 Hz, 1H), 3.62 (s, 3H), 3.38 (t, J=7.2 Hz, 2H), 3.07-3.14 (m, 2H), 2.83-2.90 (m, 2H), 1.67-1.78 (m, 2H), 1.40-1.52 (m, 2H), and 0.99 (t, J=7.2 Hz, 3H). LCMS: ES$^+$ 450 (M+1), 452 (M+3); ES$^-$ 448 (M-1), 450 (M+1).

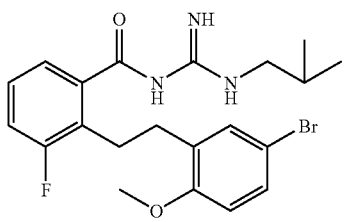

Compound 3: N-{2-[2-(5-Bromo-2-methoxy-phenyl)-ethyl]-3-fluoro-benzoyl}-N'-isobutyl-guanidine, monoformate salt: $^1$H NMR (300 MHz, CDCl$_3$) δ 8.42 (s, 1H), 7.16-7.37 (m, 5H), 6.64 (d, J=8.7 Hz, 1H), 3.62 (s, 3H), 3.18-3.23 (m, 2H), 3.06-3.12 (m, 2H), 2.82-2.89 (m, 2H), 1.97-2.10 (m, 1H), and 1.05 (t, J=6.6 Hz, 6H). LCMS: ES$^+$ 450 (M+1), 452 (M+3); ES$^-$ 448 (M-1), 450 (M+1).

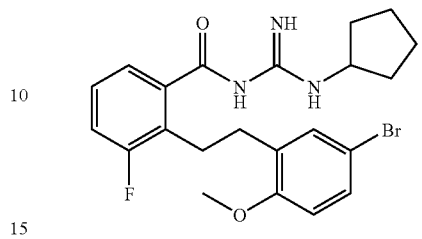

Compound 4: N-(2-[2-(5-Bromo-2-methoxy-phenyl)-ethyl]-3-fluoro-benzoyl)-N'-cyclopentyl-guanidine, monoformate salt: $^1$H NMR (300 MHz, CDCl$_3$) δ 8.37 (s, 1H), 7.16-7.35 (m, 5H), 6.65 (d, J=8.4 Hz, 1H), 3.96-4.07 (m, 1H), 3.62 (s, 3H), 3.05-3.13 (m, 2H), 2.81-2.86 (m, 2H), 2.06-2.21 (m, 2H), 1.77-1.87 (m, 2H), and 1.63-1.77 (m, 4H). LCMS: ES$^+$ 462 (M+1), 464 (M+3); ES$^-$ 460 (M-1), 462 (M+1)

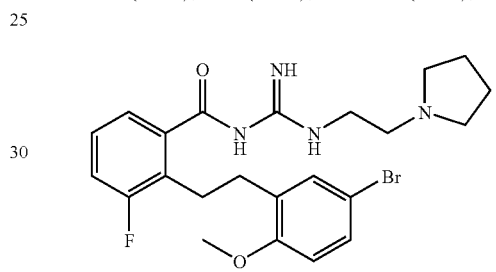

Compound 5: N-{2-[2-(5-Bromo-2-methoxy-phenyl)-ethyl]-3-fluoro-benzoyl}-N'-(2-pyrrolidin-1-yl-ethyl)-guanidine, monoformate salt: $^1$H NMR (300 MHz, CDCl$_3$) δ 8.46 (s, 1H), 7.15-7.36 (m, 5H), 6.64 (d, J=8.4 Hz, 1H), 3.57-3.64 (m, 5H), 3.11 (t, J=6.9 Hz, 2H), 3.04 (t, J=5.7 Hz, 2H), 2.82-2.96 (m, 6H), and 1.89-2.00 (m, 4H). LCMS: ES$^+$ 491 (M+1), 493 (M+3); ES$^-$ 489 (M-1), 491 (M+1).

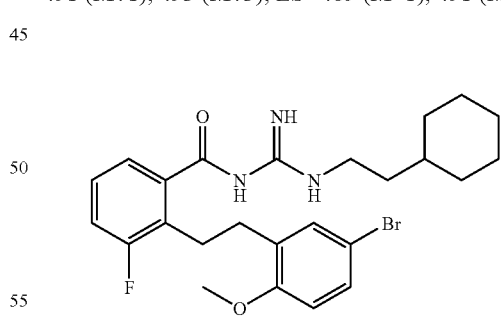

Compound 6: N-{2-[2-(5-Bromo-2-methoxy-phenyl)-ethyl]-3-fluoro-benzoyl}-N'-(2-cyclohexyl-ethyl)-guanidine, monoformate salt: $^1$H NMR (300 MHz, CDCl$_3$) δ 8.40 (s, 1H), 7.15-7.35 (m, 5H), 6.64 (d, J=8.4 Hz, 1H), 3.60 (s, 3H), 3.38 (t, J=7.2 Hz, 2H), 3.12 (t, J=7.2 Hz, 2H), 2.87 (t, J=7.2 Hz, 2H), 1.61-1.80 (m, 7H), 1.33-1.45 (m, 1H), 1.10-1.30 (m, 3H), and 0.89-1.15 (m, 2H). LCMS: ES$^+$ 504 (M+1), 506 (M+3); ES$^-$ 502 (M-1), 504 (M+1).

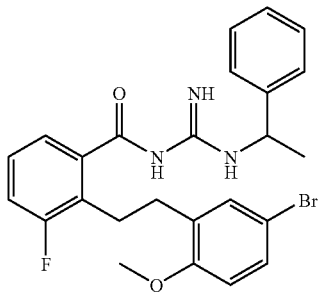

Compound 7: N-{2-[2-(5-Bromo-2-methoxy-phenyl)-ethyl]-3-fluoro-benzoyl}-N'-(1-phenyl-ethyl)-guanidine, bishydrochloride salt: $^1$H NMR (300 MHz, CDCl$_3$) δ 11.97 (br s, 1H), 10.45 (br s, 1H), 9.50 (br s, 1H), 7.61-7.70 (m, 1H), 7.29-7.50 (m, 5H), 7.16-7.26 (m, 4H), 6.73 (d, J=8.4 Hz, 1H), 4.87 (br s, 1H), 3.51 (s, 3H), 3.13-3.24 m, 2H), 2.85 (t, J=6.9 Hz, 2H), and 1.70 (d, J=6.9 Hz, 3H). LCMS: ES$^+$ 498 (M+1), 500 (M+3); ES$^-$ 496 (M−1), 498 (M+1)

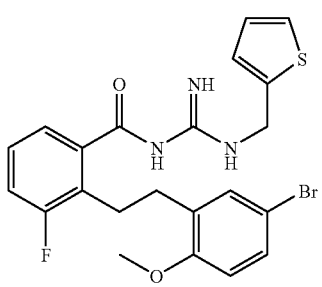

Compound 8: N-{2-[2-(5-Bromo-2-methoxy-phenyl)-ethyl]-3-fluoro-benzoyl}-N'-thiophen-2-ylmethyl-guanidine, bisformate salt: $^1$H NMR (300 MHz, CDCl$_3$) δ 8.15 (s, 2H), 7.35 (dd, J=5.1, 1.2 Hz, 1H), 7.14-7.19 (m, 6H), 7.03 (dd, J=5.1, 3.3 Hz, 1H), 6.59 (d, J=8.7 Hz, 1H), 4.78 (s, 2H), 3.50 (s, 3H), 3.09-3.13 (m, 2H), and 2.84 (t, J=7.2 Hz, 2H). LCMS: ES$^+$ 490 (M+1), 492 (M+3); ES$^-$ 488 (M−1), 490 (M+1).

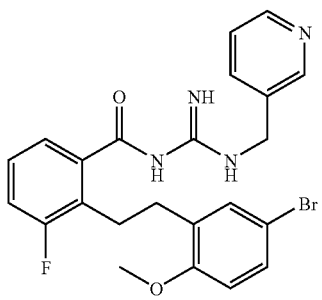

Compound 9: N-{2-[2-(5-Bromo-2-methoxy-phenyl)-ethyl]-3-fluoro-benzoyl}-N'-pyridin-3-ylmethyl-guanidine, bisformate salt: $^1$H NMR (300 MHz, CDCl$_3$) δ 8.74 (d, J=1.8 Hz, 1H), 8.63 (dd, J=4.8, 1.8 Hz, 1H), 8.19 (s, 2H), 7.91 (dt, J=7.5, 1.8 Hz, 1H), 7.18-7.32 (m, 5H), 6.60 (d, J=8.4 Hz, 1H), 4.68 (s, 2H), 3.51 (s, 3H), 3.14 (m, 2H), and 2.86 (t, J=7.2 Hz, 2H). LCMS: ES$^+$ 485 (M+1), 487 (M+3); ES$^-$ 483 (M−1), 485 (M+1).

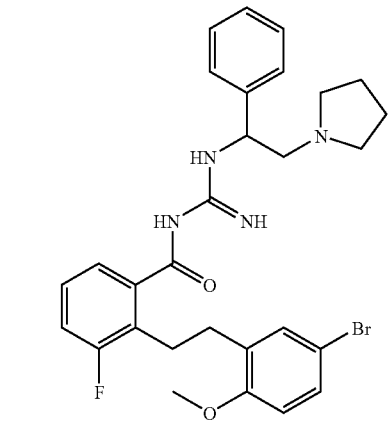

Compound 10: N-{2-[2-(5-Bromo-2-methoxy-phenyl)-ethyl]-3-fluoro-benzoyl}-N'-(1-phenyl-2-pyrrolidin-1-yl-ethyl)-guanidine, bisformate salt: $^1$H NMR (300 MHz, CDCl$_3$) δ 8.51 (s, 2H), 7.02-7.56 (m, 10H), 6.57 (d, J=8.1 Hz, 1H), 5.83 (br s, 1H), 3.60 (s, 3H), 2.92-3.26 (m, 8H), 2.77-2.89 (m, 2H), and 1.90-2.05 (br m, 4H). LCMS: ES$^+$ 567 (M+1), 569 (M+3); ES$^-$ 565 (M−1), 567 (M+1)

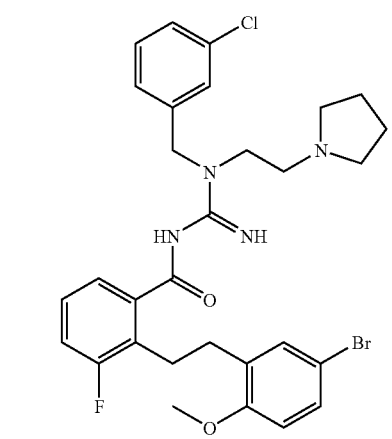

Compound 11: N'-{2-[2-(5-Bromo-2-methoxy-phenyl)-ethyl]-3-fluoro-benzoyl}-N-(3-chloro-benzyl)-N-(2-pyrrolidin-1-yl-ethyl)-guanidine, monoformate salt: $^1$H NMR (300 MHz, CDCl$_3$) δ 8.42 (s, 1H), 7.49 (dd, J=7.8, 0.9 Hz, 1H), 7.22-7.27 (m, 6H), 7.08-7.16 (m, 2H), 6.99 (m, 1H), 6.67 (m, 1H), 4.75 (s, 2H), 3.74 (s, 3H), 3.60-3.68 (m, 2H), 3.21-3.29 (m, 2H), 2.82-2.99 (m, 2H), and 1.87-1.97 (m, 4H). LCMS: ES$^+$ 615 (M+1), 617 (M+3); ES$^-$ 613 (M−1), 615 (M+1)

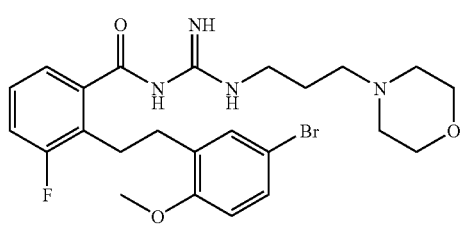

Compound 12: N-{2-[2-(5-Bromo-2-methoxy-phenyl)-ethyl]-3-fluoro-benzoyl}-N'-(3-morpholin-4-yl-propyl)-guanidine, bisformate salt: $^1$H NMR (300 MHz, CDCl$_3$) δ 8.36 (s, 2H), 7.18-7.36 (m, 5H), 6.65 (d, J=9.0 Hz, 1H), 3.82 (dd, J =4.8, 4.5 Hz, 4H), 3.61 (s, 3H), 3.43-3.49 (m, 2H), 3.08-3.16 (m, 2H), 2.82-2.92 (m, 2H), 2.58-2.72 (m, 6H), and 1.93-2.04 (m, 2H). LCMS: ES$^+$ 521 (M+1), 523 (M+3); ES$^-$ 519 (M−1), 521 (M+1).

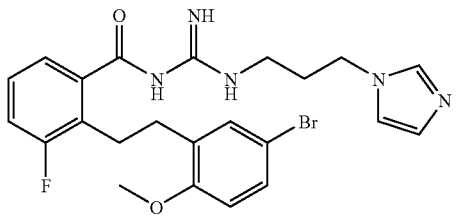

Compound 13: N-{2-[2-(5-Bromo-2-methoxy-phenyl)-ethyl]-3-fluoro-benzoyl}-N'-(3-imidazol-1-yl-propyl)-guanidine, monoformate salt: $^1$H NMR (300 MHz, CDCl$_3$) δ 8.43 (br s, 1H), 7.66 (br s, 1H), 7.15-7.35 (m, 6H), 7.01-7.13 (br m, 1H), 6.63 (d, 7=9.0 Hz, 1H), 4.12-4.22 (br m, 2H), 3.60 (s, 3H), 3.27-3.36 (m, 2H), 3.05-3.15 (m, 2H), 2.86 (t, J=7.2 Hz, 2H), and 2.18-2.32 (br m, 2H). LCMS: ES$^+$ 502 (M+1), 504 (M+3); ES$^-$ 500 (M−1), 502 (M+1).

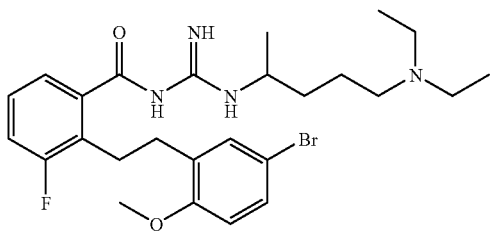

Compound 14: N-{2-[2-(5-Bromo-2-methoxy-phenyl)-ethyl]-3-fluoro-benzoyl}-N'-(4-diethylamino-1-methyl-butyl)-guanidine, bisformate salt: $^1$H NMR (300 MHz, CDCl$_3$) δ 8.46 (s, 2H), 7.13-7.36 (m, 5H), 6.64 (d, T=8.4 Hz, 1H), 3.78-3.90 (br m, 1H), 3.66 (s, 3H), 2.91-3.13 (m, 8H), 2.83-2.88 (m, 2H), 1.76-1.91 (m, 3H), 1.56-1.70 (m, 6H), 1.33 (d, J=5.1 Hz, 3H), and 1.26 (t, J=6.9 Hz, 2H). LCMS: ES$^+$ 535 (M+1), 537 (M+3); ES$^-$ 533 (M−1), 535. (M+1)

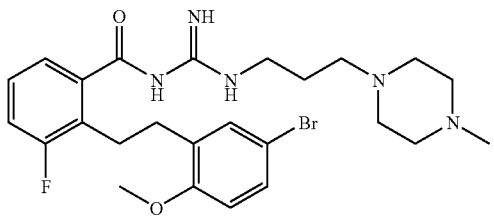

Compound 15: N-{2-[2-(5-Bromo-2-methoxy-phenyl)-ethyl]-3-fluoro-benzoyl}-N'-[3-(4-methyl-piperazin-1-yl)-propyl]-guanidine, bisformate salt: $^1$H NMR (300 MHz, CDCl$_3$) δ 8.35 (s, 2H), 7.17-7.40 (m, 5H), 6.60-6.71 (m, 1H), 3.58 (s, 3H), 3.38-3.49 (m, 2H), 3.05-3.20 (m, 2H), 2.83-2.98 (m, 8H), 2.72-2.81 (m, 2H), 2.58-2.60 (m, 2H), 2.45-2.57 (m, 3H), and 1.89-2.06 (m, 2H). LCMS: ES$^+$ 534 (M+1), 536 (M+3); ES$^-$ 532 (M−1), 534 (M+1).

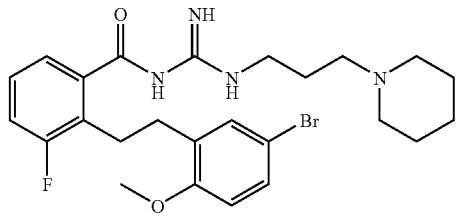

Compound 16: N-{2-[2-(5-Bromo-2-methoxy-phenyl)-ethyl]-3-fluoro-benzoyl}-N'-(3-piperidin-1-yl-propyl)-guanidine, bisformate salt: $^1$H NMR (300 MHz, CDCl$_3$) δ 8.42 (s, 2H), 7.21-7.47 (m, 5H), 6.60-6.71 (m, 1H), 3.60 (s, 3H), 3.44-3.56 (m, 2H), 3.04-3.25 (m, 2H), 2.75-3.02 (m, 8H), 2.06-2.23 (m, 2H), 1.78-1.97 (m, 4H), and 1.51-1.72 (m, 3H). LCMS: ES$^+$ 519 (M+1), 521 (M+3); ES$^-$ 517 (M−1), 519 (M+1)

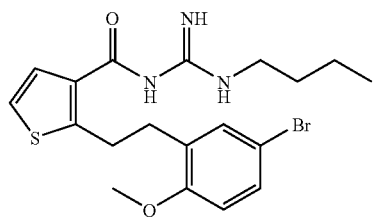

Compound 17: N-{2-[2-(5-Bromo-2-methoxy-phenyl)-ethyl]-thiophene-3-carbonyl}-N'-butyl-guanidine, monoformate salt: $^1$H NMR (300 MHz, CD$_3$OD) δ 8.47 (s, 1H), 7.38 (d, J=5.7 Hz, 1H), 7.27 (dd, J=8.4, 2.4 Hz, 2H), 7.12 (d, J=2.4 Hz, 1H), 6.81 (d, J=8.7 Hz, 1H), 3.76 (s, 3H), 3.44 (t, J=7.2 Hz, 2H), 3.33 (t, J=7.2 Hz, 2H), 2.94 (t, J=7.2 Hz, 2H), 1.61-1.74 (m, 2H), 1.40-1.53 (m, 2H), and 1.00 (t, J=7.2 Hz, 3H). LCMS: ES$^+$ 438 (M+1), 440 (M+3); ES$^-$ 436 (M−1), 438 (M+1)

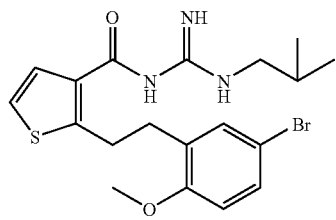

Compound 18: N-{2-[2-(5-Bromo-2-methoxy-phenyl)-ethyl]-thiophene-3-carbonyl}-N'-isobutyl-guanidine, monoformate salt: $^1$H NMR (300 MHz, CD$_3$OD) δ 8.49 (s, 1H), 7.39 (d, J=5.4 Hz, 1H), 7.24-7.30 (m, 2H), 7.09-7.13 (m, 1H), 6.80 (d, J=8.7 Hz, 1H), 3.75 (s, 3H), 3.42-3.51 (m, 2H), 3.15 (d, J=6.9 Hz, 2H), 2.93 (t, J=7.2 Hz, 2H), 1.90-2.04 (m, 1H), and 1.03 (t, J=6.3 Hz, 6H). LCMS: ES$^+$ 438 (M+1), 440 (M+3); ES$^-$ 436 (M−1), 438 (M+1)

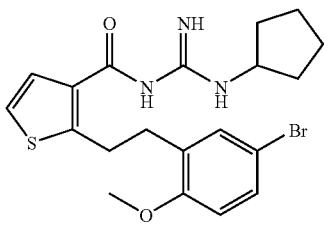

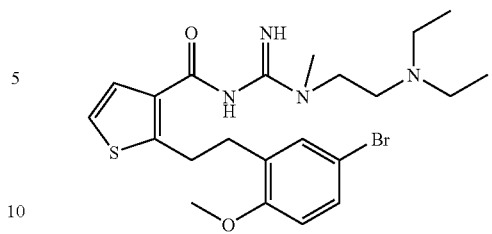

Compound 19: N-{2-[2-(5-Bromo-2-methoxy-phenyl)-ethyl]-thiophene-3-carbonyl}-N'-cyclopentyl-guanidine, monoformate salt: $^1$H NMR (300 MHz, CD$_3$OD) δ 8.48 (s, 1H), 7.37 (d, J=5.4 Hz, 1H), 7.26 (dd, J=8.4, 2.4 Hz, 2H), 7.11 (d, J=2.4 Hz, 1H), 6.81 (d, J=8.4 Hz, 1H), 3.94-4.08 (m, 1H), 3.78 (s, 3H), 3.44 (t, J=7.2 Hz, 2H), 2.93 (t, J=7.2 Hz, 2H), 2.00-2.17 (m, 2H), and 1.61-1.86 (m, 6H). LCMS: ES$^+$ 450 (M+1), 452 (M+3); ES$^-$ 448 (M−1), 450 (M+1)

Compound 22: N'-{2-[2-(5-Bromo-2-methoxy-phenyl)-ethyl]-thiophene-3-carbonyl}-N-(2-diethylamino-ethyl)-N-methyl-guanidine, monoformate salt: $^1$H NMR (300 MHz, CD$_3$OD) δ 8.47 (s, 1H), 7.31 (d, J=5.4 Hz, 1H), 7.22 (dd, J=8.7, 2.1 Hz, 1H), 7.11 (d, J=2.1 Hz, 1H), 7.04 (d, J=5.1 Hz, 1H), 6.79 (d, J=8.7 Hz, 1H), 3.77-3.87 (m, 2H), 3.75 (s, 3H), 3.36-3.43 (m, 2H), 3.01-3.07 (m, 2H), 3.01 (s, 3H), 2.84-2.95 (m, 6H), and 1.00 (t, J=6.9 Hz, 3H). LCMS: ES$^+$ 495 (M+1), 497 (M+3).

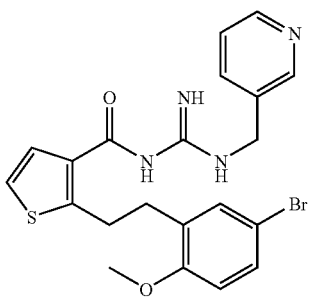

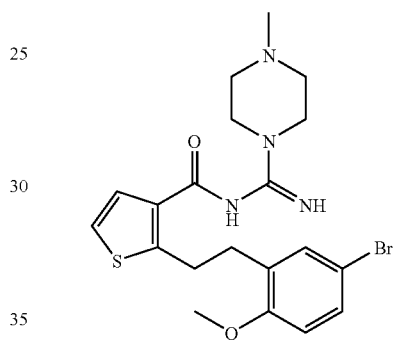

Compound 20: N-{2-[2-(5-Bromo-2-methoxy-phenyl)-ethyl]-thiophene-3-carbonyl}-N'-pyridin-3-ylmethyl-guanidine, monoformate salt: $^1$H NMR (300 MHz, CD$_3$OD) δ 8.59 (br s, 1H), 8.51 (br s, 1H), 8.34 (s, 1H), 7.89 (br s, 1H), 7.48 (br s, 1H), 7.37 (d, J=5.7 Hz, 1H), 7.25 (dd, J=8.4, 2.4 Hz, 2H), 7.10-7.14 (m, 1H), 6.79 (d, J=8.4 Hz, 1H), 4.63 (br s, 2H), 3.75 (s, 3H), 3.41-3.51 (m, 2H), 3.30-3.35 (m, 2H), and 2.79-2.99 (m, 2H). LCMS: ES$^+$ 473 (M+1), 475 (M+3); ES$^-$ 471 (M−1), 473 (M+1).

Compound 23: 2-[2-(5-Bromo-2-methoxy-phenyl)-ethyl]-thiophene-3-carboxylic acid [imino-(4-methyl-piperazin-1-yl)-methyl]-amide, bisformate salt: $^1$H NMR (300 MHz, CD$_3$OD) δ 8.35 (s, 2H), 7.41 (d, J=5.4 Hz, 1H), 7.27 (dd, J=8.7, 2.1 Hz, 1H), 7.16 (d, J=2.1 Hz, 1H), 7.03 (d, J=5.7 Hz, 1H), 6.83 (d, J=8.7 Hz, 1H), 3.72-3.86 (m, 7H), 3.45-3.53 (m, 2H), 2.88-2.99 (m, 2H), 2.74-2.82 (m, 4H), and 2.54 (s, 3H). LCMS: ES$^+$ 465 (M+1), 467 (M+3); ES$^-$ 463. (M−1), 465 (M+1).

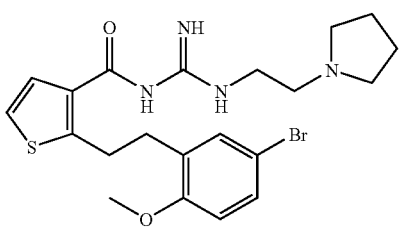

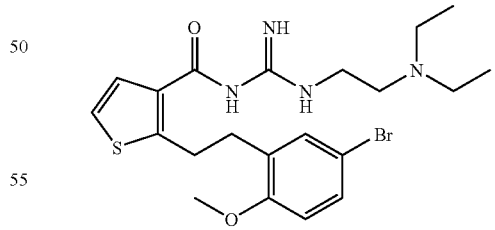

Compound 21: N-{2-[2-(5-Bromo-2-methoxy-phenyl)-ethyl]-thiophene-3-carbonyl}-N'-(2-pyrrolidin-1-yl-ethyl)-guanidine, bisformate salt: $^1$H NMR (300 MHz, CD$_3$OD) δ 8.39 (s, 2H), 7.39 (d, J=5.4 Hz, 1H), 7.28 (dd, J=8.7, 2.4 Hz, 2H), 7.12-7.21 (m, 1H), 6.84 (d, J=8.7 Hz, 1H), 3.76 (s, 3H), 3.61-3.68 (m, 2H), 3.39-3.47 (m, 2H), 3.10-3.28 (m, 6H), 2.94 (t, J=7.5 Hz, 2H), and 1.80-1.97 (m, 4H). LCMS: ES$^+$ 479 (M+1), 481 (M+3); ES$^-$ 477 (M−1), 479 (M+1).

Compound 24: N-{2-[2-(5-Bromo-2-methoxy-phenyl)-ethyl]-thiophene-3-carbonyl}-N'-(2-diethylamino-ethyl)-guanidine, monoformate salt: $^1$H NMR (300 MHz, CDCl$_3$) δ 8.63 (s, 1H), 7.75 (d, J=5.4 Hz, 1H), 7.23-7.29 (m, 2H), 7.11 (d, J=5.4 Hz, 1H), 6.69 (d, J=8.4 Hz, 1H), 3.75 (s, 3H), 3.42-3.49 (m, 2H), 3.36-3.42 (m, 2H), 2.90-2.98 (m, 2H), 2.72-2.80 (m, 2H), 2.67 (q, J=7.2 Hz, 4H), and 1.11 (t, J=7.2 Hz, 6H). LCMS: ES$^+$ 481 (M+1), 483 (M+3); ES$^-$ 479 (M−1) 481 (M+1).

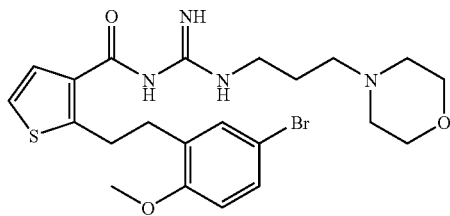

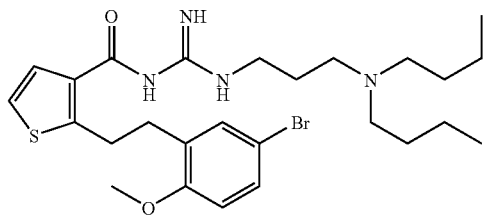

Compound 25: N-{2-[2-(5-Bromo-2-methoxy-phenyl)-ethyl]-thiophene-3-carbonyl}-N'-(3-morpholin-4-yl-propyl)-guanidine, monoformate salt: $^1$H NMR (300 MHz, CDCl$_3$) δ 8.52 (s, 1H), 7.71 (d, J=5.4 Hz, 1H), 7.22-7.28 (m, 2H), 7.11 (d, J=5.4 Hz, 1H), 6.68 (d, J=8.4 Hz, 1H), 3.65-3.78 (m, 7H), 3.33-3.42 (m, 4H), 2.90-2.97 (m, 2H), 2.46-2.57 (m, 6H), and 1.06-1.94 (m, 2H). LCMS: ES$^+$ 509 (M+1), 511 (M+3); ES$^-$ 507 (M−1), 509 (M+1).

Compound 28: N-{2-[2-(5-Bromo-2-methoxy-phenyl)-ethyl]-thiophene-3-carbonyl}-N'-(3-dibutylamino-propyl)-guanidine, monoformate salt: $^1$H NMR (300 MHz, CDCl$_3$) δ 8.65 (s, 1H), 7.71 (d, J=4.8 Hz, 1H), 7.25-7.29 (m, 2H), 7.08 (d, J=5.4 Hz, 1H), 6.69 (d, J=9.0 Hz, 1H), 3.75 (s, 3H), 3.34-3.45 (m, 4H), 2.92-3.00 (m, 2H), 2.48-2.64 (m, 6H), 1.81-1.92 (m, 2H), 1.39-1.52 (m, 4H), 1.24-1.38 (m, 4H), and 0.94 (t, J=7.2 Hz, 6H). LCMS: ES$^+$ 551 (M+1), 553 (M+3); ES$^-$ 549 (M−1), 551 (M+1).

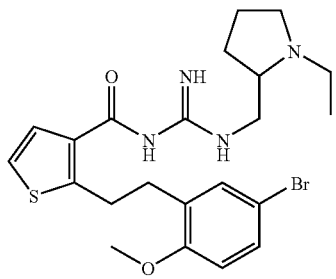

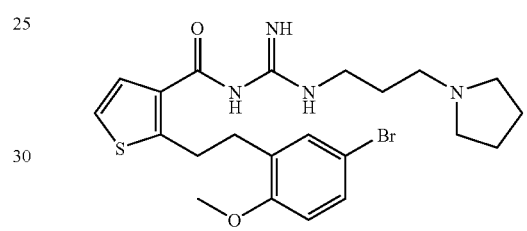

Compound 26: N-{2-[2-(5-Bromo-2-methoxy-phenyl)-ethyl]-thiophene-3-carbonyl}-N'-(1-ethyl-pyrrolidin-2-ylmethyl)-guanidine, monoformate salt: $^1$H NMR (300 MHz, CDCl$_3$) δ 8.62 (s, 1H), 7.76 (d, J=5.7 Hz, 1H), 7.24-7.29 (m, 2H), 7.11 (d, J=5.4 Hz, 1H), 6.69 (d, J=8.7 Hz, 1H), 3.75 (s, 3H), 3.35-3.57 (m, 4H), 3.12-3.24 (m, 1H), 2.92-3.00 (m, 4H), 2.39-2.54 (m, 1H), 2.30-2.38 (m, 1H), 1.70-2.04 (m, 4H), and 1.17 (t, J=6.9 Hz, 3H). LCMS: ES$^+$ 493 (M+1), 495 (M+3); ES$^-$ 491 (M−1), 493 (M+1)

Compound 29: N-{2-[2-(5-Bromo-2-methoxy-phenyl)-ethyl]-thiophene-3-carbonyl}-N'-(3-pyrrolidin-1-yl-propyl)-guanidine, monoformate salt: $^1$H NMR (300 MHz, CDCl$_3$) δ 8.59 (s, 1H), 7.72 (d, J=5.4 Hz, 1H), 7.27 (dd, J=8.1, 2.1 Hz, 1H), 7.23 (d, J=2.1 Hz, 1H), 7.11 (d, J=5.1 Hz, 1H), 6.69 (d, J=8.4 Hz, 1H), 3.75 (s, 3H), 3.48 (t, J=6.9 Hz, 2H), 3.33-3.42 (m, 2H), 2.76-2.98 (m, 8H), and 1.87-2.06 (m, 6H). LCMS: ES$^+$ 493 (M+1), 495 (M+3); ES$^-$ 491 (M−1), 493 (M+1)

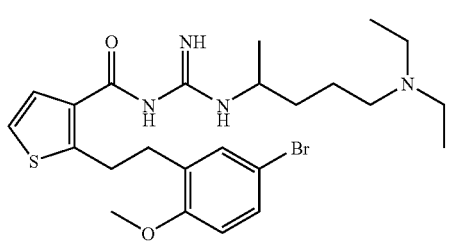

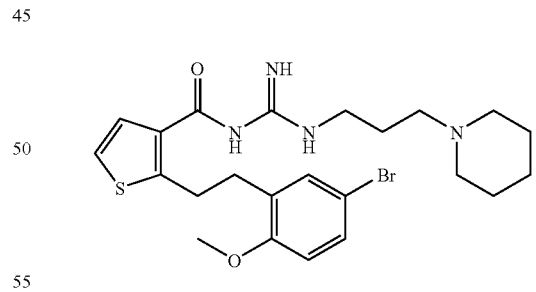

Compound 27: N-{2-[2-(5-Bromo-2-methoxy-phenyl)-ethyl]-thiophene-3-carbonyl}-N'-(4-diethylamino-1-methyl-butyl)-guanidine, bisformate salt: $^1$H NMR (300 MHz, CDCl$_3$) δ 8.60 (s, 2H), 7.56-7.72 (m, 1H), 7.22-7.27 (m, 2H), 7.05-7.11 (m, 1H), 6.67 (d, J=8.7 Hz, 1H), 3.75 (s, 3H), 3.28-3.43 (m, 2H), 2.70-2.98 (m, 9H), 1.65-1.87 (m, 3H), 1.50-1.65 (m, 1H), 1.25-1.38 (m, 3H), and 1.18 (t, J=6.9 Hz, 6H). LCMS: ES$^+$ 423 (M+1), 425 (M+3); ES$^-$ 421 (M−1), 423 (M+1)

Compound 30: N-{2-[2-(5-Bromo-2-methoxy-phenyl)-ethyl]-thiophene-3-carbonyl}-N'-(3-piperidin-1-yl-propyl)-guanidine, bisformate salt: $^1$H NMR (300 MHz, CDCl$_3$) δ 8.49 (s, 2H), 7.66 (d, J=5.7 Hz, 1H), 7.23 (dd, J=8.4, 2.1 Hz, 1H), 7.20 (d, J=2.1 Hz, 1H), 7.09 (d, J=5.4 Hz, 1H), 6.66 (d, J=8.4 Hz, 1H), 3.75 (s, 3H), 3.44 (t, J=7.2 Hz, 2H), 3.33-3.39 (m, 2H), 2.89-2.94 (m, 2H), 2.75-2.82 (m, 6H), 1.97-2.11 (m, 2H), 1.73-1.85 (m, 4H), and 1.52-1.63 (m, 2H). LCMS: ES$^+$ 507 (M+1), 509 (M+3); ES$^-$ 505 (M−1), 507 (M+1).

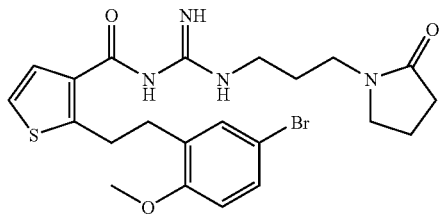

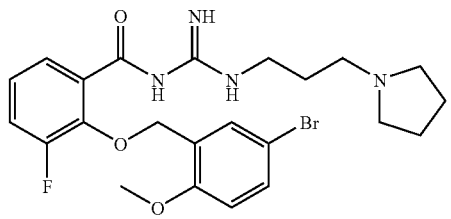

Compound 31: N-{2-[2-(5-Bromo-2-methoxy-phenyl)-ethyl]-thiophene-3-carbonyl}-N'-[3-(2-oxo-pyrrolidin-1-yl)-propyl]-guanidine, monoformate salt: $^1$H NMR (300 MHz, CDCl$_3$) δ 8.62 (s, 1H), 7.71 (d, J=5.4 Hz, 1H), 7.24-7.30 (m, 2H), 7.12 (d, J=5.1 Hz, 1H), 6.70 (d, J=8.4 Hz, 1H), 3.77 (s, 3H), 3.47 (t, J=7.2 Hz, 2H), 3.36-3.43 (m, 6H), 2.95 (t, J=7.2 Hz, 2H), 2.45 (t, J=7.2 Hz, 2H), 2.09 (p, J=7.2 Hz, 2H), and 1.91-1.99 (m, 2H). LCMS: ES$^+$ 507 (M+1), 509 (M+3); ES$^-$ 505 (M−1), 507 (M+1).

Compound 34: N-[2-(5-Bromo-2-methoxy-benzyloxy)-3-fluoro-benzoyl]-N'-(3-pyrrolidin-1-yl-propyl)-guanidine, bisformate salt: $^1$H NMR (300 MHz, CDCl$_3$) δ 8.41 (s, 2H), 7.56-7.64 (m, 1H), 7.22-7.39 (m, 3H), 7.05-7.17 (m, 1H), 6.69 (d, J=8.7 Hz, 1H), 5.26 (s, 2H), 3.68 (s, 3H), 3.54 (t, J=6.9 Hz, 2H), 3.08-3.25 (m, 4H), 3.03 (t, J=6.3 Hz, 2H), and 1.92-2.20 (m, 6H). LCMS: ES$^+$ 507 (M+1), 509 (M+3)

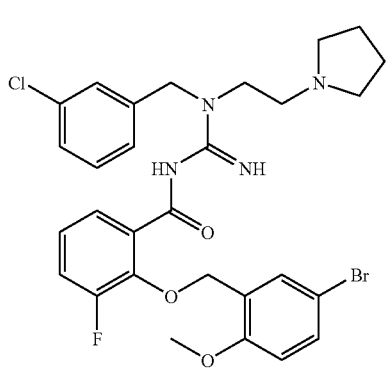

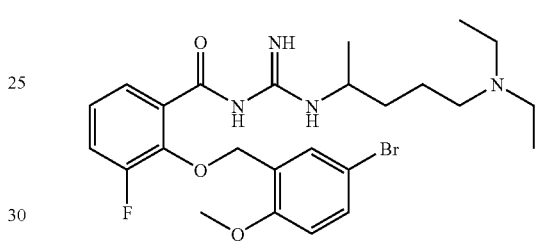

Compound 32: N'-[2-(5-Bromo-2-methoxy-benzyloxy)-3-fluoro-benzoyl]-N-(3-chloro-benzyl)-N-(2-pyrrolidin-1-yl-ethyl)-guanidine, monoformate salt: $^1$H NMR (300 MHz, CDCl$_3$) δ 8.40 (s, 1H), 7.69 (d, J=2.1 Hz, 1H), 7.46 (d, J=7.5 Hz, 1H), 7.37 (dd, J=8.7, 2.4 Hz, 1H), 7.21-7.29 (m, 1H), 7.18 (s, 1H), 6.98-7.13 (m, 4H), 6.71 (d, J=8.7 Hz, 1H), 5.10 (s, 2H), 4.67 (s, 2H), 3.74 (s, 3H), 3.57-3.71 (m, 2H), 2.81-3.14 (m, 6H), and 1.78-2.02 (m, 4H). LCMS: ES$^+$ 617 (M+1), 619 (M+3), 621 (M+5); ES$^-$ 615 (M−1), 617 (M+1), 617 (M+3)

Compound 35: N-[2-(5-Bromo-2-methoxy-benzyloxy)-3-fluoro-benzoyl]-N'-(4-diethylamino-1-methyl-butyl)-guanidine, bisformate salt: $^1$H NMR (300 MHz, CDCl$_3$) δ 8.45 (s, 2H), 7.59-7.64 (m, 1H), 7.20-7.39 (m, 3H), 7.05-7.17 (m, 1H), 6.71 (d, J=9.0 Hz, 1H), 5.25 (s, 2H), 3.76-3.89 (m, 1H), 3.70 (s, 3H), 3.01 (q, J=7.2 Hz, 4H), 2.84-2.96 (m, 2H), 1.70-1.94 (m, 3H), 1.50-1.68 (m, 1H), and 1.14-1.38 (m, 9H). LCMS: ES$^+$ 537 (M+1), 539 (M+3).

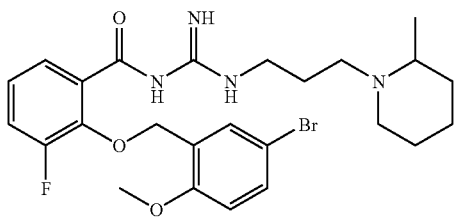

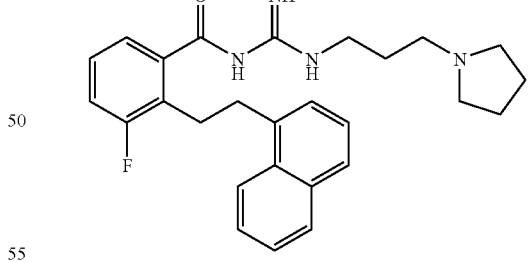

Compound 33: N-[2-(5-Bromo-2-methoxy-benzyloxy)-3-fluoro-benzoyl]-N'-[3-(2-methyl-piperidin-1-yl)-propyl]-guanidine, bisformate salt: $^1$H NMR (300 MHz, CDCl$_3$) δ 8.48 (s, 2H), 7.63 (s, 1H), 7.20-7.39 (m, 3H), 7.05-7.18 (m, 1H), 6.70 (d, J=8.7 Hz, 1H), 5.25 (s, 2H), 3.69 (s, 3H), 3.27-3.55 (m, 2H), 2.85-3.15 (m, 3H), 2.47-2.66 (m, 2H), 1.89-2.08 (m, 2H), 1.58-1.87 (m, 4H), 1.39-1.57 (m, 2H), and 1.09-1.29 (m, 3H). LCMS: ES$^+$ 535 (M+1), 537 (M+3)

Compound 36: N-[3-Fluoro-2-(2-naphthalen-1-yl-ethyl)-benzoyl]-N'-(3-pyrrolidin-1-yl-propyl)-guanidine, bisformate salt: $^1$H NMR (300 MHz, CDCl$_3$) δ 8.45 (s, 2H), 8.20 (d, J=8.4 Hz, 1H), 7.83 (d, J=7.2 Hz, 1H), 7.70 (d, J=8.2 Hz, 1H), 7.41-7.59 (m, 2H), 7.10-7.42 (m, 5H), 3.42-3.61 (m, 2H), 3.32-3.42 (m, 2H), 3.18-3.32 (m, 2H), 2.95-3.14 (m, 4H), 2.85-2.95 (m, 2H), and 1.84-2.19 (m, 2H). LCMS: ES$^+$ 447 (M+1).

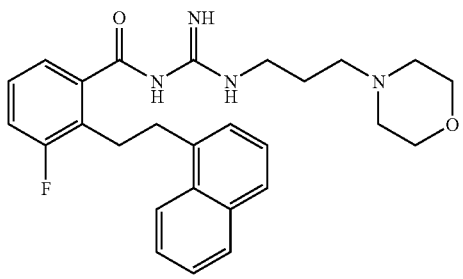

Compound 37: N-[3-Fluoro-2-(2-naphthalen-1-yl-ethyl)-benzoyl]-N'-(3-morpholin-4-yl-propyl)-guanidine, bisformate salt: $^1$H NMR (300 MHz, CDCl$_3$) δ 8.33 (s, 2H), 8.18 (d, J=8.1 Hz, 1H), 7.83 (d, J=7.8 Hz, 1H), 7.70 (d, J=8.2 Hz, 1H), 7.45-7.57 (m, 2H), 7.21-7.40 (m, 4H), 7.17 (d, J=6.9 Hz, 1H), 3.67-3.93 (m, 4H), 3.19-3.44 (m, 6H), 2.40-2.73 (m, 6H), and 1.79-1.99 (m, 2H). LCMS: ES$^+$ 463 (M+1).

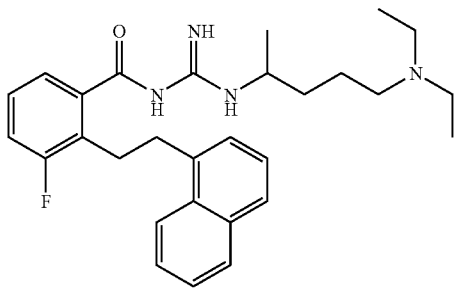

Compound 38: N-(4-Diethylamino-1-methyl-butyl)-N'-[3-fluoro-2-(2-naphthalen-1-yl-ethyl)-benzoyl]-guanidine, bisformate salt: $^1$H NMR (300 MHz, CDCl$_3$) δ 8.28 (s, 2H), 8.20 (d, J=7.8 Hz, 1H), 7.84 (d, J=7.8 Hz, 1H), 7.70 (d, J=8.1 Hz, 1H), 7.12-7.61 (m, 7H), 3.88-4.11 (m, 1H), 3.31-3.46 (m, 2H), 3.18-3.32 (m, 2H), 2.89-3.20 (m, 6H), 1.75-2.05 (m, 3H), 1.51-1.75 (m, 1H), and 0.99-1.48 (m, 9H). LCMS: ES$^+$ 477 (M+1).

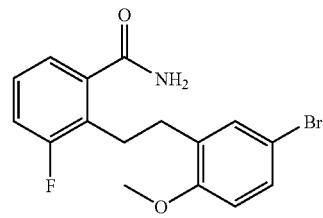

Compound 39: N-{2-[2-(2-Bromo-5-chloro-phenyl)-ethyl]-3-fluoro-benzoyl}-N'-[3-(2-methyl-piperidin-1-yl)-propyl]-guanidine, bisformate salt: $^1$H NMR (300 MHz, CDCl$_3$) δ 8.46 (s, 2H), 7.43 (d, J=8.4 Hz, 1H), 7.27-7.39 (m; 2H), 7.25-7.15 (m, 2H), 7.03 (dd, J=8.4, 2.4 Hz, 1H), 3.36-3.67 (m, 3H), 3.36-3.67 (m, 2H), 2.98-3.16 (m, 4H), 2.70-2.84 (m, 2H), 1.98-2.24 (m, 2H), 1.65-1.98 (m, 5H), 1.42-1.64 (m, 1H), and 1.36 (d, J=6.6 Hz, 3H). LCMS: ES$^+$ 537 (M+1), 539 (M+3), 541 (M+5).

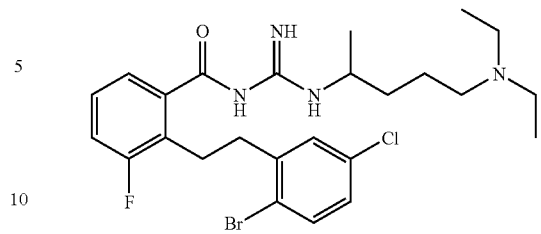

Compound 40: N-{2-[2-(2-Bromo-5-chloro-phenyl)-ethyl]-3-fluoro-benzoyl}-N'-(4-diethylamino-1-methyl-butyl)-guanidine, bisformate salt: $^1$H NMR (300 MHz, CDCl$_3$) δ 8.43 (s, 2H), 7.28-7.46 (m, 3H), 7.15-7.25 (m, 2H), 7.03 (dd, J=8.4, 2.4 Hz, 1H), 3.75-4.01 (m, 1H), 2.85-3.16 (m, 10H), 1.76-1.96 (m, 3H), 1.47-1.75 (m, 1H), and 1.15-1.39 (m, 9H). LCMS: ES$^+$ 539 (M+1), 541 (M+3), 543 (M+5).

N, N'-Disubstituted Acylguanidines

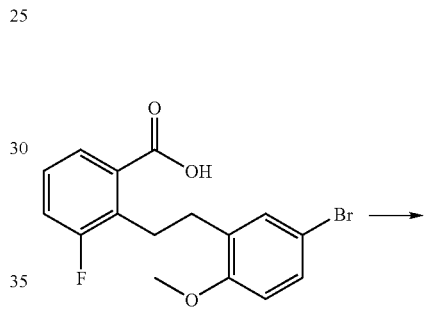

To a solution of 2-[2-(5-bromo-2-methoxyphenyl)-ethyl]-3-fluorobenzoic acid (1.78 g, 5.1 mol, 1 equiv) in DMF (6 mL) at room temperature were added diisopropylethylamine (DIPEA) (1.95 mL, 11.2 mmol, 2.2 equiv) and fluoro-N,N,N'-tetramethylformamidinium hexafluorophosphate (TFFH) (1.48 g, 5.6 mmol, 1.1 equiv). The homogeneous solution was allowed to stir for 1.5 hr, during which time the color changed to green. Ammonia gas was bubbled into the solution and the color changed to yellow and a precipitate was formed. The heterogeneous slurry was allowed to stir for 5 hr and then diluted with H$_2$O and ethyl acetate. The phases were separated and the organic portion was washed with brine, dried over MgSO$_4$, filtered and concentrated to give 2-[2-(5-bromo-2-methoxyphenyl)-ethyl]-3-fluorobenzamide in quantitative yield. The crude product was used without further purification. LCMS ES$^+$ 352 (M+1), 354 (M+3).

Method for N,N'-Disubstituted Acylguanidine Formation (General Method D)

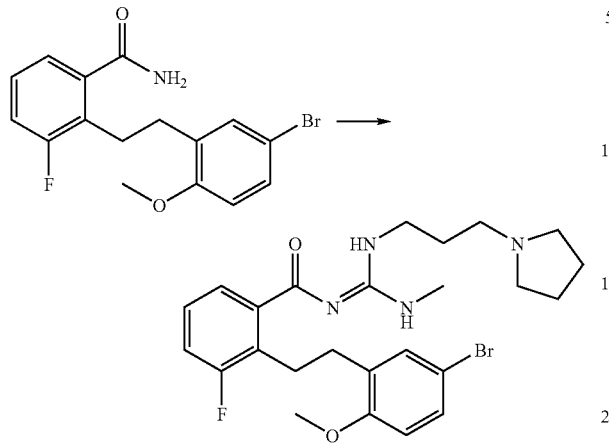

To a solution of 2-[2-(5-bromo-2-methoxyphenyl)-ethyl]-3-fluorobenzamide (0.117 g, 0.33 mmol, 1 equiv) in DMF (0.66 mL) at room temperature was added sodium hydride (60 wt %, 0.016 g, 0.43 mmol, 1.3 equiv). The solution was allowed to stir for 5 min, during which time gas evolved. Methyl isothiocyanate (0.019 mL, 0.27 mmol, 0.83 equiv) was added and the solution was heated at 60° C. for 30 min. After cooling to room temperature, 1-(3-aminopropyl)-pyrrolidine (0.042 mL. 0.33 mmol, 1 equiv) and mercury (II) chloride (0.089 g, 0.33 mmol, 1 equiv) were added sequentially. The black mixture was allowed to stir at room temperature for 10 min and then filtered through celite. The filtrate was concentrated to give a white solid. The crude product was purified (SiO$_2$, O-5% methanol in dichloromethane) to give the desired acylguanidine as a white solid (0.044 g, 0.09 mmol, 26%).

Compound 41: N-{2-[2-(5-Bromo-2-methoxy-phenyl)-ethyl]-3-fluoro-benzoyl}-N'-methyl-N''-(3-pyrrolidin-1-yl-propyl)-guanidine: $^1$H NMR (300 MHz, d$_6$-DMSO, 120° C.) δ 7.53 (d, J=3.9 Hz, 1H), 7.30 (dd, J=6.9, 0.9 Hz, 1H), 7.26 (m, 1H), 7.19 (d, J=1.2 Hz, 1H), 7.15 (t, J=4.5 Hz, 1H), 6.90 (d, J=9.0 Hz, 1H), 3.77 (s, 3H), 3.48 (t, J=3.3 Hz, 2H), 3.24 (br s, 4H), 3.18 (dd, J=6.3, 3.9 Hz, 4H), 2.95 (s, 3H), 2.85 (t, J=7.8 Hz, 2H), 2.02 (ddd, J=3.0, 3.0, 3.0 Hz, 2H), and 1.94-1.96 (m, 4H). LCMS: ES$^+$ 519 (M+1), 521 (M+3); ES$^-$ 517 (M−1), 519 (M+1)

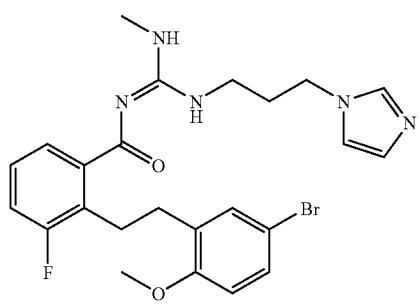

Compound 42: N-{2-[2-(5-Bromo-2-methoxy-phenyl)-ethyl]-3-fluoro-benzoyl}-N'-(3-imidazol-1-yl-propyl)-N''-methyl-guanidine, bishydrochloride salt: $^1$H NMR (300 MHz, CD$_3$OD) δ 9.03 (s, 1H), 7.72 (s, 1H), 7.61 (s, 1H), 7.38-7.53 (br s, 2H), 7.26-7.35 (m, 2H), 7.18 (d, J=3.0 Hz, 1H), 6.85 (d, J=8.7 Hz, 1H), 4.42 (br s, 1H), 3.78 (s, 3H), 3.52 (t, J=5.4 Hz, 2H), 3.23 (d, J=3.0 Hz, 1H), 3.04-3.11 (m, 5H), 2.88 (t, J=6.0 Hz, 2H), and 2.33 (t, J=6.0 Hz, 2H). LCMS: ES$^+$ 547 (M+1), 549 (M+3); ES$^-$ 545 (M−1), 547 (M+1)

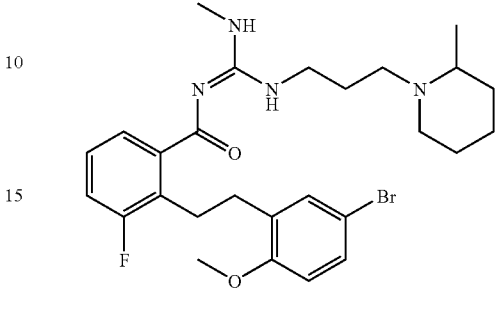

Compound 43: N-{2-[2-(5-Bromo-2-methoxy-phenyl)-ethyl]-3-fluoro-benzoyl}-N'-methyl-N''-[3-(2-methyl-piperidin-1-yl)-propyl]-guanidine, bishydrochloride salt: $^1$H NMR (300 MHz, CD$_3$OD) δ 7.51 (d, J=8.1 Hz, 1H), 7.37-7.44 (m, 1H), 7.31 (d, J=8.7 2H), 7.18 (br s, 1H), 6.85 (d, J=8.7 Hz, 1H), 3.78 (s, 3H), 3.55 (t, J=4.8 Hz, 2H), 3.07 (br s, 2H), 2.97 (s, 3H), 2.85 (s, 3H), 2.80 (s, 1H), and 2.68 (br s, 14H). LCMS: ES$^+$ 549 (M+1), 551 (M+3); ES$^-$ 547 (M−1), 549 (M+1).

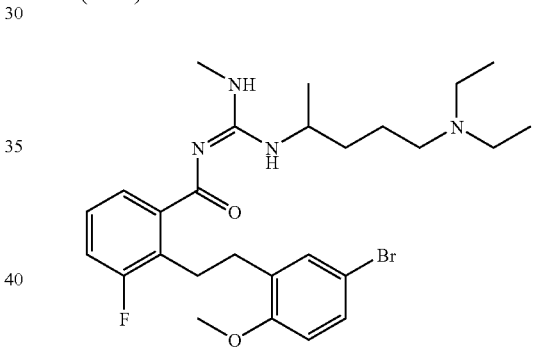

Compound 44: N-{2-[2-(5-Bromo-2-methoxy-phenyl)-ethyl]-3-fluoro-benzoyl}-N'-(4-diethylamino-1-methyl-butyl)-N''-methyl-guanidine guanidine: $^1$H NMR (300 MHz, CD$_3$OD) δ 7.37-7.54 (m, 2H), 7.32 (d, J=8.1 Hz, 2H), 7.20 (s, 1H), 6.88 (d, J=8.1 Hz, 1H), 3.81 9 (s, 3H), 3.21 (br s, 6H), 3.10 (br s, 5H), 2.89 (d, J=6.6 Hz, 2H), 1.77 (br s, 3H), and 1.26-1.42 (m, 11H). LCMS: ES$^+$ 549 (M+1), 551 (M+3); ES$^-$ 547 (M−1), 549 (M+1).

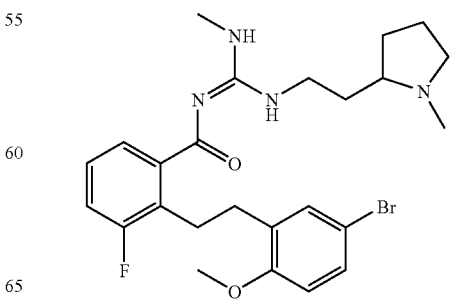

Compound 45: N-{2-[2-(5-Bromo-2-methoxy-phenyl)-ethyl]-3-fluoro-benzoyl}-N'-methyl-N''-[2-(1-methyl-pyrrolidin-2-yl)-ethyl]-guanidine, bishydrochloride salt: ¹H NMR (300 MHz, CD₃OD) δ 7.51 (d, J=7.2 Hz, 1H), 7.42 (s, 1H), 7.32 (s, 1H), 7.20 (dd, J=9.0, 2.4 Hz, 2H), 6.86 (d, J=8.7 Hz, 1H), 3.81 (s, 3H), 3.58 (s, 2H), 3.10 (br s, 5H), 2.89 (m, 6H), 2.71 (s, 1H), 2.37 (s, 2H), 2.10 (s, 3H), and 1.84 (s, 1H). LCMS: ES⁺ 519 (M+1), 521 (M+3).

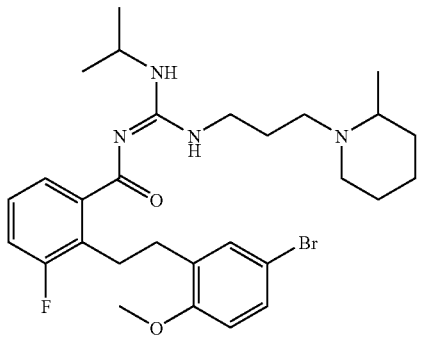

Compound 46: N-{2-[2-(5-Bromo-2-methoxy-phenyl)-ethyl]-3-fluoro-benzoyl}-N'-isopropyl-N''-[3-(2-methyl-piperidin-1-yl)-propyl]-guanidine N-{2-[2-(5-Bromo-2-methoxy-phenyl)-ethyl]-3-fluoro-benzoyl}-N'-(3-imidazol-1-yl-propyl)-N''-isopropyl-guanidine, monoformate salt: ¹H NMR (300 MHz, CD₃OD) δ 8.44 (s, 1H), 7.38 (d, J=7.8 Hz, 1H), 7.18-7.29 (m, 2H), 7.15 (d, J=2.7 Hz, 1H), 7.07 (t, J=8.7 Hz, 1H), 6.84 (d, J=8.7 Hz, 1H), 3.79 (s, 3H), 3.48 (m, 2H), 3.35 (d, J=9.0 Hz, 1H), 3.16 (t, J=7.8 Hz, 3H), 3.04 (br s, 2H), 2.82 (t, J=8.1 Hz, 3H), 1.97 (t, J=6.9 Hz, 2H), 1.74 (m, 4H), 1.43 (s, 2H), 1.29 (s, 6H), 1.21 (s, 3H), and 1.12 (m, 1H). LCMS: ES⁺ 575 (M+1), 577 (M+3).

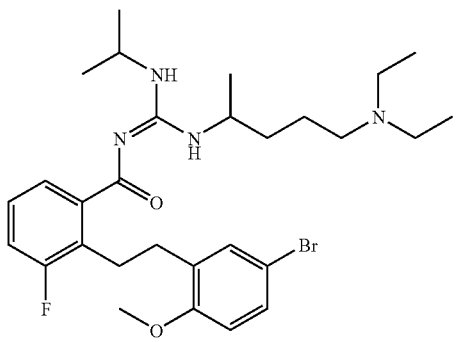

Compound 47: N-{2-[2-(5-Bromo-2-methoxy-phenyl)-ethyl]-3-fluoro-benzoyl}-N'-(4-diethylamino-1-methyl-butyl)-N''-isopropyl-guanidine, monoformate salt: ¹H NMR (300 MHz, CD₃OD) δ 8.51 (s, 1H), 7.36 (d, J=7.5 Hz, 1H), 7.13-7.28 (m, 3H), 7.02 (t, J=9.0 Hz, 1H), 6.82 (d, J=8.7 Hz, 1H), 3.78 (s, 3H), 3.10 (m, 8H), 2.80 (t, J=7.2 Hz), 1.64 (m, 4H), and 1.21 (m, 17H). LCMS: ES⁺ 577 (M+1), 579 (M+3).

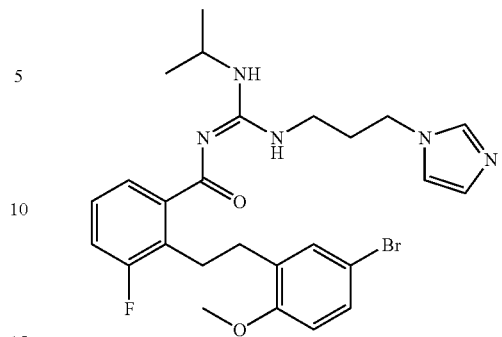

Compound 48: N-{2-[2-(5-Bromo-2-methoxy-phenyl)-ethyl]-3-fluoro-benzoyl}-N'-(3-imidazol-1-yl-propyl)-N''-isopropyl-guanidine, monoformate salt: ¹H NMR (300 MHz, CD₃OD) δ 8.18 (s, 1H), 8.05 (s, 1H), 6.98-7.32 (m, 7H), 6.77 (d, J=8.7 Hz, 1H), 4.11 (br s, 2H), 3.73 (s, 3H), 3.35 (br s, 2H), 3.13 (t, J=7.8 Hz, 3H), 2.76 (t, J=7.8 Hz, 2H), 2.07 (br s, 2H), and 1.23 (br s, 6H). LCMS: ES⁺ 544 (M+1), 546 (M+3).

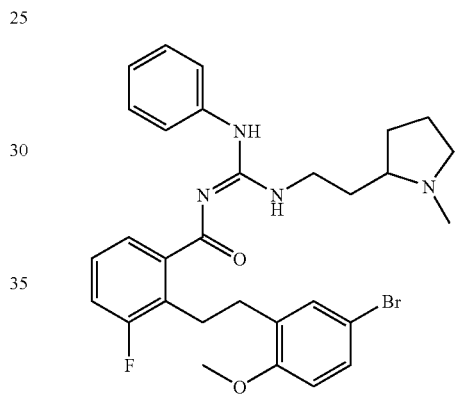

Compound 49: N-{2-[2-(5-Bromo-2-methoxy-phenyl)-ethyl]-3-fluoro-benzoyl}-N'-[2-(1-methyl-pyrrolidin-2-yl)-ethyl]-N''-phenyl-guanidine, monoformate salt: ¹H NMR (300 MHz, CD₃OD) δ 8.44 (s, 1H), 7.46 (m, 3H), 7.33-7.36 (m, 3H), 7.22-7.29 (m, 2H), 7.06-7.17 (m, 2H), 6.82 (d, J=8.7 Hz, 1H), 3.77 (s, 3H), 3.50 (t, J=6.3 Hz, 2H), 3.20 (s, 4H), 2.85-3.05 (m, 1H), 2.85 (t, J=6.3 Hz, 2H), 2.73 (br s, 3H), 2.29 (br s, 1H), 2.14 (br s, 1H), and 1.68-2.03 (m, 4H). LCMS: ES⁺ 581 (M+1), 583 (M+3).

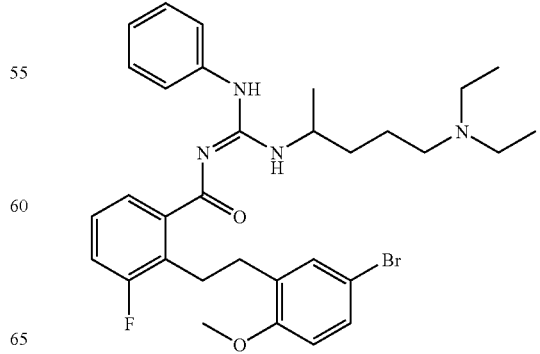

Compound 50: N-{2-[2-(5-Bromo-2-methoxy-phenyl)-ethyl]-3-fluoro-benzoyl}-N'-(4-diethylamino-1-methyl-butyl)-N"-phenyl-guanidine, bishydrochloride salt: $^1$H NMR (300 MHz, CD$_3$OD) δ 7.12-7.52 (m, 10H), 6.87 (d, J=8.7 Hz, 1H), 4.12 (s, 1H), 3.81 (s, 3H), 3.26 (m, 4H), 2.94 (m, 3H), 2.83 (m, 3H), 1.87 (s, 2H), 1.50 (m, 2H), and 1.33 (m, 9H). LCMS: ES$^+$ 611 (M+1), 613 (M+3)

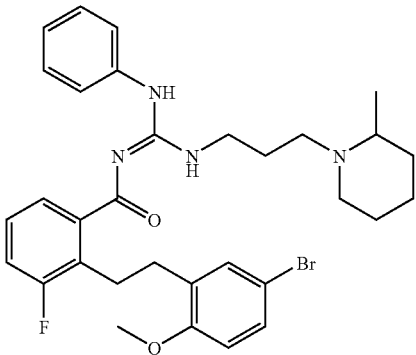

Compound 51: N-{2-[2-(5-Bromo-2-methoxy-phenyl)-ethyl]-3-fluoro-benzoyl}-N'-[3-(2-methyl-piperidin-1-yl)-propyl]-N"-phenyl-guanidine, bishydrochloride salt: $^1$H NMR (300 MHz, CD$_3$OD) δ 7.15-7.54 (m, 10H), 6.86 (d, J=8.7 Hz, 1H), 3.79 (s, 3H), 3.48-3.76 (m, 4H), 3.00 (s, 3H), 2.87 (m, 4H), 2.25 (br s, 2H), 2.00 (br s, 2H), 1.83 (br s 2H), 1.63 (br s, 2H), and 1.27-1.49 (m, 3H). LCMS: ES$^+$ 609 (M+1), 611 (M+3).

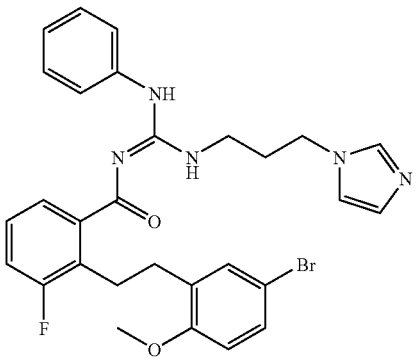

Compound 52: N-{2-[2-(5-Bromo-2-methoxy-phenyl)-ethyl]-3-fluoro-benzoyl}-N'-(3-imidazol-1-yl-propyl)-N"-phenyl-guanidine, bishydrochloride salt: $^1$H NMR (300 MHz, CD$_3$OD) δ 9.08 (s, 1H), 7.16-7.80 (m, 12H), 6.86 (d, J=8.7 Hz, 1H), 4.53 (br s, 2H), 3.78 (s, 3H), 3.67 (br s, 2H), 3.00 (m, 2H), 2.87 (m, 2H), and 2.4 (br s, 2H). LCMS: ES$^+$ 578 (M+1), 580 (M+3).

One embodiment of this invention relates to a composition comprising a compound of formula X or a tautomer or a pharmaceutically acceptable salt thereof, and a pharmaceutically acceptable carrier. It will be appreciated that the compounds of formula I in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of formula I, similar to metabolically labile esters or carbamates, which are capable of producing the parent compounds of formula I in vivo, are within the scope of this invention.

If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Also, the basic nitrogen-containing groups may be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a sterile liquid, such as, but not limited to, an oil, water, an alcohol, and combinations of these. Pharmaceutically suitable surfactants, suspending agents, or emulsifying agents, may be added for oral or parenteral administration. Suspensions may include oils, such as but not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Pharmaceutically acceptable carriers that may be used in these compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to a preferred embodiment, the compositions of this invention are formulated for pharmaceutical administration to a mammal, preferably a human being. Such pharmaceutical compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intrasynovial, intrasternal, intrathecal, intrahepatic, intralesional and intracranial injection or infusion techniques. Preferably, the compositions are administered orally or intravenously. The formulations of the invention may be designed for to be short-acting, fast-releasing, or long-acting. Still further, compounds can be administered in a local rather than systemic means, such as administration (e.g., injection) as a sustained release formulation.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such. as by bolus injection or continuous infusion. A unit dosage form for injection may be in ampoules or in multi-dose containers.

The pharmaceutical compositions of this invention may be orally administered in any orally acceptable dosage form including, but not limited to, capsules, tablets, aqueous suspensions or solutions. In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Any of the above dosage forms containing effective amounts are well within the bounds of routine experimentation and therefore, well within the scope of the instant invention. A therapeutically effective dose may vary depending upon the route of administration and dosage form. The preferred compound or compounds of the instant invention is a formulation that exhibits a high therapeutic index. The therapeutic index is the dose ratio between toxic and therapeutic effects which can be expressed as the ratio between LD50 and ED50. The LD50 is the dose lethal to 50% of the population and the ED50 is the dose therapeutically effective in 50% of the population. The LD50 and ED50 are determined by standard pharmaceutical procedures in animal cell cultures or experimental animals.

Besides those representative dosage forms described above, pharmaceutically acceptable excipients and carriers and dosage forms are generally known to those skilled in the art and are included in the instant invention.

The present invention provides methods of inhibiting or decreasing MC4-R activity as well as treating or ameliorating an MC4-R associated disorder in a human or non-human animal. "Treating" within the context of the instant invention, therefore, means an alleviation of symptoms associated with a disorder or disease, or halt of further progression or worsening of those symptoms, or prevention or prophylaxis of the disease or disorder. For example, within the context of wasting, successful treatment may include an alleviation of symptoms or halting the progression of the disease, as measured by increase in body weight, an increase in the amount of food or energy intake, or an increase in the amount of lean body mass.

The present methods comprise administering an effective amount of a compound or composition described herein to a mammal or non-human animal. As used herein, "effective amount" of a compound or composition of the present invention includes those amounts that antagonize or inhibit MC4-R. An amount which antagonizes or inhibits MC4-R is detectable, for example, by any assay capable of determining MC4-R activity, including those described below in the illustrative Testing Methods, or any other assay known by those skilled in the art that a detect signal transduction, in a biochemical pathway, through activation of G-protein coupled receptors, for example, by measuring an elevated cAMP level as compared to a control model.

The term "modulator" as used herein refers to a compound that interacts with the melanocortin receptor as either an agonist, inverse agonist, indirect agonist, or antagonist of the receptor. The terms "inverse agonize," "antagonize," or "inhibit" include the ability of a compound to diminish a detectable signal. Effective amounts may also include those amounts which alleviate symptoms of a MC4-R associated disorder treatable by inhibiting MC4-R (e.g., weight loss). Accordingly, "antagonist" includes compounds which interact with the MC4-R and modulate, e.g., inhibit or decrease, the ability of a second compound, e.g., α-melanocyte stimulating hormone or another MC4-R ligand, to interact with the MC4-R. The MC4-R binding compounds are preferably antagonists of MC4-R. The language "MC4-R binding compound" includes those compounds which interact with MC4-R resulting in modulation of the activity of MC4-R. MC4-R binding compounds may be identified using either in vitro (e.g., cell and non-cell based) or in vivo methods. Detailed descriptions of these methods are described below.

The amount of compound present in the methods and compositions described herein should be sufficient to cause a detectable decrease in the severity of the disorder or in MC4-R activity, as measured by any of the assays described in the examples. The amount of MC4-R modulator needed will depend on the effectiveness of the modulator for the given cell type and the length of time required to treat the disorder. In certain embodiments, the compositions of this invention may further comprise another therapeutic agent. When a second agent is used, the second agent may be administered either as a separate dosage form or as part of a single dosage form with the compounds or compositions of this invention.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular compound and other therapeutic agent, if present, in the composition.

The term "mammal" includes organisms which express the MC4-R. Examples of mammals include mice, rats, cows, sheep, pigs, goats, horses, bears, monkeys, dogs, cats and, preferably, humans. Transgenic organisms which express the MC4-R are also included in this definition.

An MC4-R associated disorder, or MC4-R-mediated disease, which may be treated by the methods provided, includes those states, disorders, or diseases characterized by aberrant or undesirable activity or expression of MC4-Rs. It also includes those states, disorders and diseases associated with MC4-R ligands (e.g., α-melanocyte stimulating hormone). The language also includes prevention of states, disorders and diseases characterized by aberrant or undesirable activity of MC4-Rs or its ligands. MC4-R associated disorders include weight loss and wasting disorders, bone loss disorders, neuronal injuries or disorders, cardiovascular disorders and thermoregulation.

Examples of MC4-R associated disorders include feeding and wasting disorders, such as cachexia (e.g., chronic disease associated cachexia including cancer cachexia, AIDS cachexia, CHF cachexia, etc.), anorexia, catabolic wasting, and aging associated involuntary weight loss. Recent studies have demonstrated that the central melanocortin signaling system, in particular MC4-R contributes to animal models of cachexia. Wisse B E, et al. *Endocrinology* 142:3292-3301 (2001); Marks D L, et al. *Cancer Res* 61:1432-1438 (2001); Vergoni A V, et al. *Eu J Pharm* 369:11-15 (1999). Cachexia is a common pathological syndrome associated with cancer and other chronic illnesses (e.g., AIDS, chronic heart failure, chronic infection, etc), which encompasses both the loss of appetite and the inability to conserve energy. A hallmark of the disorder is loss of fat and lean body mass, contributing to morbidity, mortality, and reduced quality of life in afflicted patients. Ronald M. L. and J. B. Tatro, Diabetes, 8: 267-271, (1999); Tisdale M J *Nutrition* 17: 438-442 (2001). Physiologically, this may be a result from any one of a number of complex factors, such as loss of appetite and possibly abnormal catabolism. Accordingly the instant invention provides compounds, compositions, and methods effective for increasing feeding behavior and body weight, which are particularly useful in treating those disorders or diseases associated with weight loss and wasting (e.g., cachexia (e.g., chronic disease associated cachexia including cancer cachexia, AIDS cachexia, CHF cachexia, etc.), anorexia, and aging associated involuntary weight loss).

In another embodiment, the MC4-R associated disorder is a bone associated disorder. MC4-R knockout mice have been shown to have enhanced bone thickness (Ducy et al. Science, (September, 2000) 289:1501-1504). Examples of bone associated disorders which may be treated with MC4-R binding compounds of the invention include disorders and states where the formation, repair or remodeling of bone is advantageous. For examples bone associated states include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone associated disorders include all states in which the formation, repair or remodeling of bone is advantageous to the subject as well as all other disorders associated with the bones or skeletal system of a subject which can be treated with the compounds of the invention.

Melanocortins increase neuropathic pain in animal models and antagonize opiate analgesia, and antagonists counteract neuropathic pain. Vrinten D H, et al. *J Neurosci* 20:8131-8137 (2000); Adan R A H in *The melanocortin receptors*. Cone R D, ed. Totowa, N.J.: Humana Press; 109-141 (2000). Additionally, patients with cancer might have the additional benefit of improved pain control when treated with melanocortin receptor antagonists undergoing a cancer cachexia treatment regimen. Thus, the methods and compositions described herein may be useful in the treatment of MC4-R associated pain or neuronal disorders, including neuropathic pain.

Assays

The Scintillation Proximity Assay (SPA) is a non-cell based in vitro assay. It can be used to identify compounds that interact with MC4-R. Such compounds may act as antagonists or agonists of MC4-R activity and may be used in the treatment of body weight disorders. One example of a qualitative measure of binding affinity of a MC4-R binding compound to MC4-R is its $IC_{50}$. Preferably, the MC4-R binding compound binds to the MC4-R with a binding affinity, for example, of about 50 µM or less, 20 µM or less, 10 µM or less, 5 µM or less, 2.5 µM or less, or 1 µM or less. In an advantageous embodiment, the $IC_{50}$ of a MC4-R binding compounds is about 0.5 µM or less, about 0.3 µM or less, about 0.1 µM or less, about 0.08 µM or less, about 0.06 µM or less, about 0.05 µM or less, about 0.04 µM or less, or, preferably, about 0.03 µM or less.

In the SPA, isolated membranes are used to identify compounds that interact with MC4-R. For example, in a typical experiment using isolated membranes, 293 cells may be genetically engineered to express the MC4-R. Membranes are be harvested by standard techniques and used in an in vitro binding assay. $^{125}$I-labeled ligand (e.g., $^{125}$I-labeled α-MSH, β-MSH, or ACTH) is bound to the membranes and assayed for specific activity; specific binding is determined by comparison with binding assays performed in the presence of excess unlabelled ligand.

To identify MC4-R binding compounds, membranes are incubated with labeled ligand in the presence or absence of test compound. Compounds that bind to the receptor and compete with labeled ligand for binding to the membranes reduced the signal compared to the vehicle control samples. Preferably, the screens are designed to identify compounds that antagonize the interaction between MC4-R and MC4-R ligands such as α-MSH, β-MSH and ACTH. In such screens, the MC4-R ligands are labeled and test compounds can be assayed for their ability to antagonize the binding of labeled ligand to MC4-R.

Cell based assay systems can also be used to identify MC4-R binding compounds. An example of a cell based assay system is the cAMP assay, which is described in more detail below. Cell based methods may use cells that endogenously express MC4-R for screening compounds which bind to MC4-R. Alternatively, cell lines, such as 293 cells, COS cells, CHO cells, fibroblasts, and the like, genetically engineered to express the MC4-R can also be used for screening purposes. Preferably, host cells genetically engineered to express a functional receptor that responds to activation by melanocortin peptides can be used as an endpoint in the assay; e.g., as measured by a chemical, physiological, biological, or phenotypic change, induction of a host cell gene or a reporter gene, change in cAMP levels, adenylyl cyclase activity, host cell G protein activity, extracellular acidification rate, host cell kinase activity, proliferation, differentiation, etc.

To be useful in screening assays, the host cells expressing functional MC4-R should give a significant response to MC4-R ligand, preferably greater than 5-fold induction over background. Host cells should preferably possess a number of characteristics, depending on the readout, to maximize the inductive response by melanocortin peptides, for example, for detecting a strong induction of a CRE reporter gene: (a) a low natural level of cAMP, (b) G proteins capable of interacting with the MC4-R, (c) a high level of adenylyl cyclase, (d) a high level of protein kinase A, (e) a low level of phosphodiesterases, and (f) a high level of cAMP response element binding protein would be advantageous. To increase response to melanocortin peptide, host cells could be engineered to express a greater amount of favorable factors or a lesser amount of unfavorable factors. In addition, alternative pathways for induction of the CRE reporter could be eliminated to reduce basal levels.

In using such cell systems, the cells expressing the melanocortin receptor are exposed to a test compound or to vehicle controls (e.g., placebos). After exposure, the cells can be assayed to measure the expression and/or activity of components of the signal transduction pathway of the melanocortin receptor, or the activity of the signal transduction pathway itself can be assayed. For example, after exposure, cell lysates can be assayed for induction of cAMP. The ability of a test compound to increase levels of cAMP, above those levels seen with cells treated with a vehicle control, indicates that the test compound induces signal transduction mediated by the melanocortin receptor expressed by the host cell. In screening for compounds that may act as antagonists of MC4-R, it is necessary to include ligands that activate the MC4-R, e.g., α-MSH, β-MSH or ACTH, to test for inhibition of signal transduction by the test compound as compared to vehicle controls.

When it is desired to discriminate between the melanocortin receptors and to identify compounds that selectively agonize or antagonize the MC4-R, the assays described above may be conducted using a panel of host cells, each genetically engineered to express one of the melanocortin receptors (MC1-R through MC5-R). Expression of the human melanocortin receptors is preferred for drug discovery purposes. To this end, host cells can be genetically engineered to express any of the amino acid sequences shown for melanocortin receptors 1 through 5. The cloning and characterization of each receptor has been described: MC1-R and MC2-R (Mountjoy., 1992, Science 257: 1248-1251; Chhajlani & Wikberg, 1992 FEBS Lett. 309: 417-420); MC3-R (Roselli-Rehfuss et al., 1993, Proc. Natl. Acad. Sci., USA 90: 8856-8860; Gantz et al., 1993, J. Biol. Chem. 268: 8246-8250); MC4-R (Gantz et al., 1993, J. Biol. Chem. 268: 15174-15179; Mountjoy et al., 1994, Mol. Endo. 8: 1298-1308); and MC5-R (Chhajlani et al., 1993, Biochem. Biophys. Res. Commun. 195: 866-873; Gantz et al., 1994, Biochem. Biophys. Res. Commun. 200; 1234-1220), each of which is incorporated by reference herein in its entirety. Thus, each of the foregoing sequences can be utilized to engineer a cell or cell line that expresses one of the melanocortin receptors for use in screening assays described herein. To identify compounds that specifically or selectively regulate MC4-R activity, the activation, or inhibition of MC4-R activation is compared to the effect of the test compound on the other melanocortin receptors. In certain embodiments, it may be advantageous to select compounds of the invention selective for MC4-R, or, alternatively, it may be useful to select compounds which interact with other receptors as well.

In one further embodiment, the MC4-R binding compounds of the invention are more selective for the MC4-R than at least one other MC receptors, for example, more than twice as selective, at least ten times as selective, at least twenty times as selective, at least fifty times as selective, or at least one hundred times as selective.

In one further embodiment, the MC4-R binding compounds of the invention are more selective for the MC4-R than the MC1-R, for example, more than twice as selective, at least ten times as selective, at least twenty times as selective, at least fifty times as selective, or at least one hundred times as selective.

In one further embodiment, the MC4-R binding compounds of the invention are more selective for the MC4-R than the MC3-R, for example, more than twice as selective, at least ten times as selective, at least twenty times as selective, at least fifty times as selective, or at least one hundred times as selective.

In one further embodiment, the MC4-R binding compounds of the invention are more selective for the MC4-R than the MC5-R, for example, more than twice as selective, at least ten times as selective, at least twenty times as selective, at least fifty times as selective, or at least one hundred times as selective.

In yet another further embodiment, the MC4-R binding compounds of the invention are more selective for the MC4-R receptor than at least one, two or three other MC receptors (such as, for example, MC1-R[1], MC3-R[1], or MC5-R). In a further embodiment, the MC4-R binding compounds are more selective for the MC4-R than MC1-R, MC3-R, and MC5-R. In a further embodiment, the MC4-R binding compounds as at least ten times as selective, at least twenty times as selective, at least fifty times as selective, or at least one hundred times as selective for the MC4-R than the MC1-R, MC3-R and the MC5-R.

The compositions delineated herein can include additional therapeutic agents, including for example, HIV antiviral agents (e.g., reverse transcriptase inhibitors, protease inhibitors, proteosome inhibitors)cardiovascular therapeutic agents, or anticancer agents (e.g., platinum agents, list).

MC4-R binding compounds may be identified using either in vitro methods, such as cell based or non-cell based methods, or in vivo methods. These methods are known in the art and are described below.

Testing Methods

EXAMPLE

Scintillation Proximity Assay (SPA)

High-Throughput Receptor Binding Screening for MC4-R Binding Compounds

A. Preparation of Membranes from MC4-R Cells

A crude preparation of plasma membranes, of sufficient purity for use in the scintillation proximity assay (SPA), was prepared using the following protocol (Maeda et al. (1983) *Biochem. Biophys. Acta* 731:115-120).

MC4-R cells were stable recombinant K293 cells overexpressing the MC4-R. The cells were routinely cultured and passaged in a growth medium composed of DMEM base medium: 10% fetal bovine serum (FBS), 1× Glutamine, and 0.5 mg/ml G418. Terminal cultures (i.e., those which will be processed to produce plasma membranes) were grown in identical media, with the exception that the media contained 0.2 mg/ml G418.

At 4° C., harvested cells were pelleted and immediately washed with 25 mL of PBS. The washed cells were resuspended in two volumes of STM buffer (0.25 M sucrose, 5 mM Tris, 1 mM $MgCl_2$, pH 7.5), containing Boehringer Complete™ protease inhibitors. Cell breakage was accomplished using a Dounce homogenizer. After 20-30 strokes, nuclei and unbroken cells were pelleted by centrifugation at 1100 rpm for 5 minutes. The supernatant was saved and the pellet was resuspended in 1 volume of STM/protease inhibitors, and then a further lysis step was carried out by the Dounce homogenizer (10-20 strokes). This material was then combined with the first supernatant. 11.25 mL of the homogenate was gently layered on top of 27.25 mL f 42% (w/w) sucrose (5 mM Tris, 1 mM $MgCl_2$, pH 7.5). After spinning at 28,000 rpm (ultracentrifuge, SW-28 rotor) for 90 minutes, membranes were collected at the interface with a transfer pipette.

The membrane suspension obtained from the sucrose interface was collected and diluted with 5 mM Tris and 1 mM $MgCl_2$. Membranes were collected by a further round of centrifugation at 33,000 rpm for 30 minutes (SW-41 Ti rotor). The pellet of membranes was subsequently re-suspended in a small (0.5 mL) volume of STM, using a 2 mL Dounce homogenizer, and immediately frozen. The resulting membranes were stable to both freeze-thaw cycles and temperatures around 4° C. for at least 6 hours.

B. High-Throughput Screen

A scintillation proximity assay (SPA) format ligand binding assay was used. The membranes from the MC4-R mammalian cells (K293 expressing MC4-R) were bound to wheat germ agglutinin (WGA) coated SPA beads. The membrane coated SPA beads were added to screening plates, which contained the test compounds pre-dissolved in 30 μL of 10% DMSO. After pre-equilibration of the receptor coated beads with the test compounds (1 hour), 2 nM of radioactive ligand ([$^{125}$I]NDP-α-MSH) was added. Since the binding of the radioactive ligand to the receptor causes the scintillation of the beads, blockage of the binding of the radioactive ligand by a small molecule causes a reduction in scintillation.

1. Pre-Binding of the MC4-R Membranes to the WGA-SPA Beads

The membranes were mixed with the SPA beads to make a 2× stock of membrane and beads.

For a twenty plate batch of screening plates, the components were mixed in proportions given in Table 4. The membranes and beads were stirred with a magnetic stir bar at room temperature for 1-2 hours to allow binding.

TABLE 4

SPA Reagents

| Component | Volume | Final Concentration in Assay |
| --- | --- | --- |
| 4 mg/ml WGA-SPA Beads | 14.4 mL | 25 μg/well |
| MC4-R crude plasma membranes* | 600 μL* | 5 μg/well |
| SPA Binding Buffer | 100 mL | N/A |

*the exact amount of membranes used varies with the quality of the membrane preparation and must be checked for each new batch.

2. Binding Assay

The following assay was performed with automation using a Titertec Multiprop with plate stacker.

30 μL of 10% DMSO was added per well to the dried compound film in an OptiPlate. Then, 5 μL of cold NDP-α-MSH was added to the control wells. Subsequently, 50 μl per well of 2× membranes and beads were added and pre-equilibrated with the compounds for 1 hour.

Binding was initiated by adding 20 μL of radioactive ligand (a 20 nM solution of [$^{125}$I]-NDP-α-MSH) to each test well. The plates were incubated overnight at room temperature and read the following morning.

The reagents and amounts are summarized below in Table 5.

TABLE 5

Binding Assay Reagents

| Reagent | Volume (μL) | | | |
|---|---|---|---|---|
| | Max (100%) | Min (0%) | 50% | Test |
| 20% DMSO | 30 | 30 | 30 | 30 |
| 2× membranes + beads | 60 | 0 | 60 | 60 |
| 2 nM [$^{125}$I]-NDP-α-MSH in binding buffer | 20 | 20 | 20 | 20 |
| NDP-α-MSH (5 μM in H$_2$O) | 5 | 0 | 0 | 0 |
| NDP-α-MSH (20 nM in H$_2$O) | 0 | 0 | 5 | 0 |
| Test Compound* | 0 | 0 | 0 | 5 μm |

*Test compound stock diluted in BuOH 1:10, 25 μL dried in assay plate in hood prior to addition of assay buffer. Well contained 0.5 nmol of each test compound (20/well) in 2.5 μL 100% DMSO.

The potency of the compounds was quantified with respect to positive (100% inhibition) and negative (no inhibitor; 0% inhibition) controls, using the following formula:

% Inhibition={1−[cpm−(positive control)]/[(negative control)−(positive control)]}*100%

EXAMPLE

Membrane Binding Filtration Assay

To 96 well plates the following is added,
Wells 1-10 (A-H) [10×] serially diluted compound=10 μl
Wells 11-12 (A-D) 10% DMSO/Assay Buffer=10 μl
Wells 11-12 (E-H) 5.5 μM [N,D,P]-α-MSH (Sigma)/10% DMSO=10 μl
Assay Buffer comprising 25 mM HEPES (pH 7.0), 1.5 mM CaCl$_2$, 1 mM MgSO$_4$, 0.1 M NaCl, 0.2% BSA, 1 mM 1.10 Phenanthroline, and protease inhibitors (Complete Mini EDTA-free, Roche Diagnostics) is used.

To all wells, 40 μl of 1:40 diluted human MC4 membranes (Perkin Elmer) and 50 μl of 0.5 nM $^{125}$I-[N,D,P]-α-MSH (Amersham) are added, then incubated at room temperature for 2 h. The supernatant is filtered through Unifilter GF/B (Perkin Elmer) plates (pre-equilibrated with 0.3% PEI) using ice cold Wash Buffer (25 mM HEPES (pH 7.0), 1.5 mM CaCl$_2$, 1 mM MgSO$_4$, and 0.1 M NaCl). The Unifilter plates are dried, scintillation fluid added, and the amount of radio-activity measured using a 1450 MicroBeta Trilux (Perkin Elmer) scintillation counter. The affinity of the compound is quantified as follows:

% Inhibition={1−[unknown−non-specific binding]/[Total−non-specific binding]}×100

IC50 is defined as the X value which is equal to the Y value at 50% Inhibition. The following 4 parameter logistic model allowed curve fitting using nonlinear regression and IC50 determination:

$Y = A + [((B-A)/(1+[(C/X)^D])]$;

where:
A=Minimum Y; B=Maximum Y; C=Log IC50; D=Slope Factor;
X value=Known X range of compound concentration;
and Y value=Known Y values for the X range (Y is the response from 0 to 100% Inhibition; Y starts at Min and goes to Max with a sigmoidal shape).

Ki is calculated according to the Cheng-Prusoff equation, $$Ki = \frac{IC50}{1 + \frac{\text{Ligand concentration}}{Kd}}$$

EXAMPLE cAMP Assay for MC4-R Antagonist Activity

MC4 receptors are expressed in stably transfected K293 cells. MC4/HEK293 cells are plated (60,000 cells per well) in poly-D-lysine coated 96 well plates (Becton Dickinson) and grown overnight in DMEM base medium (10% FBS, 1× glutamine, and 0.4 mg/ml G418) (Gibco BRL) at 37° C./5.0% CO$_2$. The next day, the supernatant is discarded and the cells are incubated in 50 uL of Opti-MEM (Gibco BRL)/0.5 mM IBMX (isobutylmethylxanthine (Sigma)) for 15 min at 37° C./5% CO$_2$.

50 uL of [3×] serially diluted compound is added to cells and incubated for 10 min at 37° C./5% CO$_2$, followed by addition of 50 uL of [3×] [N,D,P]-o(MSH (final concentration 1 nM) and incubated for 35 min at 37° C./5% CO$_2$. The amount of cAMP produced be cells is detected using the cAMP-Screen Immunoassay (Applied Biosystems, catalog number T1502) and 1450 MicroBeta Trilux (Perkin Elmer), according to manufacturer's instructions. IC50 of the compound is calculated using the equation described above.

EXAMPLE

In Vivo Assay for Melanocortin Receptor Antagonist Activity

In vivo assays are used to test effects of melanocortin antagonists in mice. For example, compounds can be tested by monitoring acute reversal of agonist-induced decrease in feeding.

Male lean C57BL/6J mice are individually housed in macrolon cages (22±2 C°; 12:12 h light/dark cycle with lights off at 6 pm). Tap water and mouse chow diet are given ad libitum. Mice are stereotaxically implanted with a chronic guide cannula aimed to the third ventricle (intracerabroventricular) one week prior to testing.

On the evening prior to administration of compound, mice are subjected to overnight fasting. The following morning mice are divided into three test groups. The first group is injected intracerabroventricularly (icv) with test compound, followed 1 hour later by administration of agonist via icv injection. The second group receives only the icv injection of agonist, and the third control group does not receive an icv injection. Following administration, mice are replaced in their home cages and food intake is measured at 1, 2, 4 and 6 hours after administration of the first injection of antagonist.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of example.

What is claimed is:

1. A compound of formula I:

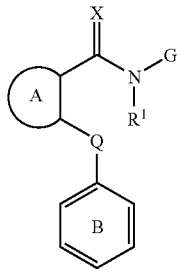

or a pharmaceutically acceptable salt thereof, wherein:
X is oxygen or sulfur;
G is a group $G^1$:

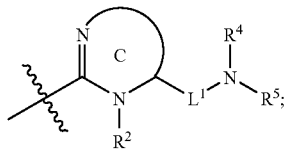

Ring C of $G^1$ an optionally substituted 5-6 membered aromatic or non-aromatic ring having two or three ring nitrogens is selected from the group consisting of:

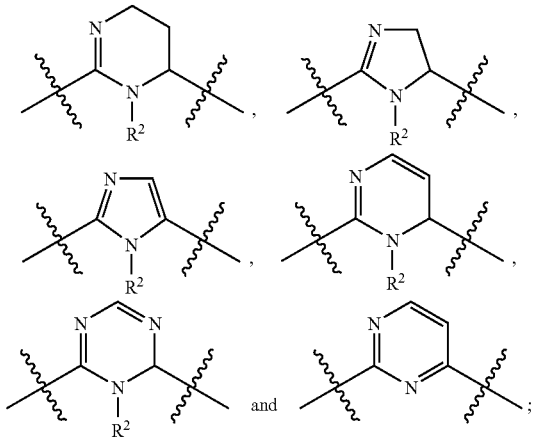

$L^1$ is a $C_{1-6}$ alkylidene chain optionally substituted by 1-3 $R^6$ groups;
$R^1$ is hydrogen or a $C_{1-6}$ aliphatic group;
$R^2$ is selected from hydrogen, $C_{1-8}$ aliphatic, $C_{6-10}$ aryl and $C_{7-10}$ aralkyl groups, or, when Ring C is a 6-membered aromatic ring, $R^2$ is a lone electron pair;
$R^4$ is hydrogen or a $C_{1-8}$ aliphatic, C(O)($C_{1-8}$ aliphatic), $CO_2(C_{1-8}$ aliphatic), C(=O)N(R10)($C_{1-7}$ aliphatic), $C_{6-10}$ aryl, heteroaryl, $C_{7-12}$ aralkyl or heteroaralkyl group, and $R^5$ is hydrogen or a $C_{1-8}$ aliphatic group; or $R^4$ and $R^5$ taken together with their intervening nitrogen form a substituted or unsubstituted, aromatic or non-aromatic, 4-14 membered monocyclic, bicyclic or tricyclic ring system having, in addition to said intervening nitrogen, 0-4 ring heteroatoms selected from nitrogen, sulfur and oxygen;

Ring A is a 5-membered heteroaryl ring or a 6-membered aromatic ring having 0-2 ring nitrogen atoms, wherein Q and C(=X)N($R^1$)-G are attached at ortho positions on Ring A and wherein Ring A is optionally substituted by one to three $R^7$ groups;

Ring B is a 6-membered aromatic ring having 0-2 ring nitrogen atoms, wherein Ring B is optionally substituted by one or more $R^8$ groups;

Q is a $C_{2-4}$ alkylidene chain optionally substituted by one to three $R^9$ groups;

each $R^6$ is independently selected from halo, —$OR^1$, —CN, —$C_{1-6}$ aliphatic, —N($R^{10}$)$_2$, —C(O)($C_{1-8}$ aliphatic), —$CO_2R^1$, —$CH_2CO_2R^1$ and —C(=O)N($R^{10}$)($C_{1-5}$ aliphatic) groups;

each $R^7$, unless forming a ring with an $R^9$ group, is independently selected from halo, —$NO_2$ and —CN, or is a substituted or unsubstituted group selected from —$R^{12}$, —$OR^1$, $SR^{12}$, —$C_{6-10}$ aryl, -heterocyclyl, -heteroaryl, —($C_{6-10}$ aryl)alkyl, -(heterocyclyl)alkyl, -(heteroaryl)alkyl, —N($R^{10}$)$_2$, —$NR^{10}C(O)R^1$, —$NR^{10}C(O)N(R^{10})_2$, —$NR^{10}CO_2R^{12}$, —$CO_2R^1$, —$C(O)R^1$, C(O)N($R^{10}$)$_2$, —OC(O)N($R^{10}$)$_2$, —S(O)$_2R^{12}$, —$SO_2N(R^{10})_2$, —$S(O)R^{12}$, —$NR^{10}SO_2N(R^{10})_2$, —$NR^{10}SO_2R^{12}$, and —C(=NH)—N($R^{10}$)$_2$ groups, or two adjacent $R^7$ groups taken together with their intervening atoms form a 5-6 membered unsaturated or partially unsaturated ring having 0-2 ring heteroatoms selected from nitrogen, oxygen and sulfur;

each $R^8$ is independently selected from halo, —$NO_2$ and —CN, or is a substituted or unsubstituted group selected from —$R^{12}$, —$OR^1$, —$SR^{12}$, —$C_{6-10}$ aryl, -heterocyclyl, -heteroaryl, —($C_{6-10}$ aryl)alkyl, -(heterocyclyl)alkyl, -(heteroaryl)alkyl, —N($R^{10}$)$_2$, —$NR^{10}C(O)R^1$, —$NR^{10}C(O)N(R^{10})_2$, —$NR^{10}CO_2R^{12}$, —$CO_2R^1$, —$C(O)R^1$, —$C(O)N(R^{10})_2$, —OC(O)N($R^{10}$)$_2$, —S(O)$_2R^{12}$, —$SO_2N(R^{10})_2$, —$S(O)R^{12}$, —$NR^{10}SO_2N(R^{10})_2$, —$NR^{10}SO_2R^{12}$, and —C(=NH)—N($R^{10}$)$_2$ groups, or two adjacent $R^8$ groups taken together with their intervening atoms form a 5-6 membered unsaturated or partially unsaturated ring having 0-2 ring heteroatoms selected from nitrogen, oxygen and sulfur;

each $R^9$ is independently selected from halo, $OR^1$, CN, $C_{1-6}$ aliphatic, N($R^{10}$)$_2$, C(O)($C_{1-5}$ aliphatic), $CO_2(C_{1-5}$ aliphatic and —C(=O)N($R^{10}$)($C_{1-5}$ aliphatic) groups, or $R^9$ and an $R^7$ group, at a position ortho to Q, taken together with their intervening atoms form a 5-7 membered unsaturated or partially saturated ring having 0-2 ring heteroatoms selected from N, O and S;

each $R^{10}$ is independently selected from hydrogen, optionally substituted $C_{1-8}$ aliphatic groups, C(=O)$R^1$, $CO_2R^1$ and $SO_2R^1$ groups, or two $R^{10}$ groups on the same nitrogen taken together with the nitrogen form a 5-8 membered aromatic or non-aromatic ring having, in addition to the nitrogen, 0-2 ring heteroatoms selected from N, O and S;

each $R^{11}$ is independently selected from hydrogen, $CO_2R^{12}$, CON($R^{12}$)$_2$, $OR^{12}$ and optionally substituted $C_{1-8}$ aliphatic groups; and each $R^{12}$ is independently selected from optionally substituted $C_{1-8}$ aliphatic groups.

2. The compound or salt of claim 1 having one or more of features (a)-(g):
(a) X is oxygen;
(b) $L^1$ is a $C_{2-3}$ alkylidene chain;
(c) Q is —CH$_2$CH$_2$—;
(d) $G^1$ is

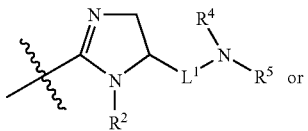

G$^{1-a}$ or

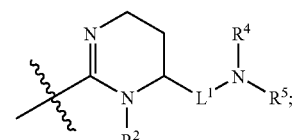

G$^{1-b}$

;

(e) $R^4$ and $R^5$ are each independently selected from a $C_{1-4}$ aliphatic group, or $R^4$ and $R^5$ taken together with their intervening nitrogen form a 5-6 membered ring;
(f) Ring A is an optionally substituted phenyl or thienyl group;
(g) Ring B is a substituted phenyl or naphthyl group.

3. The compound or salt of claim 2 wherein:
(a) X is oxygen;
(b) $L^1$ is a $C_{2-3}$ alkylidene chain;
(c) Q is —CH$_2$CH$_2$—;
(d) $G^1$ is

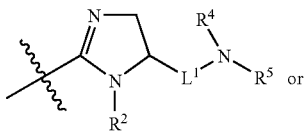

G$^{1-a}$ or

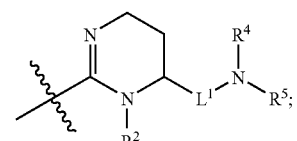

G$^{1-b}$

;

(e) $R^4$ and $R^5$ are each independently selected from a $C_{1-4}$ aliphatic group, or $R^4$ and $R^5$ taken together with their intervening nitrogen form a 5-6 membered ring;
(f) Ring A is an optionally substituted phenyl or thienyl group; and
(g) Ring B is a substituted phenyl or naphthyl group.

4. The compound or salt of claim 1 having one or more of features (a)-(g):
(a) X is oxygen;
(b) $L^1$ is —CH$_2$CH$_2$—or —CH$_2$CH$_2$CH$_2$—;
(c) Q is —CH$_2$CH$_2$—;
(d) $G^1$ is

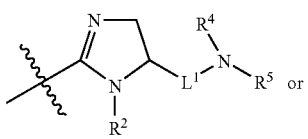

G$^{1-a}$ or

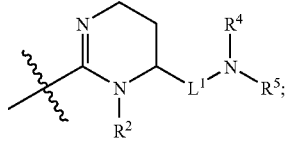

G$^{1-b}$

;

(e) $R^4$ and $R^5$ are each independently selected from a $C_{1-3}$ aliphatic group, or $R^4$ and $R^5$ taken together with their intervening nitrogen form a piperidinyl, pyrrolidinyl, piperazinyl or morpholinyl ring;
(f) Ring A is an optionally substituted phenyl or thienyl group;
(g) Ring B is a substituted phenyl or naphthyl group.

5. The compound or salt of claim 1 wherein:
(a) X is oxygen;
(b) $L^1$ is —CH$_2$CH$_2$—or —CH$_2$CH$_2$CH$_2$—;
(c) Q is —CH$_2$CH$_2$—;
(d) $G^1$ is

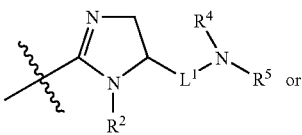

G$^{1-a}$ or

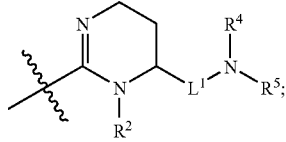

G$^{1-b}$

;

(e) $R^4$ and $R^5$ are each independently selected from a $C_{1-3}$ aliphatic group, or $R^4$ and $R^5$ taken together with their intervening nitrogen form a piperidinyl, pyrrolidinyl, piperazinyl or morpholinyl ring;
(f) Ring A is an optionally substituted phenyl or thienyl group; and
(g) Ring B is a substituted phenyl or naphthyl group.

6. The compound or salt thereof of claim 1, wherein the compound is of formula II-A or II-B:

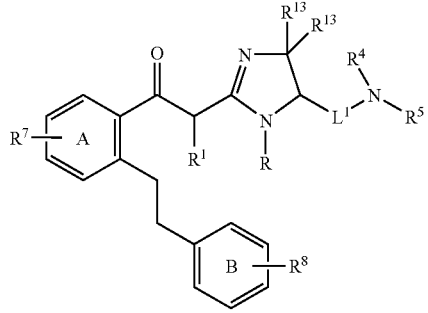

II-A

-continued

II-B

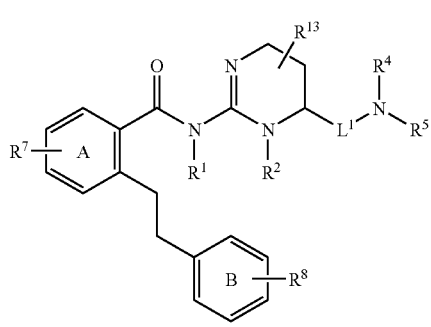

wherein:
R$^1$ and R$^2$ are each hydrogen;
R$^3$ is hydrogen;
L$^1$ is —CH$_2$CH$_2$— or —CH$_2$CH$_2$CH$_2$—;
R$^7$ is absent or is -halo, —NO$_2$, —CN, or a substituted or unsubstituted group selected from —R$^{12}$, —OR$^1$, —SR$^{12}$, —C$_{6-10}$ aryl, -heterocyclyl, -heteroaryl, —(C$_{6-10}$ aryl)alkyl, -(heterocyclyl)alkyl, -(heteroaryl)alkyl,)—N(R$^{10}$)$_2$, —NR$^{10}$C(O)R$^1$, —NR$^{10}$C(O)N(R$^{10}$)$_2$, —NR$^{10}$CO$_2$R$^{12}$, —CO$_2$R$^1$, —C(O)R$^1$, —C(O)N(R$^{10}$)$_2$, —OC(O)N(R$^{10}$)$_2$, —S(O)$_2$R$^{12}$, —SO$_2$N(R$^{10}$)$_2$, —S(O)R$^{12}$, —NR$^{10}$SO$_2$N(R$^{10}$)$_2$, —NR$^{10}$SO$_2$R$^{12}$, and —C(=NH)—N(R$^{10}$)$_2$ groups, or two adjacent R$^7$ groups taken together with their intervening atoms form a 5-6 membered unsaturated or partially unsaturated ring having 0-2 heteroatoms selected from nitrogen, oxygen and sulfur;
R$^8$ is -halo, —NO$_2$, —CN, or a substituted or unsubstituted group selected from —R$^{12}$, —OR$^1$, —SR$^{12}$, —C$_{6-10}$ aryl, -heterocyclyl, -heteroaryl, —C$_{6-10}$ aryl)alkyl, -(heterocyclyl)alkyl, -heteroaryl)alkyl, —N(R$^{10}$)$_2$, —NR$^{10}$C(O)R$^1$, —NR$^{10}$C(O)N(R$^{10}$)$_2$, —NR$^{10}$CO$_2$R$^{12}$, —CO$_2$R$^1$, —C(O)R$^1$, —C(O)N(R$^{10}$)$_2$, —OC(O)N(R$^{10}$)$_2$, —S(O)$_2$R$^{12}$, —SO$_2$N(R$^{10}$)$_2$, —S(O)R$^{12}$, —NR$^{10}$SO$_2$N(R$^{10}$)$_2$, —NR$^{10}$SO$_2$R$^{12}$, and —C(=NH)—N(R$^{10}$)$_2$, groups, or two adjacent R$^8$ groups taken together with their intervening atoms form a 5-6 membered unsaturated or partially unsaturated ring having 0-2 heteroatoms selected from nitrogen, oxygen and sulfur;
(i) R$^4$ and R$^5$ are each independently selected from a C$_{1-4}$ aliphatic group, or (ii) R$^4$ and R$^5$ taken together with their intervening nitrogen form a 5-6 membered ring, or (iii) R$^5$ is a C$_{1-4}$ aliphatic group and R$^4$ is aryl, aralkyl, heteroaryl or heteroaralkyl;
each R$^{13}$ is independently selected from hydrogen, C$_{1-6}$ aliphatic, C(O)R$^1$, CO$_2$R$^1$, CN,)—N(R$^{10}$)$_2$, C(O)N(R$^{10}$)$_2$ and —OR$^1$ groups, or two R$^{13}$ groups on the same carbon taken together form =O, or two R$^{13}$ groups taken together with their intervening atoms form a 3-7 membered ring having 0-2 ring heteroatoms;
each R$^{10}$ is independently selected from hydrogen, optionally substituted C$_{1-8}$ aliphatic groups, C(O)R$^1$, CO$_2$R$^1$ and SO$_2$R$^1$ groups, or two R$^{10}$ groups on the same nitrogen taken together with the nitrogen form a 5-8 membered aromatic or non-aromatic ring having, in addition to the nitrogen, 0-2 ring heteroatoms selected from N, O and S;
each R$^{11}$ is independently selected from hydrogen and optionally substituted C$_{1-8}$ aliphatic groups; and each R$^{12}$ is independently selected from optionally substituted C$_{1-8}$ aliphatic groups.

7. The compound or salt of claim 6 wherein:
R$^1$ and R$^2$ are each hydrogen;
R$^3$ is hydrogen;
L$^1$ is —CH$_2$CH$_2$— or —CH$_2$CH$_2$CH$_2$—;
R$^7$ is absent or is -halo, —CN, —R$^{12}$, —OR$^1$, —SR$^{12}$, —N(R$^{10}$)$_2$, —NR$^{10}$C(O)R$^1$, —NR$^{10}$C(O)N(R$^{10}$)$_2$, —NR$^{10}$CO$_2$R$^{12}$, —CO$_2$R$^1$, —C(O)R$^1$, —C(O)N(R$^{10}$)$_2$, —OC(O)N(R$^{10}$)$_2$, —S(O)$_2$R$^{12}$, —SO$_2$N(R$^{10}$)$_2$, —S(O)R$^{12}$, —NR$^{10}$SO$_2$N(R$^{10}$)$_2$, or —NR$^{10}$SO$_2$R$^{12}$;
R$^8$ is -halo, —CN, or a substituted or unsubstituted group selected from —R$^{12}$, —OR$^1$, —SR$^{12}$, —N(R$^{10}$)$_2$, —NR$^{10}$C(O)R$^{12}$, —NR$^{10}$CO$_2$R$^{12}$, —CO$_2$R$^1$, —C(O)R$^1$, —C(O)N(R$^{10}$)$_2$, —OC(O)N(R$^{10}$)$_2$, —S(O)$_2$R$^{12}$, —SO$_2$N(R$^{10}$)$_2$, —S(O)R$^{12}$, —NR$^{10}$SO$_2$N(R$^{10}$)$_2$ and —NR$^{10}$SO$_2$R$^{12}$ groups, or two adjacent R$^8$ groups taken together with their intervening atoms form a 5-6 membered unsaturated or partially unsaturated ring having 0-2 heteroatoms selected from nitrogen, oxygen and sulfur;
R$^4$ and R$^5$ are each independently C$_{1-3}$ alkyl, or R$^4$ and R$^5$ taken together with their intervening nitrogen form a 5-6 membered ring;
each R$^{13}$ is hydrogen;
each R$^{10}$ is hydrogen;
each R$^{11}$ is independently selected from hydrogen and optionally substituted C$_{1-5}$ aliphatic groups; and
each R$^{12}$ is independently selected from optionally substituted C$_{1-5}$ aliphatic groups.

8. The compound or salt of claim 7 wherein:
R$^7$ is absent or is halo; and
Ring B is a naphthyl ring.

9. The compound or salt thereof of claim 1, wherein the compound is of formula III-A or III-B:

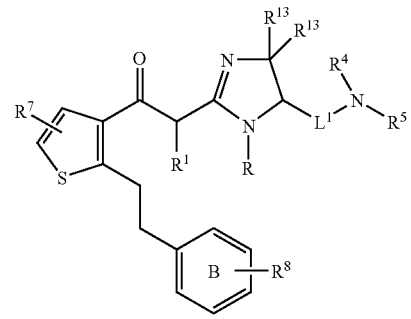

III-A

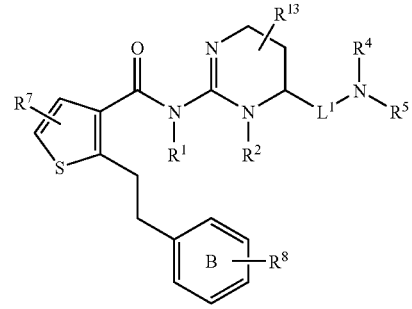

III-B wherein:
R$^1$ and R$^2$ are each hydrogen;
R$^3$ is hydrogen;

$L^1$ is —CH$_2$CH$_2$— or —CH$_2$CH$_2$CH$_2$—;

$R^7$ is absent or is -halo, —CO$_2$R$^1$, —C(O)R$^1$ or —C(O)N(R$^{10}$)$_2$, or two adjacent $R^7$ groups taken together with their intervening atoms form a 5-6 membered unsaturated or partially unsaturated ring having 0-2 heteroatoms selected from nitrogen, oxygen and sulfur;

$R^8$ is -halo, —NO$_2$, —CN, or a substituted or unsubstituted group selected from —R$^{12}$, —OR$^1$, —SR$^{12}$, —C$_{6-10}$ aryl, -heterocyclyl, -heteroaryl, —C$_{6-10}$-aryl)alkyl, -(heterocyclyl)alkyl, -heteroaryl)alkyl, —N(R$^{10}$)$_2$, —NR$^{10}$C(O)R$^1$, —NR$^{10}$C(O)N(R$^{10}$)$_2$, —NR$^{10}$CO$_2$R$^{12}$, —CO$_2$R$^1$, —C(O)R$^1$, —C(O)N(R$^{10}$)$_2$, —OC(O)N(R$^{10}$)$_2$, —S(O)$_2$R$^{12}$, —SO$_2$N(R$^{10}$)$_2$, —S(O)R$^{12}$, —NR$^{10}$SO$_2$N(R$^{10}$)$_2$, —NR$^{10}$SO$_2$R$^{12}$, and —C(=NH)—N(R$^{10}$)$_2$ groups, or two adjacent $R^8$ groups taken together with their intervening atoms form a 5-6 membered unsaturated or partially unsaturated ring having 0-2 heteroatoms selected from nitrogen, oxygen and sulfur;

$R^4$ and $R^5$ are each independently C$_{1-3}$ alkyl, or $R^4$ and $R^5$ taken together with their intervening nitrogen form a 5-6 membered ring;

each $R^{13}$ is independently selected from hydrogen, C$_{1-6}$ aliphatic, C(O)R$^1$, CO$_2$R$^1$, CN,)—N(R$^{10}$)$_2$, C(O)N(R$^{10}$)$_2$ and -OR$^1$ groups, or two $R^{13}$ groups on the same carbon taken together form =O, or two $R^{13}$ groups taken together with their intervening atoms form a 3-7 membered ring having 0-2 ring heteroatoms;

each $R^{10}$ is independently selected from hydrogen, optionally substituted C$_{1-8}$ aliphatic groups, C(O)R$^1$, CO$_2$R$^1$ and SO$_2$R$^1$ groups, or two $R^{10}$ groups on the same nitrogen taken together with the nitrogen form a 5-8 membered aromatic or non-aromatic ring having, in addition to the nitrogen, 0-2 ring heteroatoms selected from N, O and S;

each $R^{11}$ is independently selected from hydrogen and optionally substituted C$_{1-8}$ aliphatic groups; and each $R^{12}$ is independently selected from optionally substituted C$_{1-8}$ aliphatic groups.

10. The compound or salt of claim 9 wherein:

$R^1$, $R^2$ and $R^3$ are each hydrogen;

$L^1$ is —CH$_2$CH$_2$— or —CH$_2$CH$_2$CH$_2$—;

$R^7$ is absent;

$R^8$ is -halo, —CN, or a substituted or unsubstituted group selected from —R$^{12}$, —OR$^1$, —SR$^{12}$, —N(R$^{10}$)$_2$, —NR$^{10}$C(O)R$^1$, —NR$^{10}$CO$_2$R$^{12}$, —CO$_2$R$^1$, —C(O)R$^1$, —C(O)N(R$^{10}$)$_2$, —OC(O)N(R$^{10}$)$_2$, —S(O)$_2$R$^{12}$, —SO$_2$N(R$^{10}$)$_2$, —S(O)R$^{12}$, —NR$^{10}$SO$_2$N(R$^{10}$)$_2$, and —NR$^{10}$SO$_2$R$^{12}$ groups, or two adjacent $R^8$ groups taken together with their intervening atoms form a 5-6 membered unsaturated or partially unsaturated ring having 0-2 heteroatoms selected from nitrogen, oxygen and sulfur;

$R^4$ and $R^5$ are each independently C$_{1-3}$ alkyl, or $R^4$ and $R^5$ taken together with their intervening nitrogen form a 5-6 membered ring;

each $R^{13}$ is hydrogen;

each $R^{10}$ is hydrogen;

each $R^{11}$ is independently selected from hydrogen and optionally substituted C$_{1-5}$ aliphatic groups; and each $R^{12}$ is independently selected from optionally substituted C$_{1-5}$ aliphatic groups.

11. The compound or salt of claim 7 wherein:

Ring B is a phenyl ring having two $R^8$ substituents that are para to one another, each $R^8$ being independently selected from halo, C$_{1-4}$ alkyl, C$_{1-3}$ alkoxy, CO(C$_{1-3}$ alkyl), CONH(C$_{1-3}$ alkyl), SO$_2$(C$_{1-3}$ alkyl), and SO$_2$NH(C$_{1-3}$ alkyl), or Ring B is a naphthyl ring.

12. The compound or salt thereof according to claim 1, wherein the compound is selected from the group consisting of:

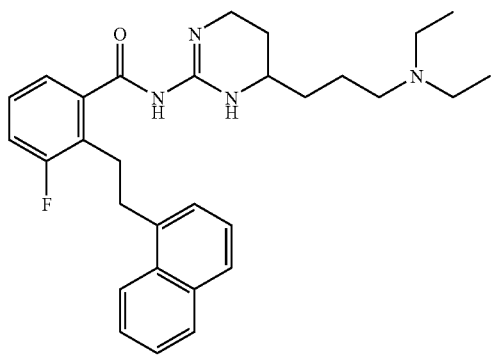

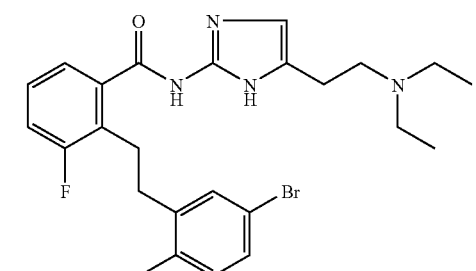

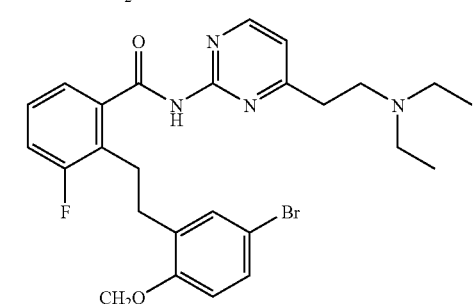

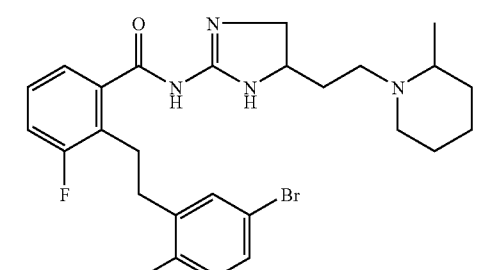

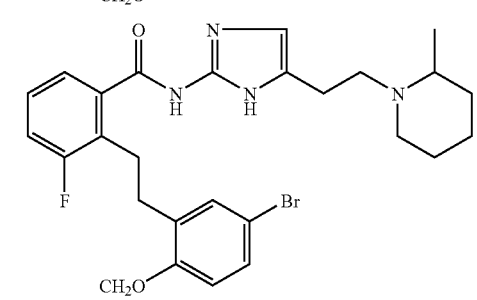

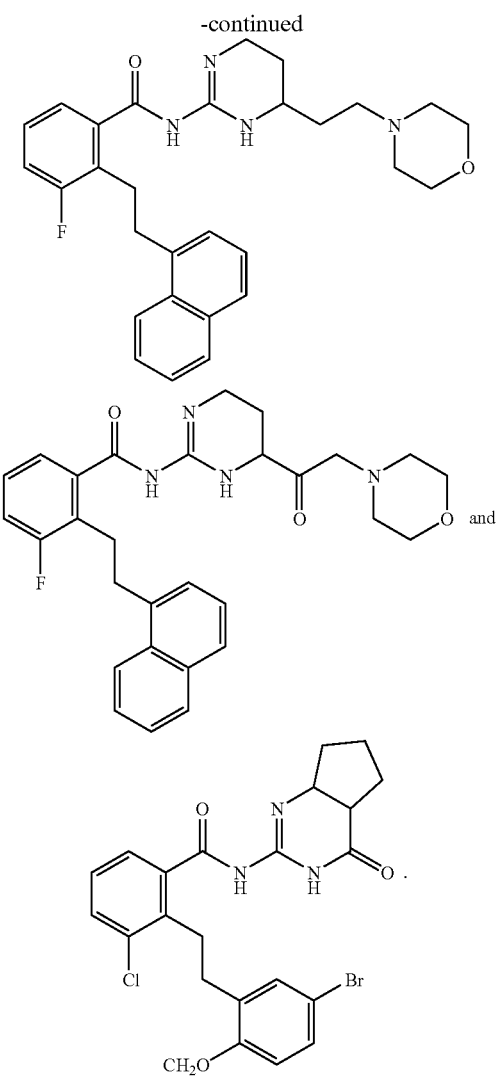

13. A pharmaceutical composition comprising a compound or salt according to claim 1 and a pharmaceutically acceptable carrier.

14. A method for alleviating or halting progression of symptoms of a weight loss disorder in a patient in need thereof, comprising administering to said patient a compound of formula I in claim 1 or a salt thereof, wherein the weight loss disorder is a cachexia, aging involuntary weight loss, catabolic wasting or anorexia.

15. The method of claim 14, wherein the weight loss disorder is a cachexia selected from the group consisting of cancer cachexia, cardiac cachexia, chronic illness cachexia and AIDS cachexia.

16. A method for alleviating or halting progression of symptoms of a bone associated disorder in a patient in need thereof, comprising administering to said patient a compound of formula I in claim 1 or a salt thereof, wherein the bone associated disorder is osteoporosis, bone fractures, bone formation associated with surgical procedures, osteogenesis imperfecta, hypophosphatasia, Paget's disease, fibrous dysplasia, osteopetrosis, myeloma bone disease, or the depletion of calcium in bone.

17. A method for alleviating or halting progression of symptoms of a neuronal disorder in a patient in need thereof, comprising administering to said patient a compound of formula I in claim 1 or a salt thereof, wherein the neuronal disorder is neuropathic pain or allodynia.

18. A method of inhibiting MC4-R activity in a patient in need thereof comprising administering to said patient a pharmaceutical composition comprising a compound of formula I in claim 1 or a salt thereof.

* * * * *

UNITED STATES PATENT AND TRADEMARK OFFICE
CERTIFICATE OF CORRECTION

PATENT NO.        : 7,790,719 B2
APPLICATION NO.   : 11/878708
DATED             : September 7, 2010
INVENTOR(S)       : Tricia J. Vos et al.

It is certified that error appears in the above-identified patent and that said Letters Patent is hereby corrected as shown below:

The Specification and claims should be amended to:

(1) Column 3, line 17, replace -$N(R^{11})CO_2$- with -$N(R^{10})CO_2$-

(2) Column 4, line 23, replace –$SO_2N(R^{10},)_2$ with –$SO_2N(R^{10})_2$ (3) Column 4, line 56, incorrectly reads $R^{14}$ of GS. whereas it should read $R^{14}$ of GS

(4) Column 7, line 49, replace –$NR+SO_2R^+$ with –$NR^+SO_2R^+$ (5) Column 13, line 39, replace –Ring with Ring

(6) Column 15, line 1, replace –$SO_2N(R^{10})_2$-$S(O)R^{12}$ with –$SO_2N(R^{10})_2$, -$S(O)R^{12}$ (7) Column 15, line 12, replace –$NR^{10}CO_2R^{12}$, -$C(O)R^1$–$C(O)N(R^{10})_2$ with -$NR^{10}CO_2R^{12}$, -$CO_2R^1$, -$C(O)R^1$, –$C(O)N(R^{10})_2$ (8) Column 15, line 50, replace –$N(R^{11})_2$ with –$N(R^{10})_2$ (9) Column 15, line 51, replace –$CO_2R^1$-$C(O)R^1$-$C(O)N(R^{10})_2$ with –$CO_2R^1$, -$C(O)R^1$, -$C(O)N(R^{10})_2$

(10) Column 15, line 58, replace –$NR^{11}SO_2R^{12}$ with –$NR^{10}SO_2R^{12}$

(11) Column 17, line 15, replace –($C_{5-10}$ aryl)alkyl with –($C_{6-10}$ aryl)alkyl

(12) Column 17, line 20, replace –$C(=NH)$-$N(R^{11})_2$ with –$C(=NH)$-$N(R^{10})_2$

(13) Column 18, line 38, replace $R^7$, $R^1$ with $R^7$, $R^8$

Signed and Sealed this
Eighteenth Day of January, 2011

David J. Kappos
*Director of the United States Patent and Trademark Office*

(14) Column 19, line 27, replace

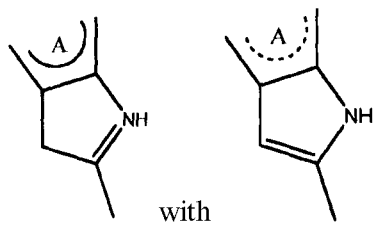

with

(15) Column 19, line 27, replace

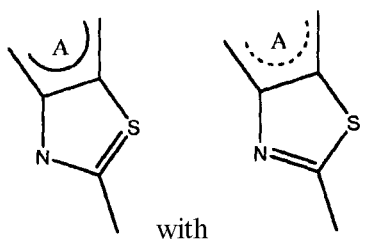

with

(16) Column 68, line 52, replace 1:2H₂O:dioxane with 1:2 H₂O:dioxane

(17) Column 75, line 24, replace 6.63 (d, 7=9.0 Hz, 1H) with 6.63 (d, J=9.0 Hz, 1H)

(18) Column 75, line 43, replace (d, T=8.4 Hz, 1H) with (d, J=8.4 Hz, 1H)

(19) Column 83, line 62, replace (m; with (m,

(20) Column 85, line 36, replace O-5% with 0-5%

(21) Column 89, line 58, replace formula X with formula I

(22) Column 98, line 64, replace Multiprop with MultiDrop

(23) Column 100, line 32, replace [N,D,P]-o(MSH with [N,D,P]-αMSH

(24) Column 101, line 17, replace

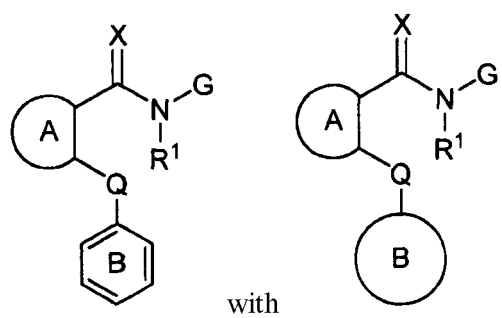

with

CERTIFICATE OF CORRECTION (continued)
U.S. Pat. No. 7,790,719 B2

(25) Column 101, line 35, remove "an optionally substituted 5-6 membered aromatic or non-aromatic ring having two or three ring nitrogens"

(26) Column 102, line 19, replace –CH$_2$CO$_2$R$_1$ and) –C(=O)N(R$^{10}$) with –CH$_2$CO$_2$R$^1$ and –C(=O)N(R$^{10}$)

(27) Column 104, line 53, replace

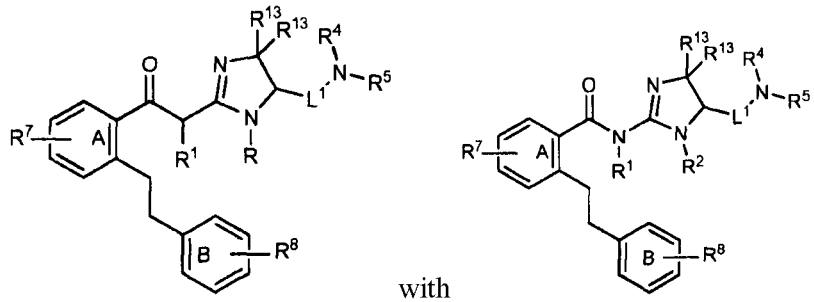

with (see Amendment A, page 10);

(28) Column 105, line 37, replace -heteroaryl)alkyl with -(heteroaryl)alkyl

(29) Column 105, line 54, replace CN,)-N(R$^{10}$)$_2$ with CN, -N(R$^{10}$)$_2$

(30) Column 106, line 39, replace

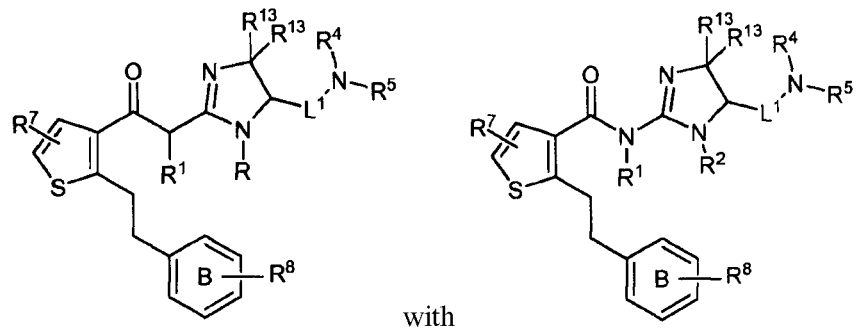

with (see Amendment A, page 14);

(31) Column 107, line 9, replace –C$_{6-10}$-aryl)alkyl with –(C$_{6-10}$ aryl)alkyl

(32) Column 107, line 10, replace –heteroaryl)alkyl with –(heteroaryl)alkyl

(33) Column 107, line 24, replace CN,)-N(R$^{10}$)$_2$ with CN, -N(R$^{10}$)$_2$

CERTIFICATE OF CORRECTION (continued)
U.S. Pat. No. 7,790,719 B2

Page 4 of 5

(34) Column 108, line 32, replace

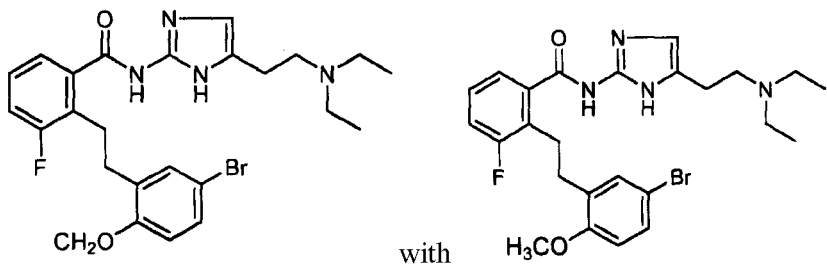

with

(35) Column 108, line 43, replace

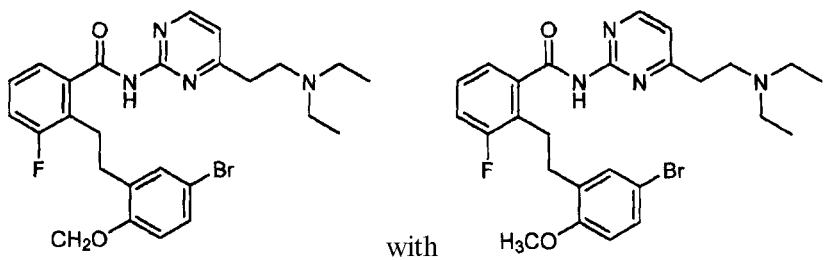

with

(36) Column 108, line 54, replace

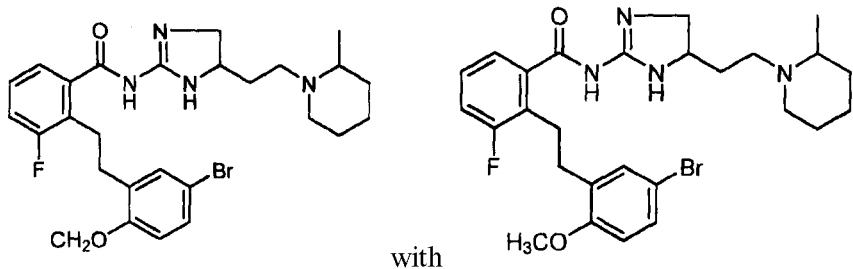

with

(37) Column 108, line 66, replace

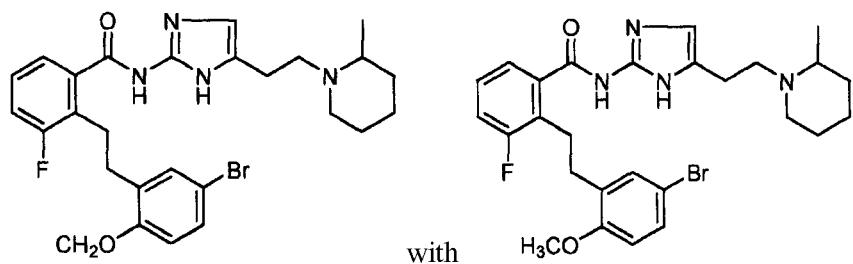

with

CERTIFICATE OF CORRECTION (continued)
U.S. Pat. No. 7,790,719 B2

Page 5 of 5

(38) Column 109, line 28, replace

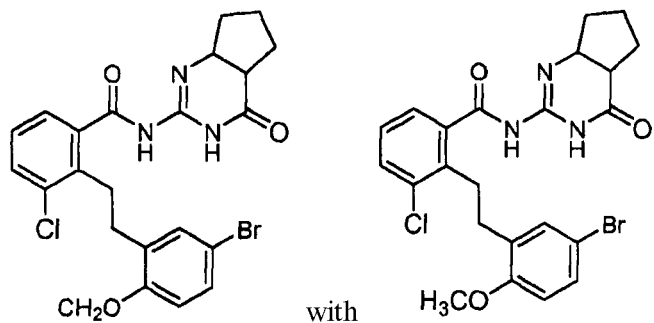 with